US012751976B2

(12) United States Patent
Carmichael et al.

(10) Patent No.: US 12,751,976 B2
(45) **Date of Patent: *Oct. 6, 2026**

(54) INDUCED PLURIPOTENT STEM CELL DERIVED GLIAL ENRICHED PROGENITOR CELLS FOR THE TREATMENT OF WHITE MATTER STROKE

(71) Applicant: The Regents of the University of California, Oakland, CA (US)

(72) Inventors: Stanley Thomas Carmichael, Sherman Oaks, CA (US); Irene Lorenzo Llorente, Los Angeles, CA (US); William E. Lowry, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/674,708

(22) Filed: Feb. 17, 2022

(65) Prior Publication Data

US 2022/0241345 A1 Aug. 4, 2022

Related U.S. Application Data

(63) Continuation-in-part of application No. 15/763,817, filed as application No. PCT/US2016/054007 on Sep. 27, 2016, now Pat. No. 12,544,406.

(60) Provisional application No. 63/151,009, filed on Feb. 18, 2021, provisional application No. 62/236,642, filed on Oct. 2, 2015.

(51) Int. Cl.
*A61K 35/30* (2015.01)
*C12N 5/079* (2010.01)

(52) U.S. Cl.
CPC ............ *A61K 35/30* (2013.01); *C12N 5/0622* (2013.01); *C12N 2500/38* (2013.01); *C12N 2501/11* (2013.01); *C12N 2501/115* (2013.01); *C12N 2506/45* (2013.01)

(58) Field of Classification Search
CPC .. A61K 35/30; C12N 5/0622; C12N 2500/38; C12N 2501/11; C12N 2501/115; C12N 2506/45
See application file for complete search history.

(56) References Cited

U.S. PATENT DOCUMENTS

2018/0271911 A1 9/2018 Carmichael et al.

FOREIGN PATENT DOCUMENTS

WO WO-9908533 A1 2/1999
WO WO-2009137674 A2 * 11/2009 ............ A61K 35/30
WO WO-2012121971 A2 * 9/2012 ............ A61K 31/40
WO WO-2014022423 A2 * 2/2014 ......... A01K 67/0271
WO WO-2014124087 A1 8/2014
WO WO-2017058819 A1 4/2017

OTHER PUBLICATIONS

Borlongan, 2019 (Stem Cells Translational Medicine 2019;8:983-988, http://dx.doi.org/ 10.1002/sctm.19-0076) (Year: 2019).*
Valeri et al, 2023 (Bioengineering 2023, 10(1), 118; doi: 10.3390/bioengineering10010118) (Year: 2023).*
Singh et al., 2020 (Front. Neurosci. 14:473, doi: 10.3389/fnins.2020.00473) (Year: 2020).*
Galiakberova et al., 2020 (Front. Cell Dev. Biol. 8:815., doi: 10.3389/fcell.2020.00815) (Year: 2020).*
Liu et al, 2021 (Stem Cell Research & Therapy (2021) 12:376; https://doi.org/10.1186/s13287-021-02427-1) (Year: 2021).*
Baker et al., 2019 (Brain and Behavior. 2019;9:e01214.; https://doi.org/10.1002/brb3.1214) (Year: 2019).*
Lin et al., 2021 (Mater. Adv., 2021, 2, 2561-2583, DOI: 10.1039/d0ma00732c) (Year: 2021).*
Makrygianni et al (Cells 2023, 12, 1822. https://doi.org/ 10.3390/cells12141822) (Year: 2023).*
Nieto et al (Polymers 2018, 10, 184; doi:10.3390/polym10020184) (Year: 2018).*
Yu et al (Front. Cell. Neurosci. 16:1058753. doi: 10.3389/fncel.2022.1058753) (Year: 2023).*
Ucar (Neurochemistry International 146 (2021) 105033, https://doi.org/10.1016/j.neuint.2021.105033) (Year: 2021).*
Shen et al (Front. Cell. Neurosci. 15:755955. doi: 10.3389/fncel.2021.755955) (Year: 2021).*
Tomov (Neural Regen Res 15(7):1173-1178. doi:10.4103/1673-5374.270296) (Year: 2020).*
Caplan et al (Front. Immunol. 10:1645, doi: 10.3389/fimmu.2019.01645, published Jul. 31, 2019) (Year: 2019).*
Liu et al (Front. Cell. Neurosci. 15:637210. doi: 10.3389/fncel.2021.637210) (Year: 2021).*
Bjorklund et al (Nat Neurosci . Jun. 2000;3(6):537-44. doi: 10.1038/75705.) (Year: 2000).*
Xie et al (Stem Cell Reports, vol. 3, 743-757, Oct. 30, 2014, Doi: 10.1016/j.stemcr.2014.09.021) (Year: 2014).*
Goldman et al (Science. Oct. 26, 2012;338(6106):491-5. doi: 10.1126/science.1218071.) (Year: 2012).*
Strano et al (Cell Reports 31, 107732, Jun. 9, 2020, Doi: 10.1016/j.celrep.2020.107732 ) (Year: 2020).*
Keller et al (Human Reproduction Update, vol. 24, No. 2 pp. 162-175, 2018, Doi: 10.1093/humupd/dmx042) (Year: 2018).*
Duan et al (Front. Neurosci. 15:628663. doi: 10.3389/fnins.2021.628663, May 28, 2021) (Year: 2021).*
Sheikh et al ( Regen Med Rep. 2024;1(1):76-92., doi: 10.4103/RMR.REGENMED-D-23-00002) (Year: 2024).*
Marin et al (Neurobiology of Disease 126 (2019) 5-12, Doi: 10.1016/j.nbd.2018.07.023) (Year: 2019).*

(Continued)

*Primary Examiner* — Peter Paras, Jr.
*Assistant Examiner* — Khoa Nhat Tran
(74) *Attorney, Agent, or Firm* — Norton Rose Fulbright US LLP

(57) ABSTRACT

In various embodiments methods and compositions for improving a recovery of a subject after a cerebral ischemic injury, such as white matter stroke are provided. In certain embodiments, the methods involve administering human induced pluripotent glial enriched progenitor cells into the brain of the subject.

13 Claims, 29 Drawing Sheets
(19 of 29 Drawing Sheet(s) Filed in Color)

(56) References Cited

OTHER PUBLICATIONS

Ahmad et al., (2015) "Optimization of a clinically relevant model of white matter stroke in mice: histological and functional evidences", Journal of Neurology and Neurosurgery, 2(2): Article No. 21000114 (7 pages) (Epub. Aug. 20, 2015).
Clemente et al., (2013) "The effect of glia-glia interactions on oligodendrocyte precursor cell biology during development and in demyelinating diseases", Frontiers in Cellular Neuroscience, 7(268): 15 pages.
EP Extended European Search Report dated Feb. 22, 2019 issued in EP 16852426.2.
EP Office Action dated Dec. 6, 2019 issued in EP 16852426.2.
Goldman et al., (2012) "Glial Progenitor Cell-Based Treatment and Modeling of Neurological Disease", Science, 338(6106): 491-495.
Han et al., (2013) "Forebrain Engraftment by Human Glial Progenitor Cells Enhances Synaptic Plasticity and Learning in Adult Mice", Cell Stem Cell, 12(3): 342-353.
Hinman et al. (2013) "Remodeling of the Axon Initial Segment After Focal Cortical and White Matter Stroke" Stroke 44(1): 182-189.
JP Office Action dated Oct. 19, 2020 issued in JP 2018-516741.
JP Office Action (Final) dated Sep. 6, 2021 issued in JP 2018-516741.
Li et al., (2015) "CXCL12 gene therapy ameliorates ischemia-induced white matter injury in mouse brain", Stem Cells Translational Medicine, 4(10): 1122-1130 (Epub. Aug. 7, 2015).
Li et al., (2015) "Human iPS cell-derived astrocyte transplants preserve respiratory function after spinal cord injury", Experimental Neurology, 271: 479-492.
Llorente et al., (2021) "Patient-derived glial enriched progenitors repair functional deficits due to white matter stroke and vascular dementia in rodents", Sci. Transl. Med., 13: eaaz6747 (18 pages) DOI: 10.1126/scitranslmed.aaz6747.
Otero-Ortega et al., (2015) "White matter injury restoration after stem cell administration in subcortical ischemic stroke", Stem Cell Research & Therapy, 6(121): I-12 (Epub. Jun. 19, 2015).
Patterson et al., (2012) "Defining the nature of human pluripotent stem cell progeny", Cell Research, 22: 178-193.
PCT International Preliminary Report on Patentability dated Apr. 3, 2018 issued in PCT/US2016/054007.
PCT International Search Report and Written Opinion dated Jan. 6, 2017 issued in PCT/US2016/054007.
Santilli et al. (2010) "Mild Hypoxia Enhances Proliferation and Multipotency of Human Neural Stem Cells" PLOS one 5(1): e8575 (12 pages).
Sozmen et al., (2009) "A white matter stroke model in the mouse: axonal damage, progenitor responses and MRI correlates", Journal of Neuroscience Methods, 180(2): 261-272 (Epub. Mar. 31, 2009).
US Final Office Action dated Aug. 6, 2020 issued in U.S. Appl. No. 15/763,817.
US Office Action dated Jun. 10, 2021 issued in U.S. Appl. No. 15/763,817.
US Office Action dated Nov. 29, 2020 issued in U.S. Appl. No. 15/763,817.
Wang et al. (2011) "Combination of Hyaluronic Acid Hydrogel Scaffold and PLGA Microspheres for Supporting Survival of Neural Stem Cells" Pharm Res 28:1406-1414.
Windrem et al., (2008) "Neonatal Chimerization with Human Glial Progenitor Cells Can Both Remyelinate and Rescue the Otherwise Lethally Hypomyelinated Shiverer Mouse", Cell Stem Cell, 2(6): 553-565.
Xie et al., (2014) "Defining the Role of Oxygen Tension in Human Neural Progenitor Fates", Stem Cell Reports, 3(5): 743-757.
Yu et al. (2007) "Induced Pluripotent Stem Cell Lines Derived from Human Somatic Cells" Science 318(5858): 1917-1920.
Zhong et al. (2010) "Hydrogel Matrix to Support Stem Cell Survival After Brain Transplantation in Stroke" Neurorehabilitation and Neural Repair 24(7): 636-644.
Armstrong, R.J et al., "Porcine Neural Xenografts in the Immunocompetent Rat: Immune Response Following Grafting of Expanded Neural Precursor Cells", Neuroscience, 2001, vol. 106, No. 1, pp. 201-216.
Barker, R.A. et al., "A Role for Complement in the Rejection of Porcine Ventral Mesencephalic Xenografts in a Rat Model of Parkinson's Disease", The Journal of Neuroscience, May 1, 2000, vol. 20, No. 9, pp. 3415-3424.
Bjorklund, A., et al., "Cell replacement therapies for central nervous system disorders", Nature Neuroscience, Jun. 2000, vol. 3, No. 6, pp. 537-544.
Dobkin, B.H. et al., "The Specific Requirements of Neural Repair Trials for Stroke", Neurorehabilitation and Neural Repair, Jun. 2016, vol. 30, No. 5, vol. 470-478.
JP Office Action dated Jul. 19, 2022, in Application No. JP2018-516741.
JP Office Action dated Sep. 12, 2022, in Application No. JP2018-516741.
Liu, H., et al., "Insight Into the Mechanisms and the Challenges on Stem Cell-Based Therapies for Cerebral Ischemic Stroke", Frontiers in Cellular Neuroscience, 2021, vol. 15, pp. 1-10.
Loseva, E.V. et al., "Comparison of Reactive Processes in the Rat Brain Elicited by Xenotransplantation of Nervous Tissues of Chicken or Pulmonate Snail", Brain Research, Oct. 12, 2001, vol. 915, No. 2, pp. 125-132.
Milosevic, J. et al., "Non-hypoxic stabilization of hypoxia-inducible factor alpha (HIF-a): relevance in neural progenitor/stem cells", May 2009, vol. 15, No. 4, pp. 367-380.
R & D Systems Publication, "Neural Stem Cells & Differentiation Markers", Neuroscience Focus: Neural Stem Cells, 2011, Tools for Cell Biology Research, pp. 1-5.
Tomov, N., Glial Cells in Intracerebral Transplantation for Parkinson's Disease, Neural Regeneration Research, Jul. 2020, vol. 15, No. 7, 1173-1178.
U.S. Non-Final Office Action dated Oct. 13, 2022 in U.S. Appl. No. 15/763,817.
Llorente, I.L. et al., "Reliable generation of glial enriched progenitors from human fibroblast-derived iPSCs", *Stem Cell Res.*, 55: 102458, 2021.
Moshayedi, M. et al., "Systematic optimization of engineered hydrogel allows for selective control of human neural stem cell survival and differentiation after transplantation in the stoke brain", *Biomaterials*, 105: pp. 145-155, 2016.
Nih, L.R. et al., "Engineered HA hydrogel for stem cell transplantation in the brain: Biocompatibility data using a design of experiment approach", *Data in Brief*, 10; pp. 202-209, 2017.
Jiang et al. "hESC-derived Olig2+ progenitors generate a subtype of astroglia with protective effects against ischemic brain injury", *Nature Communications*, vol. 3, pp. 1-16, 2013.
Seo et al. "Experimental global ischemia and white matter injury", *White Matter Injury in Stroke and CNS Disease*, vol. 4, pp. 197-216, 2014.

* cited by examiner

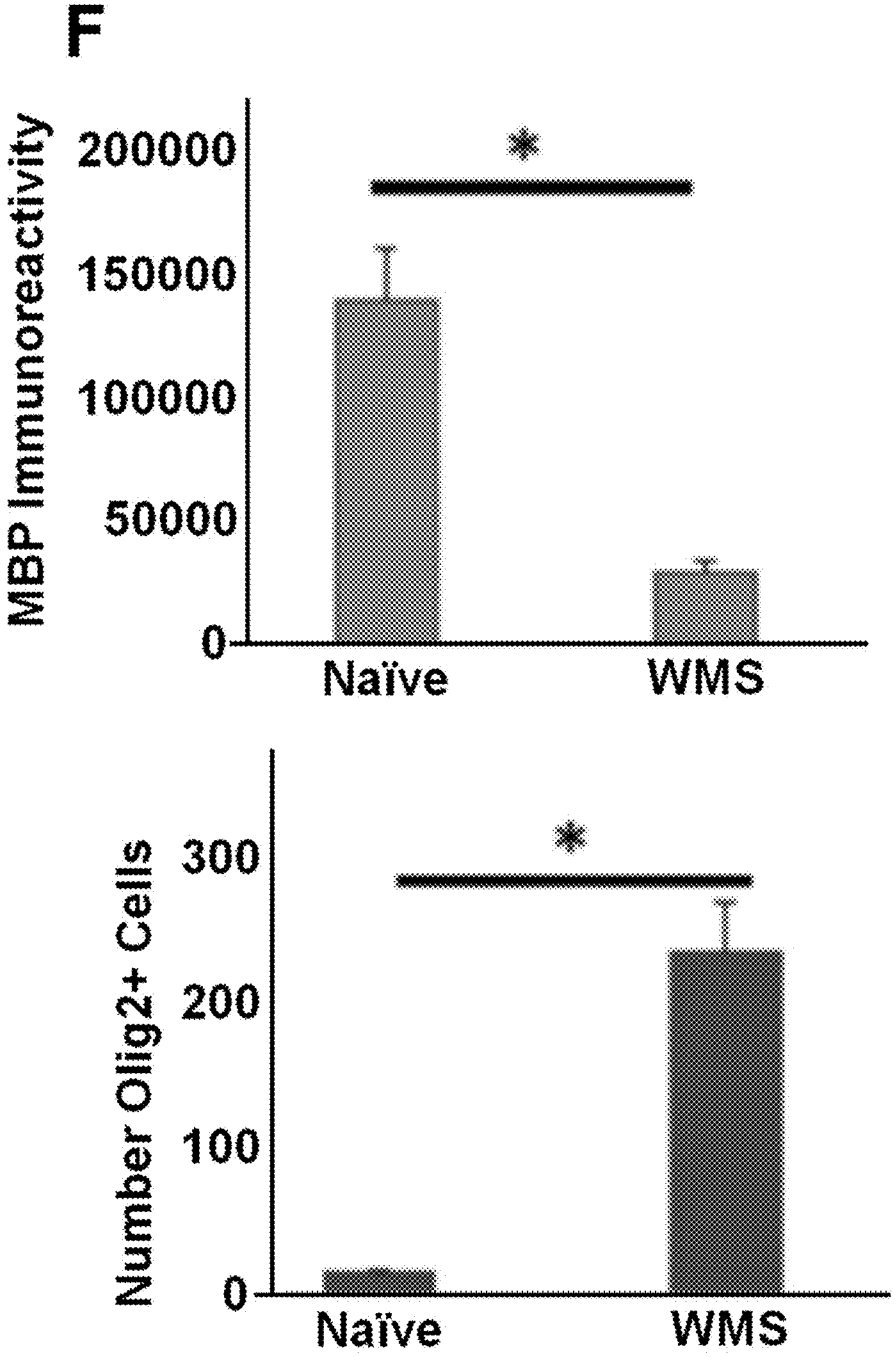
*Fig. 4, cont'd.*

Dots represent the position of single human cells

A

B

C

A

B

INDUCED PLURIPOTENT STEM CELL DERIVED GLIAL ENRICHED PROGENITOR CELLS FOR THE TREATMENT OF WHITE MATTER STROKE

CROSS-REFERENCE TO RELATED APPLICATIONS

This application claims priority to and benefit of U.S. Ser. No. 63/151,009, filed on Feb. 18, 2021, which is incorporated herein by reference in its entirety for all purposes. This application is also a Continuation-in-Part of U.S. Ser. No. 15/763,817, filed on Mar. 27, 2018, which is a U.S. 371 National phase of PCT/US2016/054007, filed on Sep. 27, 2016, which claims benefit of and priority to U.S. Ser. No. 62/236,642, filed on Oct. 2, 2015, all of which are incorporated herein by reference in their entirety for all purposes.

STATEMENT OF GOVERNMENTAL SUPPORT

[Not Applicable]

BACKGROUND

White matter stroke (WMS) occurs in deep penetrating blood vessels in the brain (1-3). Subcortical WMS constitutes up to 30% of all stroke subtypes (4). These infarcts produce cognitive impairments and motor and sensory loss with incomplete recovery. WMS expands or progresses into adjacent white matter (WM) (5-7), to produce larger WM lesions over time and increasing gait abnormalities, verbal processing deficits and difficulties in executive functioning that present as vascular dementia (3,8). Currently, there is no therapy that enhances the brain's own ability to recover from this disease, or prevent the expansion of WMS over time.

To date, successful cell transplant leading to neural repair in WMS has not been achieved. Because of the different cellular constituents of WM, WMS, unlike large artery or "grey matter" stroke, damages primarily astrocytes, axons, oligodendrocytes, and myelin (3, 7). As demyelination renders axons more vulnerable to later degeneration, the expansion of WMS is associated with degeneration of partially de-myelinated axons. There is increasing evidence that myelin plays important roles in the metabolic support (9) structural integrity (10), and plasticity of neuronal function (11), and recent studies have shown that promoting early remyelination in models such as experimental autoimmune encephalitis (EAE) may prevent axon loss (12). Restoring myelin structure may have beneficial effects on the survival or axons adjacent to WMS and prevent lesion expansion. Similar tissue repair goals are present in the other major WM disease of the adult, such as multiple sclerosis.

SUMMARY

We hypothesized that an astrocytic therapy would be a good target for brain repair after WMS. In brain development, immature astrocytes promote oligodendrocyte precursor cell (OPC) differentiation and myelination (13). In central nervous system (CNS) demyelinating lesions, astrocytes promote OPC differentiation into myelinating oligodendrocytes (14). In models of global brain hypoperfusion, astrocyte-derived diffusible factors promote oligodendrocyte production (15). Transplantation of exogenous glial progenitors or immature astrocytes has been shown to promote re-myelination in spinal cord injury models, genetic WM diseases, multiple sclerosis and radiation models (16). The approach of transplanting glial progenitor cells might also be effective in WMS.

We and others recently demonstrated that brief changes in oxygen tension can alter the fate commitment of human induced pluripotent stem (hiPSC) cells towards immature astrocytes, which can be mimicked by prolyl hydroxylase inhibitors, such as deferoxamine (17,18). This process allows for rapid and efficient production of astrocytes derived from an hiPSC source (hiPSC-GEPs). Furthermore, if the fate-change induced by HIF activation is permanent, this could present an optimal solution for brain repair after WMS that allows scaling of this process for a clinical application.

As described in the examples provided herein, hiPSC-GEPs were tested in a model of large subcortical WMS in mice that mimics aspects of vascular dementia. These cells were transplanted at a late or subacute stage after the infarct, as would be necessary in this disease presentation. hiPSC-GEPs migrated widely in the injured brain and stimulated endogenous OPC differentiation, promoted myelination of damaged brain tissue and drove the formation of cortical connections after stroke. hiPSC-GEPs promoted recovery of neurological deficits after WMS. This recovery was more substantial and complete compared to other hiPSC derived cell types, including hiPSC-Neural Progenitor cells (hiPSC-NPC) without an astrocytic differentiation bias.

Based on the transcriptomic analyses described herein we demonstrate the repair capabilities of the hiPSC-GEPs after white matter stroke and provide insights about the key molecular and cellular events of white matter repair associated with hiPSC-GEPs transplant after WMS.

Accordingly, in various embodiments described herein, methods are provided, inter alia, for treating a subject after a cerebral ischemic injury and/or after neural demyelination. In some embodiments the cerebral ischemic injury is white matter subcortical stroke.

In certain embodiments, methods for improving motor and/or cognitive function and/or speech of a subject after a cerebral ischemic injury are provided where the methods comprise administering a therapeutically effective amount of human induced pluripotent glial-enriched progenitor into and/or directly adjacent to the infarct core in the brain of said subject. In some embodiments the cerebral ischemic injury is white matter subcortical stroke. In certain embodiments, the subject is a human. In some embodiments, the method comprises administering the human induced pluripotent glial-enriched progenitor into the infarct core. In other embodiments, the method comprises administering the human induced pluripotent glial-enriched progenitor cells j directly adjacent to the infarct core. In yet other embodiments, the invention provides a pharmaceutical composition for the treatment of subcortical while matter stroke, comprising human induced pluripotent glial-enriched progenitors.

Thus, various embodiments contemplated herein may comprise, but need not be limited to, one or more of the following:

Embodiment 1: A method of improving recovery of a mammal after a cerebral ischemic injury, said method comprising administering a therapeutically effective amount of induced pluripotent glial-enriched progenitor cells (iPSC-GEPs) into the brain of said mammal.

Embodiment 2: The method of embodiment 1, wherein said iPSC-GEPs are administered into or adjacent to the infarct core in the brain of said mammal.

Embodiment 3: The method according to any one of embodiments 1-2, wherein said iPSC-GEPs after administration into the brain mature into astrocytes with a pro-repair phenotype.

Embodiment 4: The method according to any one of embodiments 1-3, wherein said iPSC-GEPs after administration into the brain induce endogenous oligodendrocyte precursor proliferation and re-myelination.

Embodiment 5: The method according to any one of embodiments 1-4, wherein said iPSC-GEPs after administration into the brain promote axonal sprouting.

Embodiment 6: The method according to any one of embodiments 1-5, wherein the cerebral ischemic injury is subcortical white matter stroke.

Embodiment 7: The method according to any one of embodiments 1-6, wherein the cerebral ischemic injury is vascular dementia.

Embodiment 8: The method according to any one of embodiments 1-7, wherein the mammal is a human.

Embodiment 9: The method according to any one of embodiments 1-8, wherein said progenitor cells are human induced pluripotent glial-enriched progenitor cells.

Embodiment 10: The method according to any one of embodiments 1-9, wherein said progenitor cells are administered directly to the infarct core.

Embodiment 11: The method according to any one of embodiments 1-9, wherein said progenitor cells are administered into the subcortical white matter outside of the infarct core.

Embodiment 12: The method according to any one of embodiments 1-11, wherein said progenitor cells are administered during the subacute time period after the ischemic injury.

Embodiment 13: The method according to any one of embodiments 1-12, wherein said progenitor cells are administered via an injection or cannula.

Embodiment 14: The method of embodiment 13, wherein said progenitor cells are contained in a buffer.

Embodiment 15: The method according to any one of embodiments 1-12, wherein said progenitor cells are administered using a depot delivery system.

Embodiment 16: The method of embodiment 15, wherein the depot delivery system comprises a hydrogel.

Embodiment 17: The method of embodiment 16, wherein said hydrogel comprises a biopolymer.

Embodiment 18: The method of embodiment 17, wherein said hydrogel comprises a thiolated hyaluronate.

Embodiment 19: The method according to any one of embodiments 16-18, wherein the hydrogel comprises thiolated gelatin.

Embodiment 20: The method according to any one of embodiments 16-19, wherein the hydrogel comprises a crosslinking agent.

Embodiment 21: The method according to any one of embodiments 1-20, wherein said progenitor cells are derived from fibroblasts.

Embodiment 22: The method of embodiment 21, wherein said progenitor cells are derived from dermal fibroblasts.

Embodiment 23: The method of embodiment 22, wherein said progenitor cells are derived from neonatal dermal fibroblasts.

Embodiment 24: The method according to any one of embodiments 1-20, wherein said progenitor cells are derived from epithelia cells.

Embodiment 25: The method of embodiment 24, wherein said progenitor cells are derived from renal epithelia cells.

Embodiment 26: The method according to any one of embodiments 1-25, wherein said cerebral ischemic injury is due to a stroke.

Embodiment 27: The method according to any one of embodiments 1-25, wherein said cerebral ischemic injury is due to a head injury.

Embodiment 28: The method according to any one of embodiments 1-25, wherein said cerebral ischemic injury is due to a respiratory failure.

Embodiment 29: The method according to any one of embodiments 1-25, wherein said cerebral ischemic injury is due to a cardiac arrest.

Embodiment 30: The method according to any one of embodiments 1-29, wherein said iPSC-GEPs are derived from cells obtained from said mammal to provide cells that are syngeneic to said mammal.

Embodiment 31: The method according to any one of embodiments 1-29, wherein said iPSC-GEPs are derived from universal donor cells.

Embodiment 32: The method according to any one of embodiments 1-29, wherein said iPSC-GEPs are derived from cells obtained from a mammal that is not the mammal being treated to provide cells that are allogenic to the mammal being treated.

Embodiment 33: The method of embodiment 32, wherein said method comprises administering one or more immunosuppressants to said mammal.

Embodiment 34: The method of embodiment 33, wherein said one or more immunosuppressants comprise an immunosuppressant selected from the group consisting of anti-thymocyte globulin (ATG), cyclosporine, tacrolimus, cyclophosphamide, and prednisone.

Embodiment 35: The method according to any one of embodiments 33-34, wherein said one or more immunosuppressants comprise cyclosporine.

Embodiment 36: The method according to any one of embodiments 33-35, wherein said one or more immunosuppressants comprise prednisone.

Embodiment 37: A method for improving motor or cognitive function of a mammal after a cerebral ischemic injury, said method comprising administering a therapeutically effective amount of induced pluripotent glial-enriched progenitor cells into or adjacent to the infarct core in the brain of said mammal.

Embodiment 38: The method of embodiment 37, wherein said iPSC-GEPs are administered into or adjacent to the infarct core in the brain of said mammal.

Embodiment 39: The method according to any one of embodiments 37-38, wherein said iPSC-GEPs after administration into the brain mature into astrocytes with a pro-repair phenotype.

Embodiment 40: The method according to any one of embodiments 37-39, wherein said iPSC-GEPs after administration into the brain induce endogenous oligodendrocyte precursor proliferation and re-myelination.

Embodiment 41: The method according to any one of embodiments 37-40, wherein said iPSC-GEPs after administration into the brain promote axonal sprouting.

Embodiment 42: The method according to any one of embodiments 37-41, wherein the cerebral ischemic injury is subcortical white matter stroke.

Embodiment 43: The method according to any one of embodiments 37-41, wherein the cerebral ischemic injury is an arterial stroke.

Embodiment 44: The method according to any one of embodiments 37-41, wherein the cerebral ischemic injury is vascular dementia.

Embodiment 45: The method according to any one of embodiments 37-44, wherein the mammal is a human.

Embodiment 46: The method according to any one of embodiments 37-45, wherein said progenitor cells are human induced pluripotent glial-enriched progenitor cells.

Embodiment 47: The method according to any one of embodiments 37-46, wherein said progenitor cells are administered directly to the infarct core.

Embodiment 48: The method according to any one of embodiments 37-46, wherein said progenitor cells are administered into the infarct core.

Embodiment 49: The method according to any one of embodiments 37-48, wherein said progenitor cells are administered during the subacute time period after the ischemic injury.

Embodiment 50: The method according to any one of embodiments 37-49, wherein said progenitor cells are administered using a depot delivery system.

Embodiment 51: The method according to any one of embodiments 37-49, wherein said progenitor cells are administered via an injection or cannula.

Embodiment 52: The method of embodiment 51, wherein said progenitor cells are contained in a buffer.

Embodiment 53: The method of embodiment 50, wherein the depot delivery system comprises a hydrogel.

Embodiment 54: The method of embodiment 53, wherein said hydrogel comprises a biopolymer.

Embodiment 55: The method of embodiment 54, wherein said hydrogel comprises a thiolated hyaluronate.

Embodiment 56: The method according to any one of embodiments 53-55, wherein the hydrogel comprises thiolated gelatin.

Embodiment 57: The method according to any one of embodiments 53-56, wherein the hydrogel comprises a crosslinking agent.

Embodiment 58: The method according to any one of embodiments 37-57, wherein said progenitor cells are derived from fibroblasts.

Embodiment 59: The method of embodiment 58, wherein said progenitor cells are derived from dermal fibroblasts.

Embodiment 60: The method of embodiment 59, wherein said progenitor cells are derived from neonatal dermal fibroblasts.

Embodiment 61: The method according to any one of embodiments 37-57, wherein said progenitor cells are derived from epithelia cells.

Embodiment 62: The method of embodiment 61, wherein said progenitor cells are derived from renal epithelia cells.

Embodiment 63: The method according to any one of embodiments 37-62, wherein said cerebral ischemic injury is due to a stroke.

Embodiment 64: The method according to any one of embodiments 37-62, wherein said cerebral ischemic injury is due to a traumatic injury.

Embodiment 65: The method of embodiment 64, wherein said traumatic injury comprises a head and/or spinal cord injury.

Embodiment 66: The method according to any one of embodiments 37-62, wherein said cerebral ischemic injury is due to a condition selected from the group consisting of multiple sclerosis, the leukodystrophies, the Guillain-Barre Syndrome, the Charcot-Marie-Tooth neuropathy, Tay-Sachs disease, Niemann-Pick disease, Gaucher disease, and Hurler syndrome.

Embodiment 67: The method according to any one of embodiments 37-62, wherein said cerebral ischemic injury is due to a cardiac arrest.

Embodiment 68: The method according to any one of embodiments 37-62, wherein said cerebral ischemic injury is due to a respiratory failure.

Embodiment 69: The method according to any one of embodiments 37-68, wherein said iPSC-GEPs are derived from cells obtained from said mammal to provide cells that are syngeneic to said mammal.

Embodiment 70: The method according to any one of embodiments 37-68, wherein said iPSC-GEPs are derived from universal donor cells.

Embodiment 71: The method according to any one of embodiments 37-68, wherein said iPSC-GEPs are derived from cells obtained from a mammal that is not the mammal being treated to provide cells that are allogenic to the mammal being treated.

Embodiment 72: The method of embodiment 71, wherein said method comprises administering one or more immunosuppressants to said mammal.

Embodiment 73: The method of embodiment 72, wherein said one or more immunosuppressants comprise an immunosuppressant selected from the group consisting of anti-thymocyte globulin (ATG), cyclosporine, tacrolimus, cyclophosphamide, and prednisone.

Embodiment 74: The method according to any one of embodiments 72-73, wherein said one or more immunosuppressants comprise cyclosporine.

Embodiment 75: The method according to any one of embodiments 72-74, wherein said one or more immunosuppressants comprise prednisone.

Embodiment 76: A method of slowing myelin loss, and/or promoting myelin repair, and/or promoting remyelination in a mammal having a demyelinating pathology that effects the central nervous system, said method comprising administering a therapeutically effective amount of induced pluripotent glial-enriched progenitor cells into the brain of said mammal.

Embodiment 77: The method of embodiment 76, wherein said iPSC-GEPs are administered into or adjacent to the infarct core in the brain of said mammal.

Embodiment 78: The method according to any one of embodiments 76-77, wherein said iPSC-GEPs after administration into the brain mature into astrocytes with a pro-repair phenotype.

Embodiment 79: The method according to any one of embodiments 76-78, wherein said iPSC-GEPs after administration into the brain induce endogenous oligodendrocyte precursor proliferation and re-myelination.

Embodiment 80: The method according to any one of embodiments 76-79, wherein said iPSC-GEPs after administration into the brain promote axonal sprouting.

Embodiment 81: The method according to any one of embodiments 76-80, wherein the cerebral ischemic injury is subcortical white matter stroke.

Embodiment 82: The method according to any one of embodiments 76-81, wherein said pathology is selected from the group consisting of multiple sclerosis, an inflammatory demyelinating disease (such as Multiple Sclerosis), a leukodystrophic disorder, a CNS neuropathy, central pontine myelinolysis, a myelopathy, a leukoencephalopathy, and a leukodystrophy.

Embodiment 83: The method according to any one of embodiments 76-82, wherein the mammal is a human.

Embodiment 84: The method according to any one of embodiments 76-83, wherein said progenitor cells are human induced pluripotent glial-enriched progenitor cells.

Embodiment 85: The method according to any one of embodiments 76-84, wherein said progenitor cells are administered directly to the infarct core.

Embodiment 86: The method according to any one of embodiments 76-84, wherein said progenitor cells are administered into the subcortical white matter outside of the infarct core.

Embodiment 87: The method according to any one of embodiments 76-86, wherein said progenitor cells are administered during the subacute time period after the ischemic injury.

Embodiment 88: The method according to any one of embodiments 76-87, wherein said progenitor cells are administered using a depot delivery system.

Embodiment 89: The method of embodiment 88, wherein the depot delivery system comprises a hydrogel.

Embodiment 90: The method of embodiment 89, wherein said hydrogel comprises a biopolymer.

Embodiment 91: The method of embodiment 90, wherein said hydrogel comprises a thiolated hyaluronate.

Embodiment 92: The method according to any one of embodiments 89-91, wherein the hydrogel comprises thiolated gelatin.

Embodiment 93: The method according to any one of embodiments 89-92, wherein the hydrogel comprises a crosslinking agent.

Embodiment 94: The method according to any one of embodiments 76-93, wherein said progenitor cells are derived from fibroblasts.

Embodiment 95: The method of embodiment 94, wherein said progenitor cells are derived from dermal fibroblasts.

Embodiment 96: The method of embodiment 95, wherein said progenitor cells are derived from neonatal dermal fibroblasts.

Embodiment 97: The method according to any one of embodiments 76-93, wherein said progenitor cells are derived from epithelia cells.

Embodiment 98: The method of embodiment 97, wherein said progenitor cells are derived from renal epithelia cells.

Embodiment 99: The method according to any one of embodiments 76-98, wherein said iPSC-GEPs are derived from cells obtained from said mammal to provide cells that are syngeneic to said mammal.

Embodiment 100: The method according to any one of embodiments 76-98, wherein said iPSC-GEPs are derived from universal donor cells.

Embodiment 101: The method according to any one of embodiments 76-98, wherein said iPSC-GEPs are derived from cells obtained from a mammal that is not the mammal being treated to provide cells that are allogenic to the mammal being treated.

Embodiment 102: The method of embodiment 101, wherein said method comprises administering one or more immunosuppressants to said mammal.

Embodiment 103: The method of embodiment 102, wherein said one or more immunosuppressants comprise an immunosuppressant selected from the group consisting of anti-thymocyte globulin (ATG), cyclosporine, tacrolimus, cyclophosphamide, and prednisone.

Embodiment 104: The method according to any one of embodiments 102-103, wherein said one or more immunosuppressants comprise cyclosporine.

Embodiment 105: The method according to any one of embodiments 102-104, wherein said one or more immunosuppressants comprise prednisone.

Embodiment 106: A pharmaceutical composition for the treatment of subcortical white matter stroke, comprising induced pluripotent glial-enriched progenitor cells (iPSC-GEPs).

Embodiment 107: The pharmaceutical composition of embodiment 107, wherein said iPSC-GEPs are capable of maturing into astrocytes with a pro-repair phenotype after administration into the brain of a mammal.

Embodiment 108: The pharmaceutical composition according to any one of embodiments 76-107, wherein said iPSC-GEPs are capable of inducing endogenous oligodendrocyte precursor proliferation and re-myelination after administration into the brain of a mammal.

Embodiment 109: The pharmaceutical composition according to any one of embodiments 76-108, wherein said iPSC-GEPs are capable of promoting axonal sprouting after administration into the brain of a mammal.

Embodiment 110: The pharmaceutical composition according to any one of embodiments 106-109, wherein said progenitor cells are suspended in an injectable buffer.

Embodiment 111: The pharmaceutical composition according to any one of embodiments 106-109, wherein said composition comprises a depot delivery system.

Embodiment 112: The pharmaceutical composition of embodiment 111, wherein the depot delivery system comprises a hydrogel.

Embodiment 113: The pharmaceutical composition of embodiment 112, wherein said hydrogel comprises a biopolymer.

Embodiment 114: The pharmaceutical composition of embodiment 113, wherein said hydrogel comprises a thiolated hyaluronate.

Embodiment 115: The pharmaceutical composition according to any one of embodiments 112-114, wherein the hydrogel comprises thiolated gelatin.

Embodiment 116: The pharmaceutical composition according to any one of embodiments 112-115, wherein the hydrogel comprises a crosslinking agent.

Embodiment 117: The pharmaceutical composition according to any one of embodiments 106-116, wherein said progenitor cells are derived from fibroblasts.

Embodiment 118: The pharmaceutical composition of embodiment 117, wherein said progenitor cells are derived from dermal fibroblasts.

Embodiment 119: The pharmaceutical composition of embodiment 118, wherein said progenitor cells are derived from neonatal dermal fibroblasts.

Embodiment 120: The pharmaceutical composition according to any one of embodiments 106-116, wherein said progenitor cells are derived from epithelia cells.

Embodiment 121: The pharmaceutical composition of embodiment 120, wherein said progenitor cells are derived from renal epithelia cells.

Embodiment 122: The pharmaceutical composition according to any one of embodiments 76-121, wherein said iPSC-GEPs are derived from cells obtained from said mammal to provide cells that are syngeneic to said mammal.

Embodiment 123: The pharmaceutical composition according to any one of embodiments 76-121, wherein said iPSC-GEPs are derived from universal donor cells.

Embodiment 124: The pharmaceutical composition according to any one of embodiments 76-121, wherein said iPSC-GEPs are derived from cells obtained from a mammal that is not the mammal being treated to provide cells that are allogenic to the mammal being treated.

Embodiment 125: The pharmaceutical composition of embodiment 124, wherein said method comprises administering one or more immunosuppressants to said mammal.

Embodiment 126: The pharmaceutical composition of embodiment 125, wherein said one or more immunosuppressants comprise an immunosuppressant selected from the group consisting of anti-thymocyte globulin (ATG), cyclosporine, tacrolimus, cyclophosphamide, and prednisone.

Embodiment 127: The pharmaceutical composition according to any one of embodiments 125-126, wherein said one or more immunosuppressants comprise cyclosporine.

Embodiment 128: The pharmaceutical composition according to any one of embodiments 125-127, wherein said one or more immunosuppressants comprise prednisone.

Embodiment 129: An isolated plurality of cells comprising or consisting of astrocytes characterized by a pro-repair phenotype.

Embodiment 130: The isolated plurality of cells of embodiment 129, wherein said cells are derived from iPSC-GEPs.

Embodiment 131: The isolated plurality of cells according to any one of embodiments 129-130, wherein said iPSC-GEPs are derived from universal donor cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 19:
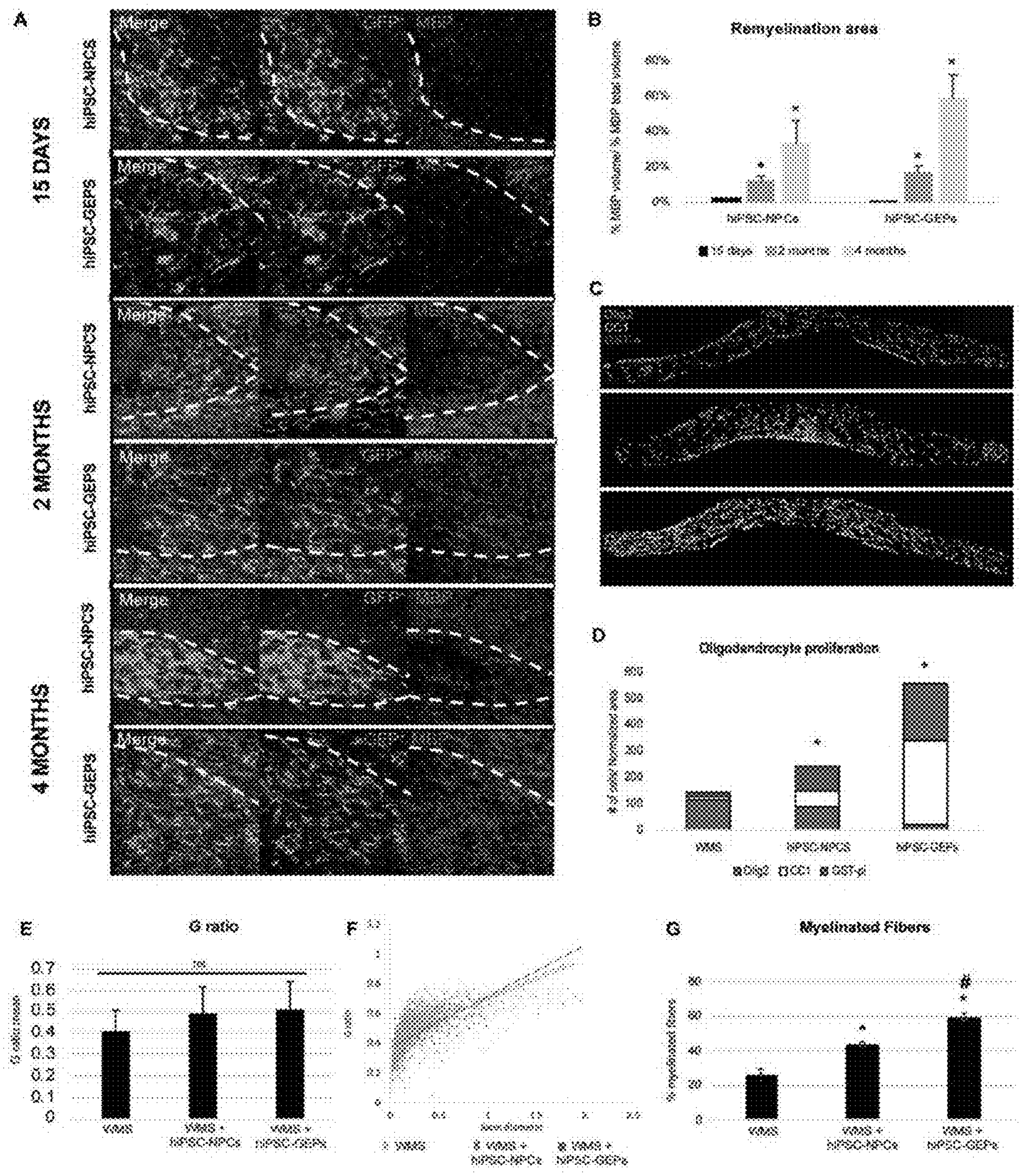

FIG. 19, panels A-G, shows that hiPSC-derived progenitor transplantation promotes oligodendrocyte differentiation and enhances myelin integrity after subcortical white matter damage. Panel A) Image panels show fluorescent immunostaining of GFP+ cells (green) and myelin basic protein (MBP-red) 15 days, 2 and 4 months after stroke injury following hiPSC-NPCs or hiPSC-GEPs transplant. Panel B) Quantification of myelin repair. *P<0.05 by two-way ANOVA followed by Tukey's HSD post hoc analysis, 2- and 4-months hiPSC-NPCs or hiPSC-GEPs transplant vs 15 days hiPSC-NPCs or hiPSC-GEPs transplant comparison. Panel C) 3D distribution of Olig2, CC1 and GSTn+ cells in the subcortical white matter mapped with IMARIS Imaging software. Panel D) Quantification of number of endogenous Olig2/CC1/GSTn+ cells in the ipsilateral white matter. Panels E and F) Quantification of percentages of G ratios were measure 4 months post-WMS. Panel G) Quantification of percentages of myelinated in white matter corpus callosum adjacent to the stroke site 4 months post-stroke. # P<0.05 by twoway ANOVA followed by Tukey's HSD post hoc analysis. B, D, E and G values are means±SEM; n=6 mice per group; N=4.

Figure 20:
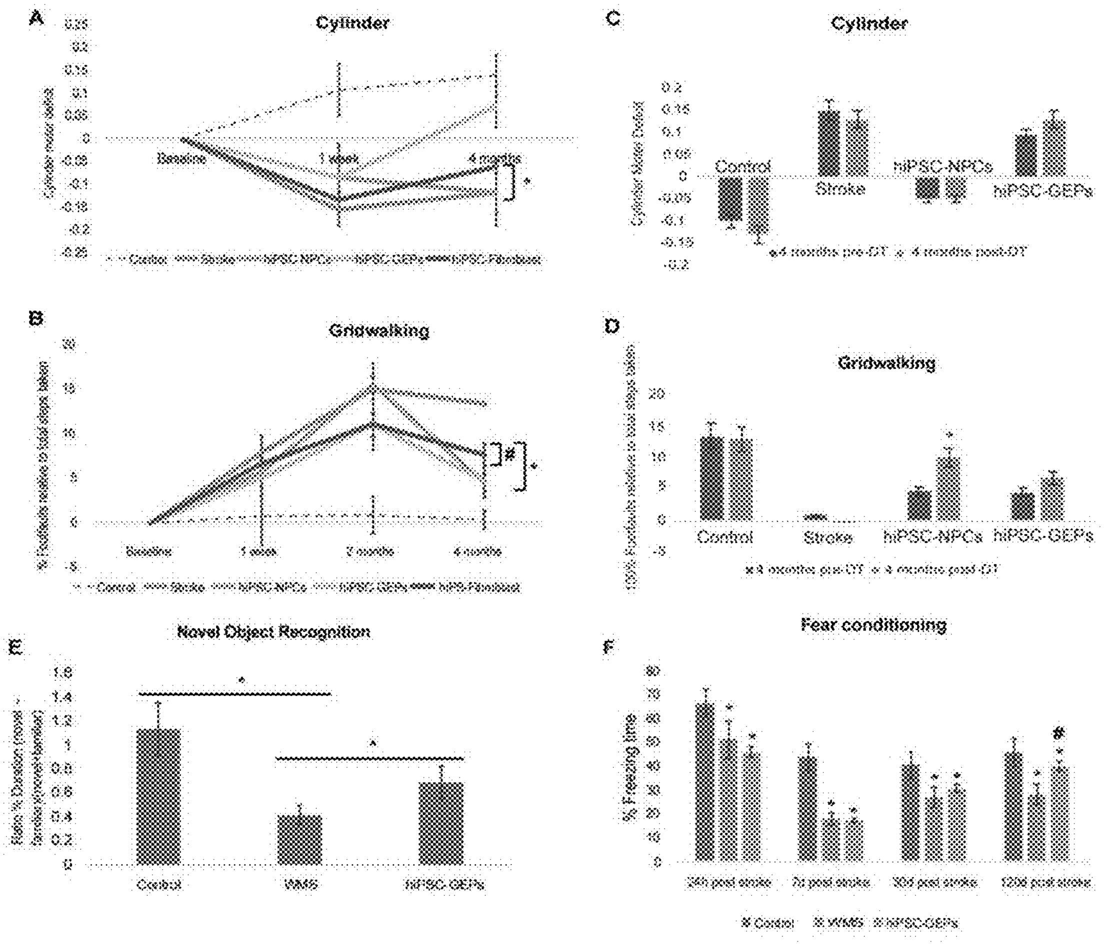

FIG. 20, panels A-F, shows that hiPSC-GEP transplant promotes myelogenesis and improves behavioral outcome after white matter stroke. Panel A) Cylinder test. n=12 mice per group; N=2; * P<0.05 WMS, hiPSC-NPCs or hiPSC-Fibroblast vs control and hiPSC-GEPs by two-way ANOVA followed by Tukey's HSD post hoc analysis values are means±SEM. Panel B) Cylinder test after DT ablation 4 months post-WMS. n=12 mice per group; N=2; two-way ANOVA followed by Tukey's HSD post hoc analysis values are means±SEM. Panel C) Gridwalking test. n=12 mice per group; N=2; *, # P<0.05 *hiPSC-NPCs or hiPSC-GEPs vs WMS, # hiPSC-Fibroblast vs hiPSC-NPCS and hiPSC-GEPs by two-way ANOVA followed by Tukey's HSD post hoc analysis values are means±SEM. Panel D) Gridwalking test. after DT ablation 4 months post-WMS. n=12 mice per group; N=2; * P<0.05 hiPSC-NPCs treatment pre-DT vs hiPSC-NPCs treatment post-DT by two-way ANOVA followed by Tukey's HSD post hoc analysis values are means±SEM. Panel E) Novel object recognition test. n=12 mice per group; N=2; *P<0.05 * Control vs WMS or WMS vs hiPSC-GEPs by two-way ANOVA followed by Tukey's HSD post hoc analysis values are means±SEM. Panel F) Fear Conditioning test. n=12 mice per group; N=2; *P<0.05 * Control vs WMS or hiPSC-GEPs, # WMS vs hiPSC-GEPS by two-way ANOVA followed by Tukey's HSD post hoc analysis values are means±SEM.

Figure 21:
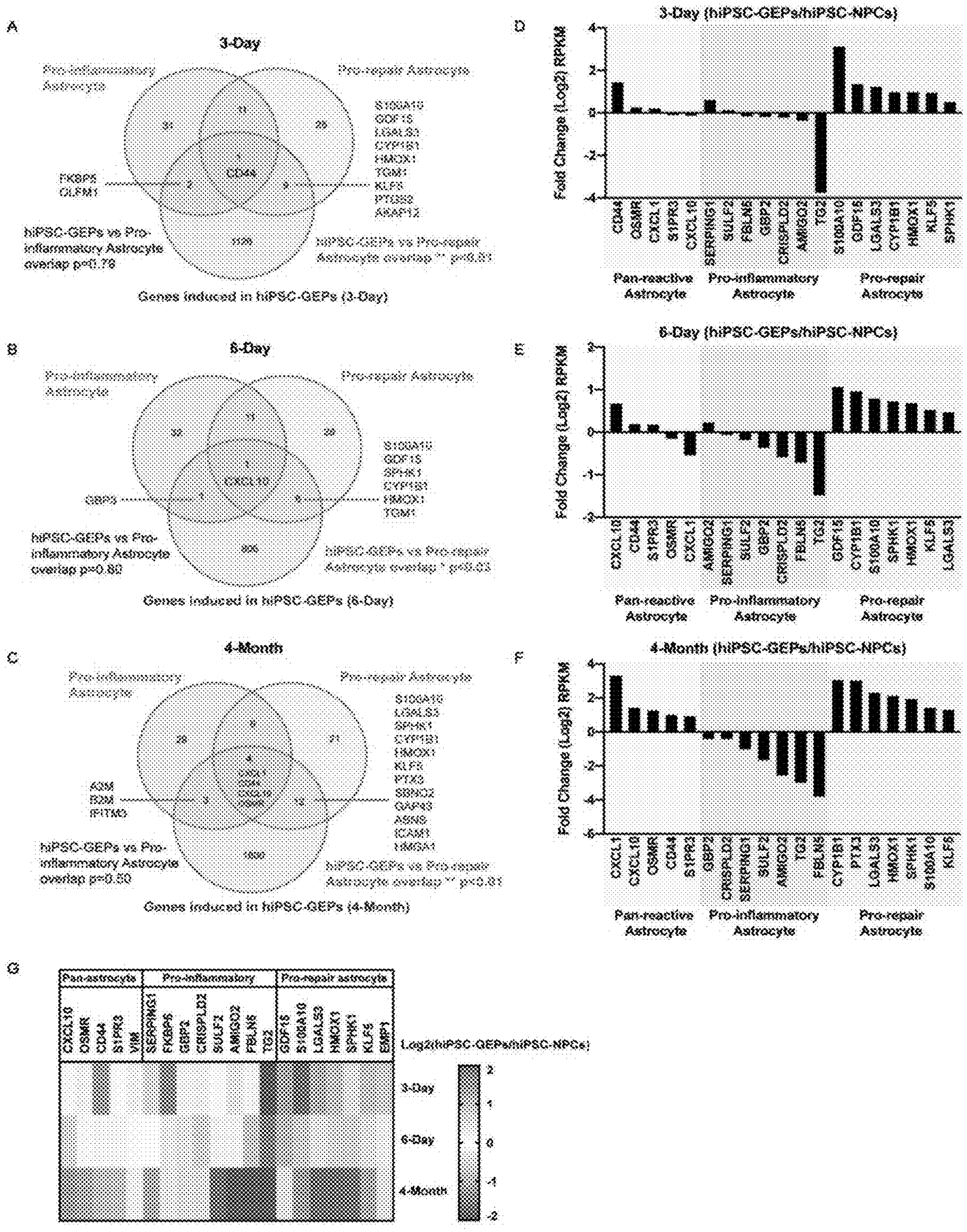

FIG. 21, panels A-G, shows that hiPSC-GEPs represent pro-repair astrocytes, but not pro-inflammatory astrocytes. Panels A-C) Venn diagram overlaid induced genes in hiPSC-GEPs, with genes specifically expressed in pro-inflammatory astrocytes, or pro-repair astrocytes, at 3-day (panel A), 6-day (panel B), and 4-Month (panel C). The enrichment score of GEP versus pro-repair or pro-inflammatory astrocyte was calculated based on hypergeometric test. Panels D-F) Relative fold change (hiPSC-GEP versus hiPSC-NPC) in log scale of representative genes in pan-reactive astrocyte, pro-inflammatory, or pro-repair astrocyte at various time points measured by RNA-seq. Panel G) Heatmap of specific genes in pan-reactive astrocytes, pro-inflammatory, or pro-repair astrocytes suggested that hiPSC-GEPs share similar expression profile with pro-repair astrocytes, but not pro-inflammatory astrocytes.

Figure 22:
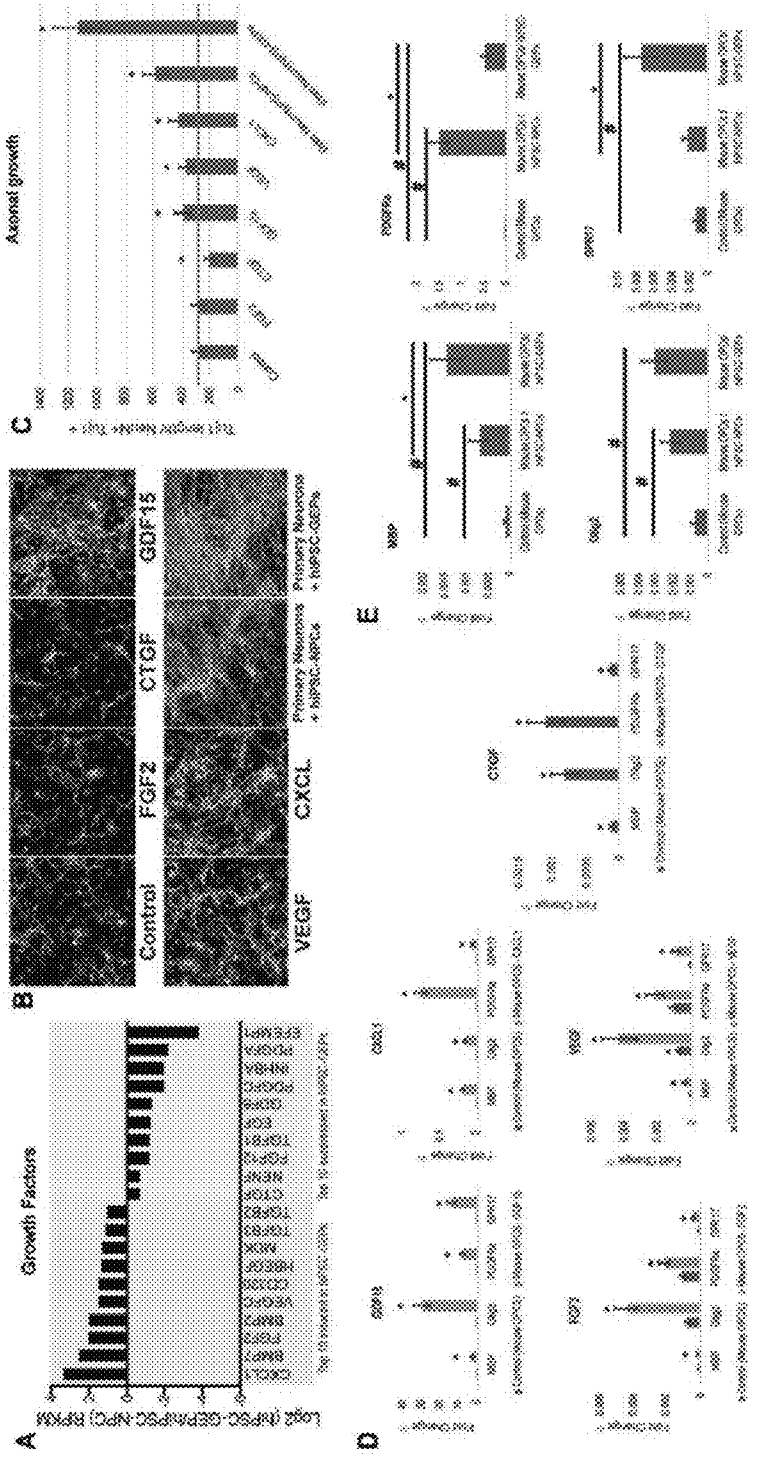

FIG. 22, panels A-E, illustrates key molecular and cellular pathways for white matter repair. Panel A) Top 10 most upregulated and downregulated growth factors 4 months post-DFX treatment. Panel B) Image panels show fluorescent immunostaining of neuronal marker (NeuN-white), b-III tubulin (Tuj1-green), mTau (red) and DAPI (blue) in P4 mouse primary cortical neurons and primary cortical neurons co-culture with hiPSC-NPCS, hiPSC-GEPs or hiPSC-GEPs media. Panel C) Quantification of axonal growth. *P<0.05 by One-way ANOVA followed by Tukey's HSD post hoc analysis, treatments vs control conditions; n=6; N=3. Panel D) Quantification of oligodendrocyte proliferation and differentiation. *p<0.05 by One-way ANOVA followed by Tukey's HSD post hoc analysis, growth factor culture vs control conditions. Panel E) Quantification of oligodendrocyte proliferation and differentiation. *P<0.05 by one-way ANOVA followed by Tukey's HSD post hoc analysis, *hiPSC-GEPs co-cultures vs control conditions, # hiPSC-NPCs co-cultures vs control conditions. Panels C, D and E values are means±SEM; n=3; N=2.

Figure 23:
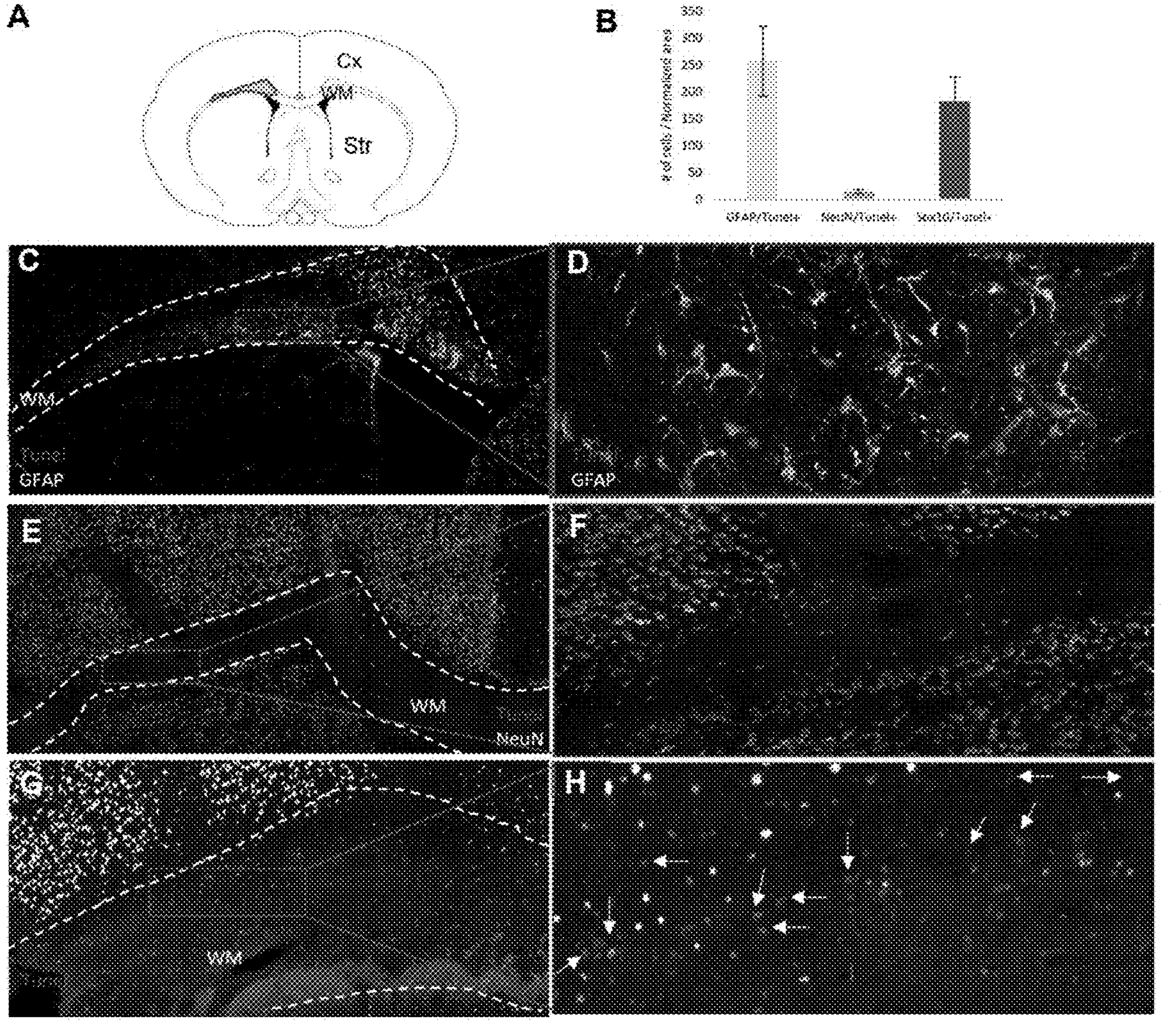

FIG. 23, panels A-H, shows that white matter stroke predominantly damages glial cells. Panel A) Diagram of coronal mouse brain section indicating the focal ischemic lesion. Panel B) Quantification of damaged cells post WMS. Panel C) Image panel show fluorescent immunostaining of Tunel assay (red) and GFAP (white) 1 day after WMS. Panel D) Image panel show high magnification fluorescent immunostaining of Tunel assay (red) and GFAP (white) 1 day after WMS. Panel E) Image panel show fluorescent immunostaining of Tunel assay (red) and NeuN (white) 1 day after WMS. Panel F) Image panel show high magnification fluorescent immunostaining of Tunel assay (red) and NeuN (white) 1 day after WMS. Panel G) Image panel show high magnification fluorescent immunostaining of Tunel assay (red) and SOX10 (white) 1 day after WMS. Panel H) Image panel show high magnification fluorescent immunostaining of Tunel assay (red) and SOX10 (white) 1 day after WMS.

Figure 24:
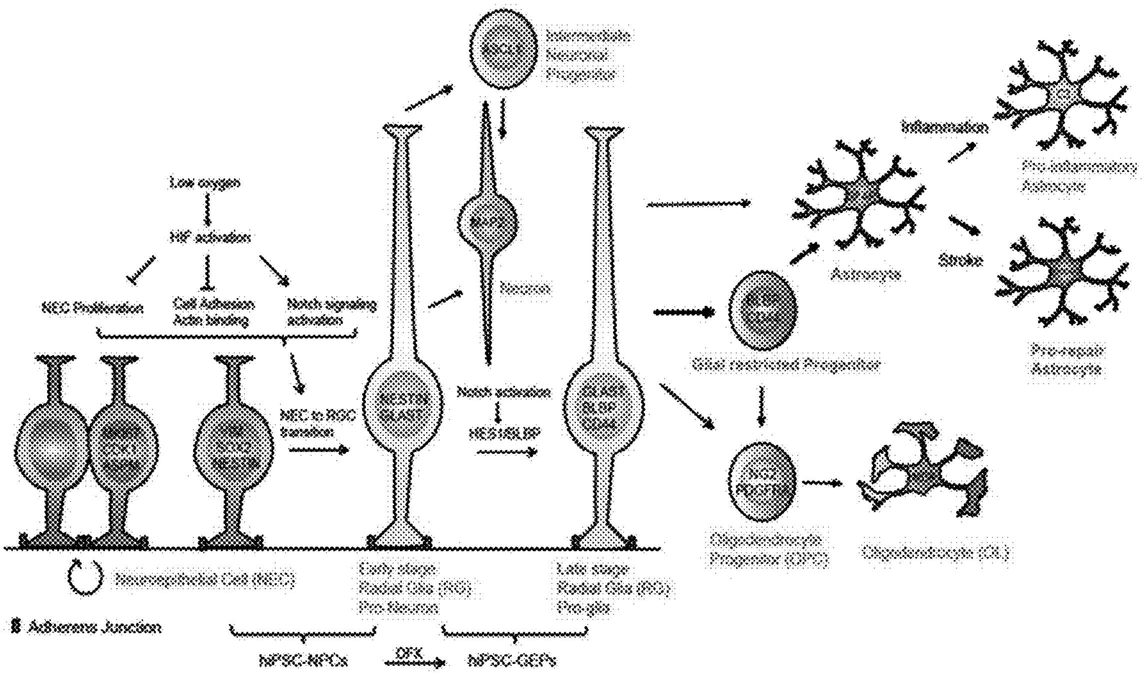

FIG. 24 illustrates cell types and signaling pathways involved in HIF pathway activation. Based on gene expression analysis and animal data, the hiPSC-NPCs represents NECs and early-stage pro-neuronal radial glia, whereas the hiPSC-GEPs are mostly composed of late-stage radial glia that are astrogliogenic. Upon transplantation in WMS animal, those hiPSC-GEPs tend to differentiate into pro-repair astrocytes, but not other cell types.

Figure 25:
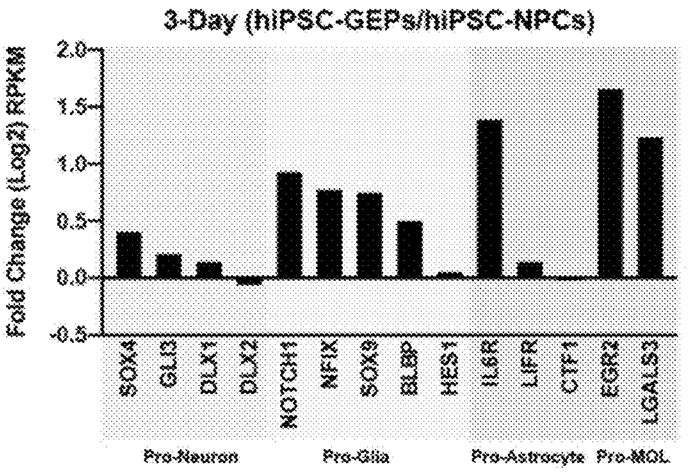
Figure 25:
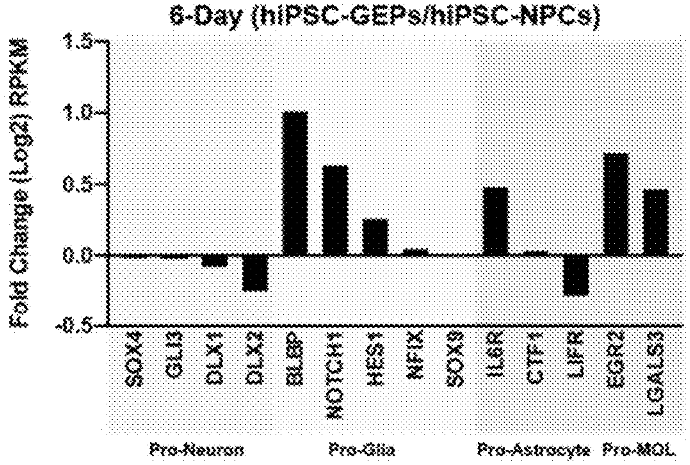
Figure 25:
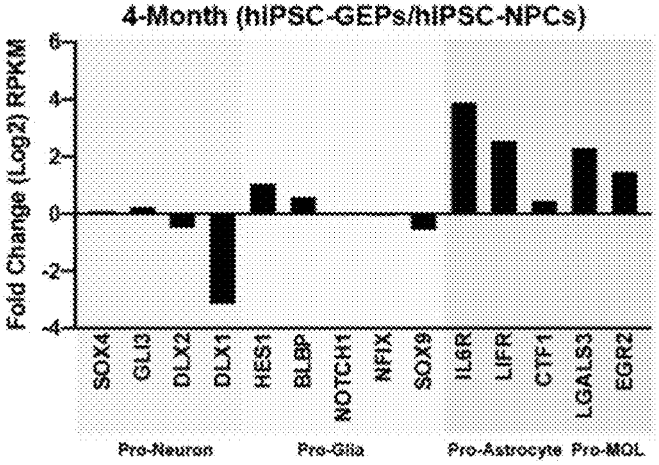

FIG. 25, panels A-C, illustrates transcription factors and signaling pathways involved in lineage specification at indicated time points. MOL: Myelinating oligodendrocyte.

Figure 26:
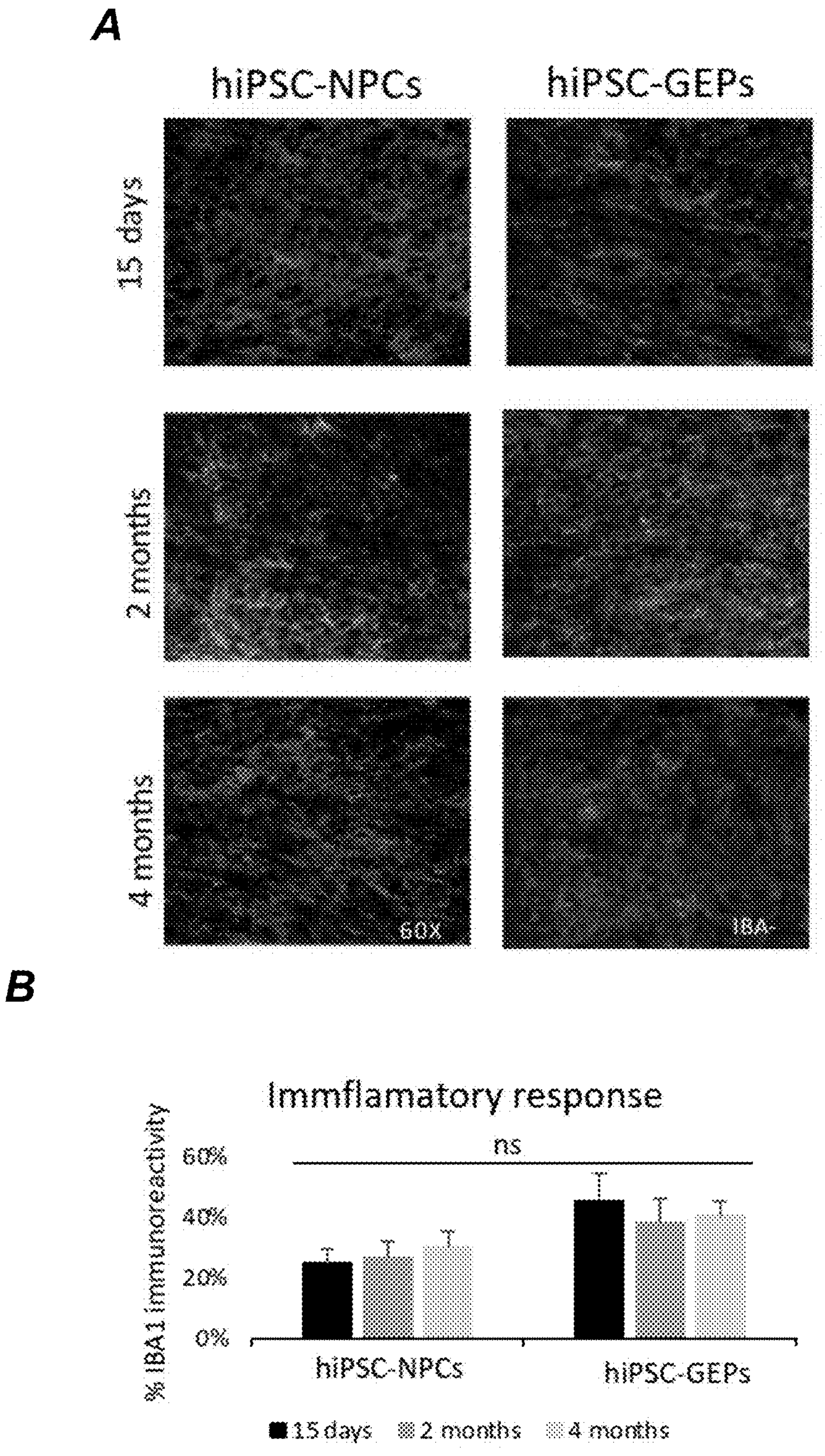

FIG. 26, panels A-B, illustrate microglial/immune cell activation after white matter stroke following hiPSC-NPCs or hiPSC-GEPs transplant. Panel A) Panels show relative microglial/immune cell activation 5 days, 2 and 4 months after hiPSC-NPCs or hiPSC-GEP transplant after WMS as determined by IBA-1 labeling (green) in the injured ipsilateral corpous callosum. Panel B) Quantification of microglial immune cells activated.

Figure 27:
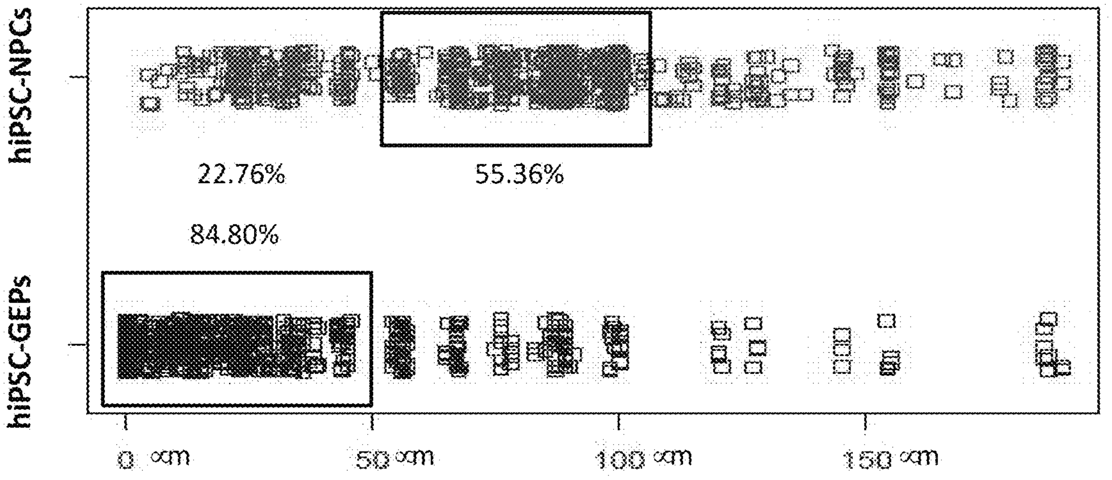
Figure 27:
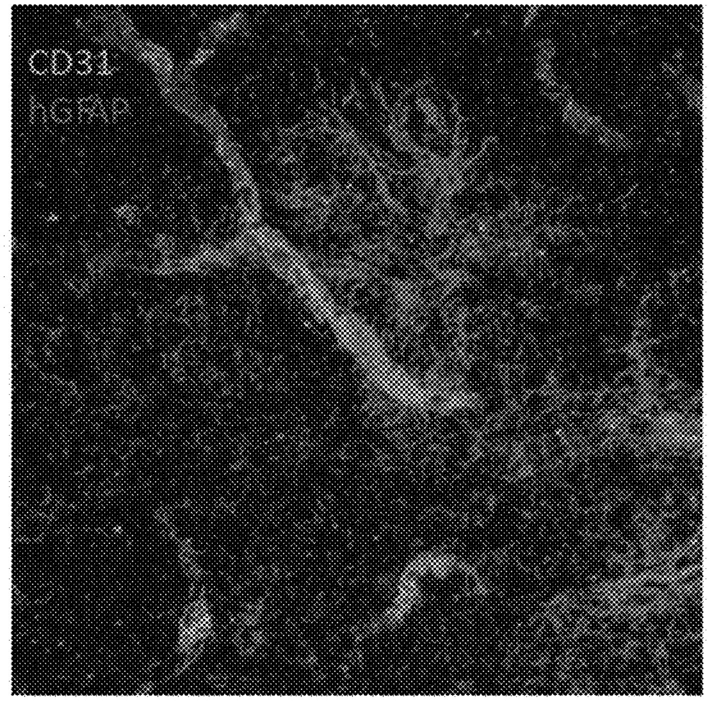

FIG. 27, panels A-B, shows that hiPSC-GEPs are intimately associated with cerebral vasculature. Panel A) Distance between the blood vessel to hiPSC-GEPs or hiPSC-NPCs quantification. Panel BV) Image panel shows fluorescent immunostaining of human GFAP+ cells (red) and CD31+ blood vessel (green) 4 months after stroke injury following hiPSC-GEP transplant.

Figure 28:
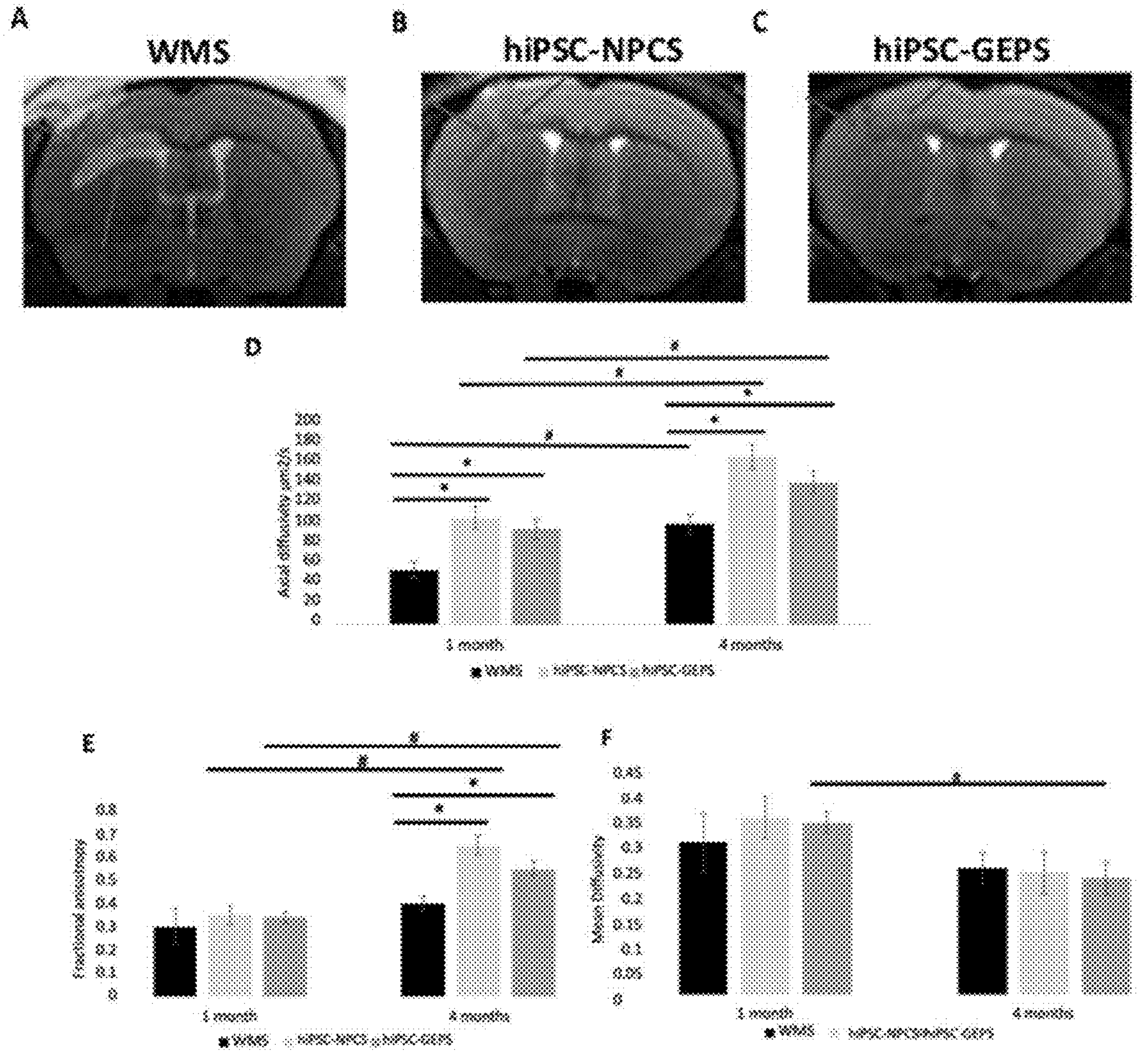

FIG. 28, panels A-F, illustrate brain imaging in white matter stroke. Panel A_Mouse MRI taken 1 month after L-NIO injections. Arrows denote hyperintensity caused by stroke. Panels B, C) MRI taken 1 month after L-NIO injections and hiPSC-NPCs or hiPSC-GEPs transplant. Arrows in panels B and C denote the apparent repair of damaged white matter due to the hiPSC-derived progenitor transplant. Panels D, E, and F) Quantitative DTI-tractography 1 and 4 months post-transplant (AD, FA, and MD).

Figure 29:
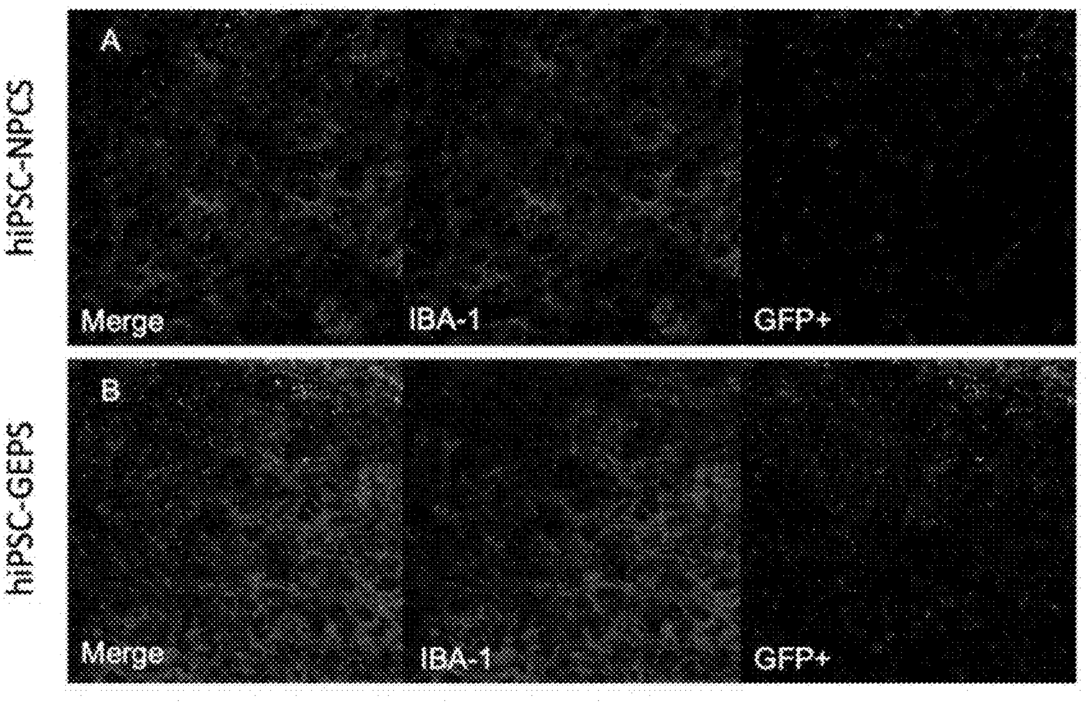

FIG. 29, panels A-B, illustrates DT-mediated hiPSC ablation. Panel A) Image panel showing fluorescent immunostaining of GFP+ cells (green), and IBA_1 (red) post-DT ablation 4 months after WMS following hiPSC-NPCs. Panel B) Image panel showing fluorescent immunostaining of GFP+ cells (green), and IBA-1 (red) post-DT ablation 4 months after WMS following hiPSC-GEP transplant.

DETAILED DESCRIPTION

In various embodiments, the methods and compositions described herein pertain to the discovery that iPS-GEP transplantation after cerebral ischemic injury enhances recovery in a murine model of WMS. Transplantation of iPS-GEP at subacute time points (e.g., 7 days after stroke) into the regions of the white matter stroke produced widespread migration of iPS-GEPs throughout subcortical white matter and resulted in increased myelination within the damaged white matter and reduced measures of reactive astrocytosis and inflammation. MRI imaging of white matter after transplantation of iPS-GEPs showed reduction in the hyperintensities that are characteristic of white matter damage in both the mouse model and human WMS. Behavioral evaluation demonstrated improvements in two tests of motor function. These results indicate that iPS-GEP transplantation promotes white matter repair and recovery in white matter stroke.

Accordingly, in various embodiments methods for the use of iPS-GEPs in the treatment of cerebral ischemic injury, such as white matter stroke are provided. Also provided herein are pharmaceutical compositions and formulations suitable for use in cell-based clinical therapy of white matter stroke.

Uses of Induced Pluripotent Glial-Enriched Progenitor Cells (iPSC-GEPs)

Derivation of glial-enriched progenitors (GEPs) from induced pluripotent stem cells, e.g., as described herein, provides a renewable and scalable source of GEPs for a number of important therapeutic, research, development, and commercial purposes, including, but not limited to treatment of cerebral ischemic injuries.

The term induced pluripotent glial-enriched progenitor cell (iPSC-GEP) refers to cells of a specific, characterized, in vitro differentiated cell population containing a mixture of astrocytes and other characterized cell types obtained from undifferentiated induced pluripotent stem cells according to the specific differentiation protocols described herein.

Compositional analysis of iPS-GEPs by immunocytochemistry (ICC), microarray analysis, and quantitative polymerase chain reaction (qPCR) demonstrates that the cell population is comprised primarily of neural lineage cells of the astrocyte and neuronal phenotype. Because of the method for generation of iPS-GEPs, substantially all cells in the culture are neural. This has been established because as part of the method, neural rosette structures are isolated manually and used to expand just neural derivatives. In addition, the method has been validated by immunostaining for various neural markers to determine identity. Finally, single-cell RT-PCR demonstrated that all cell express at least a subset of neural markers. There is no evidence that non-neural cells are present in these cultures.

As explained above, it was discovered that IPSGEPs can be used in the treatment, inter alia, of white matter stroke. The terms "treatment," "treat" "treated," or "treating," as used herein, can refer to both therapeutic treatment or prophylactic or preventative measures, where the goal is to prevent or slow down (lessen) an undesired physiological condition, symptom, disorder or disease, or to obtain beneficial or desired clinical results. In some embodiments, the term may refer to both treating and preventing. For the purposes of this disclosure, beneficial or desired clinical results may include, but are not limited to one or more of the following: alleviation of adverse symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response. Treatment also includes prolonging survival as compared to expected survival if not receiving treatment. In certain embodiments, particularly in the case of cerebral ischemia, treatment may include improving or restoring motor control, improving or restoring speech, improving or restoring balance, improving cognition (e.g., as measured by any of a variety of cognitive function assays), and the like.

The term "subject" and "patient" are used interchangeably herein and include, but are not limited to mammals such as humans, non-human primates, other mammals, e.g., a non-human primate, canine, equine, feline, porcine, bovine, lagomorph, and the like. In certain embodiments the subject is a subject identified as having a pathology characterized by demyelination, e.g., as described herein. In certain embodiments the subject is a subject determined to be at risk for a pathology characterized by demyelination of neural tissue in the central nervous system. Such characterization can be based on family history, previous instance of pathology in the subject, test results including, but not limited to, genetic tests identifying the subject as at risk for a demyelinating pathology, and the like. In some embodiments, the term "subject," refers to a male. In some embodiments, the term "subject," refers to a female.

In various embodiments the iPS-GEPs described herein promotes myelin repair and/or remyelination and/or slow demyelination in human patients or other subjects in need of therapy. The following are non-limiting examples of conditions, diseases and pathologies requiring myelin repair or remyelination: brain ischemic injuries including white matter stroke, multiple sclerosis, the leukodystrophies, the Guillain-Barre Syndrome, the Charcot-Marie-Tooth neuropathy, Tay-Sachs disease, Niemann-Pick disease, Gaucher disease, Hurler syndrome and traumatic injuries resulting in loss of myelination, such as acute spinal cord injury.

In certain embodiments, in addition to myelin repair or remyelination, iPS-GEPs can produce neurotrophic factors, e.g. BDNF, that may directly provide reparative action on the damaged tissue (e.g., ischemic tissue), such as GDF15, GDNF, VEGFa, TGFβ, and the like.

In various embodiments the iPS-GEPs are administered in a manner that permits them to reside at, and/or graft to, and/or migrate to the intended tissue site and reconstitute or regenerate the functionally deficient area, and/or to stabilize and/or prevent further degradation of neural tissue. Administration of the cells to a subject may be achieved by any method known in the art. For example, the cells may be administered surgically directly to the organ or tissue in need of a cellular transplant. Alternatively, non-invasive procedures may be used to administer the cells to the subject. Examples of non-invasive delivery methods include the use of syringes and/or catheters and/or cannula to deliver the cells into the organ or tissue in need of cellular therapy.

In certain embodiments, the iPS-GEPs are administered into the infarct core. In certain embodiments, the OPCs are additionally or alternatively administered adjacent to the infarct core. "Adjacent", as used herein, refers to the area outside the infarct core that in some instances represents an area of partial ischemic (e.g., stroke) damage. In certain embodiments "adjacent" refers to healthy tissue outside the infarct region. In some embodiments, the iPS-GEPs are administered from about 0.05 mm to about 3 mm from the infarct core. In some embodiments, the iPS-GEPs are administered from about 0.1 mm to about 2 mm from the infarct core. In some embodiments, the iPS-GEPs are administered from about 0.5 mm to about 1 mm from the infarct core. In some embodiments, the iPS-GEPs are administered from about 0.3 mm to about 0.6 mm from the infarct core.

In certain embodiments, the iPS-GEPs are administered to the subject during the subacute time period. "Subacute" as used herein refers to the time period between acute and chronic phases during which the initial damage and cell death from the ischemic (e.g., stroke) injury has ended. As used herein, "early subacute" in a human subject refers to up to one month after the stroke and "late subacute" refers to the time period 1-3 months after the stroke.

In certain embodiments, the subject receiving iPS-GEPs as described herein can be treated to reduce immune rejection of the transplanted cells. Methods of reducing immune rejection of cells and/or tissue are well known to those of skill in the art. Such methods include, but are not limited to, the administration of traditional immunosuppressive drugs such as tacrolimus, cyclosporin A, and the like (see, e.g., Dunn et al. (2001) Drugs 61: 1957), or inducing immunotolerance using a matched population of pluripotent stem derived cells (see, e.g., WO 02/44343; U.S. Pat. No. 6,280, 718; WO 03/050251). In certain embodiments, a combination of anti-inflammatory (such as prednisone or other steroidal anti-inflammatories) and immunosuppressive drugs may be used. In certain embodiments, the iPS-GEPs can be supplied in the form of a pharmaceutical composition, comprising an isotonic excipient prepared under sufficiently sterile conditions for human administration.

For general principles in medicinal formulation, the reader is referred to Allogeneic Stem Cell Transplantation, Lazarus and Laughlin Eds. Springer Science+Business Media LLC 2010; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the enriched target cells. Suitable ingredients may include matrix proteins that support or promote adhesion of the target cell type or that promote vascularization of the implanted tissue.

In certain embodiments iPS-GEPs are derived from the subject to be treated and are therefore not expected to be immunogenic when administered to the subject. In certain embodiments the cells are allogenic, e.g., derived from a subject other than the subject to be treated and possibly be immunogenic. In such instances it is possible to treat the subject with one or more immunosuppressants during administration of the iPS-GEPs and, optionally, for sometime thereafter. In certain embodiments administration of immunosuppressants continues for at least 30 days, or for at least 60 days, or for at least 90 days, or for at least 120 days, or for at least 150 days. Numerous immunosuppressants suitable for use in conjunction with step cell administration are known to those of skill in the art and include, but are not limited to cyclosporin, prednisone, and the like.

Another approach to mitigate immune responses is to generate iPS-GEPs from "universal donor cells" also known as "universal cells". Universal Cells addresses the allogeneic rejection problem by manipulating human leukocyte antigen (HLA) expression in stem cells. In conventional transplantation, multiple HLA class I and class II proteins must be matched for histocompatibility in allogeneic recipients. In universal cells the expression of these polymorphic HLA proteins is eliminated by gene editing, and the cells express specific non-polymorphic HLA molecules to provide essential class I signals that block lysis by Natural Killer (NK) cells. In certain embodiments suicide genes can be introduced for enhanced safety.

More specifically, HLA-A, B and C are polymorphic class I proteins expressed by most nucleated cells that must be matched for histocompatibility. The Beta-2 Microglobulin (B2M) gene encodes a common subunit essential for cell surface expression of all HLA class I heterodimers (the other subunits are the heavy chains for HLA-A, B, C, E, F, or G), so B2M−/− cells are class I-deficient. In certain embodiments, both B2M genes can be edited to create human pluripotent cells that lack polymorphic class I proteins. In certain embodiments these editing steps can, optionally, also introduce suicide gene(s) such as thymidine kinase (TK) to allow for in vivo elimination of transplanted cells.

A complete lack of class I expression can lead to lysis by Natural Killer (NK) cells. To overcome this "missing self" response, the universal donor cells can be engineered to express a non-polymorphic class I gene such as HLA-E at the B2M locus. This provides a class I-positive signal to inhibit NK cells. These class I-engineered stem cells can serve as universal donor cells in applications where the differentiated cell product does not express HLA class II.

HLA class II molecules are expressed on antigen presenting cells such as dendritic cells, macrophages and B cells, and many other cell types upregulate their expression in response to inflammation and other signals. HLA class II proteins lack a common subunit that can readily be edited to prevent surface expression. Accordingly, in certain embodiments, one of the four transcription factor genes required for all class II gene expression (CIITA, RFXANK, RFX5, RFXAP) can be edited. Combining class I and class II engineering creates universal donor stem cell lines that are appropriate for deriving many differentiated cell products.

Methods for generating universal donor cells are well known to those of skill in the art and described for example, in PCT Publication No: WO/2016/183041 A3. in U.S. Patent Publication Nos: US 2019/0381154, US 2019/0365876, US 2015/0056225, US 2014/0134195, and the like.

Production of Induced Pluripotent Glial-Enriched Progenitor Cells (iPSC-GEPs)

Methods of generating induced pluripotent stem cells (IPSCs) are known to those of skill in the art. The original method of reprogramming murine fibroblasts by Takahashi and Yamanaka (2006) Cell 126: 663-676 utilized retroviral transduction of Oct4, Sox2, Klf4, and c-myc into mouse embryonic fibroblasts (MEFs) or tail-tip fibroblasts (TTF) derived from mice expressing β-galactosidase-neomycin fusion protein at the Fbx15 locus, which is specifically expressed in pluripotent stem cells and serves as an excellent marker for pluripotency. Drug selection with G418 after transduction of the four factors resulted in reprogramming of 0.02% of the MEFs or TTFs 14-21 days post-transduction. Reprogramming of adult human dermal fibroblasts (HDFs) was first reported to occur at an efficiency of ~0.02% at ~30 days after transducing the four reprogramming factors (Takahashi et al. (2007) *Cell.* 131: 861-872)

In various embodiments a lentiviral expression system can be employed to deliver Oct4, Sox2, Nanog, and Lin28 to fibroblasts (Yu et al. (2007) *Science,* 318: 1917-1920) and single cassette reprogramming vectors have been developed using, e.g., Cre-Lox mediated transgene excision (see, e.g., Papapetrou et al. (2009) *Proc. Natl. Acad. Sci. USA,* 106: 12759-12764; Carey et al. (2009) *Proc. Natl. Acad. Sci. USA,* 106: 157-162; Chang et al. (2009) *Stem Cells* 27: 1042-1049; Sommer et al. (2009) *Stem Cells,* 27:543-549; Soldner et al. (2009) *Cell* 136: 964-977). Other viral systems can also be used for reprogramming. Such systems include, but are not limited to adenovirus systems (see, e.g., Stadtfeld et al. (2008) *Science,* 322: 945-949; Zhou and Freed (2009) *Stem Cells* 27: 2667-2674, etc.), and sendai virus systems (see, e.g., Fusaki et al. (2009) *Proc. Jpn. Acad. Ser. B Phys. Biol. Sci.* 85: 348-362; Seki et al. (2010) *Cell Stem Cell.* 7: 11-14; Ban et al. (2011) *Proc. Natl. Acad. Sci. USA,* 108: 14234-14239). Reprogramming has also been accomplished using mRNA transfection (see, e.g., 19), miRNA infection/transfection (see, e.g., Subramanyam et al. (2011) *Nat. Biotechnol.* 29: 443-448; Anokye-Danso et al. (2011) *Cell Stem Cell* 8: 376-388), PiggyBac, mobile genetic element (transposon) that in the presence of a transposase can be integrated into chromosomal TTAA sites and subsequently excised from the genome footprint-free upon re-expression of the transposase (see, e.g., Kaji et al. 92009) *Nature* 458: 771-775; Woltjen et al. (2009) *Nature* 458: 766-770), mini-circle vectors (see, e.g., Narsinh et al. (2011) *Nature Protoc.* 6: 78-88), episomal plasmids (Okita et al. (2008) *Science* 322: 949-953; Yu et al. (2007) *Science* 318: 1917-1920; Huet al. (2011) *Blood* 117: e109-e119), oriP/EBNA vectors (31, 32), and the like.

One suitable method for fast and efficient induction of glial-enriched progenitor cells from human iPS cells has recently been described by Xie et al. (2014) *Stem Cell Reports* 3: 743-757). This technique utilizes changes in oxygen tension in the cell culture medium, or its downstream oxygen signaling molecules—the hypoxia-inducing factor (Hif) system. Treatment with deferoxamine, an inducer of Hif, produces a lasting restriction of the differentiation potential of iPS-NPCs to more of an astrocyte fate (Id.). This approach establishes a protocol that can serve to produce efficient induction of a glial-enriched precursor cell for transplantation as a therapy for WMS.

The production of suitable IPS-GEPs is illustrated below in the materials and methods. These methods are intended to be illustrative and non-limiting. Using the teachings provided herein other methods of generating suitable ISP-GEPs will be available to one of skill in the art.

Pharmaceutical Compositions

In certain embodiments the induced pluripotent glial-enriched progenitor cells (iPSC-GEPs) may be administered to a subject in need of therapy per se. Alternatively, the cells may be administered to the subject in need of therapy in a pharmaceutical composition mixed with a suitable carrier and/or using a depot delivery system.

As used herein, the term “pharmaceutical composition” refers to a preparation comprising a therapeutic agent or therapeutic agents in combination with other components, such as physiologically suitable carriers and excipients.

As used herein, the term “therapeutic agent” refers to the cells described herein (e.g., induced pluripotent glial-enriched progenitor cells (iPSC-GEPs) or IPC-NPCs) accountable for a biological effect in the subject. Depending on the embodiment “therapeutic agent” may refer to the IPSC-GEPs and/or IPC-NPCs described herein. Additionally or alternatively, “therapeutic agent” may refer to one or more factors secreted by the IPSC-GEPs in aiding neural repair.

As used herein, the term “therapeutically effective amount” means a dosage, dosage regimen, or amount sufficient to produce a desired result.

As used herein, the terms “carrier” “physiologically acceptable carrier” and “biologically acceptable carrier” may be used interchangeably and refer to a diluent or a carrier substance that does not cause significant adverse effects or irritation in the subject and does not substantially abrogate the biological activity or effect of the therapeutic agent. The term “excipient” refers to a substance added to a pharmaceutical composition to further facilitate administration of the therapeutic agent.

In certain embodiments the compositions contemplated herein (e.g. formulations containing IPSC-GEPs) can be formulated for parenteral administration by injection, e.g., by bolus injection or continuous infusion. In certain embodiments the compositions can be administered by continuous infusion subcutaneously over a period of about 15 minutes to about 24 hours. In certain embodiments formulations for injection can be presented in unit dosage form, e.g., in ampoules or in multi-dose containers, optionally with an added preservative. The compositions can take such forms as suspensions, solutions or emulsions in oily or aqueous vehicles, and can contain formulatory agents such as suspending, stabilizing and/or dispersing agents.

In certain embodiments the progenitor cells (e.g., IPSC-GEPs) described herein can be administered (e.g., injected, perfused, etc.) suspended in a buffer. Suitable buffers are known to those of skill in the art. One illustrative, but non-limiting buffer is ISOLYTE® S plus 25% human serum albumin (HAS). ISOLYTE® S (multi-electrolyte injection solution) contains in 100 mL sodium chloride USP 0.53 g; sodium gluconate USP 0.5 g, sodium acetate trihydrate USP 0.37 g; potassium chloride USP 0.037 g, magnesium chloride hexahydrate USP 0.03 g, water for injection USP qs, and is pH adjusted with glacial acetic acid USP pH: 6.7 (6.3-7.3) with a calculated osmolarity of about 295 mOsmol/liter. This buffer is illustrative and non-limiting. Numerous other suitable injection buffers will be known to those of skill in the art.

In certain embodiments the progenitor cells (e.g., IPSC-GEPs) described herein can be provided in implantable sustained delivery systems. Implantable sustained delivery systems are known to those of skill in the art. Such systems include, but are not limited to, mechanical and/or electronic devices such as implantable drug pumps or microchip systems as well as implantable controlled delivery polymeric matrices.

Implantable microchip systems, include systems such as the MICROCHIPS® device (MICROCHIPS®, Inc. Bedford MA). The MICROCHIPS® implantable drug delivery system (IDDS) is based on a microfabricated silicon chip that contains multiple drug-filled reservoirs. The chip is attached to a titanium case containing a battery, control circuitry, and telemetry. The drug chip and titanium case are hermetically sealed and electrically linked by a ceramic substrate with metal interconnects. The IDDS communicates with an external handheld controller through wireless transmission. A drug regimen can be transmitted to the implanted device through this link, allowing reservoirs to be opened at prescribed times without any need for further communication. Alternatively, reservoirs can be opened as desired on command from the controller.

Controlled release polymeric devices can be made for long term release following implantation. Illustrative controlled polymeric release devices comprise an implantable rod, cylinder, film, disk, and the like, or an injectable polymeric formulation (e.g. a microparticle formulation). In various embodiments the implantable matrix can be in the form of microparticles such as microspheres, where the IPSC-GEPs are dispersed within a solid polymeric matrix or microcapsules. Typically in such systems the core is of a different material than the polymeric shell, and the active agent (e.g., IPSC-GEPs) will be dispersed or suspended in the core, which may be liquid or solid in nature. Alternatively, the polymer may be cast as a thin slab or film, or even a gel such as a hydrogel.

In certain embodiments either non-biodegradable or biodegradable matrices can be used for delivery of progenitor cells as described herein, however, in certain embodiments biodegradable matrices are typically preferred. These can include natural or synthetic polymers. Often synthetic polymers provide better characterization of degradation and release profiles. The polymer is typically selected based on the period over which release is desired. In some cases, linear release may be most useful, although in others a pulse release or "bulk release" may provide more effective results. As discussed below, in certain embodiments, the polymer is in the form of a hydrogel, and can optionally be crosslinked with multivalent ions or polymers.

In various embodiments the matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer (1987) *J. Controlled Release* 5:13-22; Mathiowitz, et al. (1987) *Reactive Polymers* 6: 275-283, Mathiowitz, et al. (1988) *J. Appl. Polymer Sci.* 35:755-774, and the like.

In various embodiments the devices can be formulated for local release to treat the area of implantation, e.g., the infarct cavity. In various embodiments these can be implanted or injected into the desired region.

In certain embodiments the implantable the depot delivery systems comprise microparticles patterned within a hydrogel. In one illustrative embodiment, the progenitor cells are provided within or mixed with microparticles (e.g., PLGA microparticles) entrapped within a hydrogel (e.g., PEG hydrogel) base. Such systems have been constructed to deliver agents with two different delivery profiles (see, e.g., Wang et al. (2011) *Pharmaceutical Res.*, 28(6): 1406-1414).

In certain embodiments the progenitor cells described herein can be administered as a component of a hydrogel, such as those described in U.S. patent application Ser. No. 14/275,795, filed May 12, 2014, and U.S. Pat. Nos. 8,324,184 and 7,928,069. Hydrogels comprising synthetic polymers such as poly (hydroxyethyl methacrylate) (PHEMA), poly-(ethylene glycol) (PEG) and poly (vinyl alcohol) (PVA) and/or comprising naturally sourced material such as collagen, hyaluronic acid (HA), fibrin, alginate, agarose and chitosan are known in the art (see, e.g., Peppas et al. (2006) *Advanced Materials* 18:1345; Lee et al. (2001) *Chem. Rev.* 101:1869). Covalently cross-linked hydrogels formed by various chemical modifications have also been previously described (see, e.g., Vercruysse et al. (1997) *Bioconjugate Chem.* 8:686; Prestwich et al. (1998) *J. Controlled Release* 53:93; Burdick et al. (2005) *Biomacromolecules* 6:386; Gamini et al. (2002) *Biomaterials* 23:1161; U.S. Pat. Nos. 7,928,069; 7,981,871).

Hydrogels based on thiol-modified derivatives of hyaluronic acid (HA) and gelatin cross-linked with polyethylene glycol diacrylate (PEGDA) (trade name HYSTEM®) have unique chemical, biological and physical attributes making them suitable for many applications including cell culture, drug delivery and the like (see, e.g., Shu et al. (2004) *J of Biomed Mat Res Part A* 68:365; Shu et al. (2002) *Biomacromolecules* 3:1304; Vanderhooft et al. (2009) *Macromolecular Biosci* 9:20). Cross-linked HA hydrogels, including HYSTEM®, have been successfully used in animal models of corneal epithelial wound healing (see, e.g., Yang et al. (2010) *Veterinary Opthal* 13:144, corneal tissue engineering (Espandar et al. (2012) *Arch. Opthamol* 130: 202, and retinal repair Liu et al. (2013) *Tissue Engineering Part A* 19:135).

The preclinical use of hydrogels to maintain bioactivity and slow release of biologics has been described (Cai et al. (2005) *Biomaterials* 26:6054; Zhang (2011) *Biomaterials* 32:9415; Overman et al. (2012) *Proceedings of the National Academy of Sciences of the United States of America* 109: E2230; Garbern et al. (2011) *Biomaterials* 32:2407; Koutsopoulos et al. (2009) *Proceedings of the National Academy of Sciences of the United States of America* 106:4623. Furthermore, their use in cell delivery has been shown to improve cell viability and localization post-implantation (Laflamme et al. (2007) *Nature Biotechnology* 25:1015; Zhong et al. (2010) *Neurorehabilitation and Neural Repair* 24:636; Compte et al. (2009) *Stem Cells* 27:753. Several different hydrogels have been used as excipients in FDA-approved ocular small molecule therapeutics to increase their residence time on the eye surface (see, e.g., Kompella et al. (2010) *Therapeutic Delivery* 1:435).

In addition, two new hydrogel formulations have been reported that show promise in delivering therapeutic cells (see Ballios et al. (2010) *Biomaterials,* 31:2555; Caicco et al. (2012) *J. Biomed. Mate. Res. PartA* 101:1472; Yang et al. (2010) *Veterinary ophthalmology* 13:144; Mazumder et al. (2012) *J. Biomed. Mat. Res. Part A* 100:1877.

These formulations and protocols are intended to be illustrative and non-limiting. Using the teachings provided herein, other suitable hydrogel formulations will be available to one of skill in the art.

Illustrative Methods and Materials

Animal Subjects.

All procedures used were approved by the UCLA Chancellor's Animal Research Committee and were conducted in accordance with the National Institute of Health Guide for the Care and Use of Laboratory Animals. NSG mice (Shultz et al. (2007) *Nat. Rev. Immunol.* 7(20): 118; jaxmice.jax.org/nod-scid-gamma) were obtained from Jackson Laboratories (Bar Harbor, ME). All animal subjects were housed in standard conditions with a 12 hr light/dark cycle and were provided food and water ad libitum.

Induction of Focal Ischemic Lesions Using L-Nio.

Figure 2:
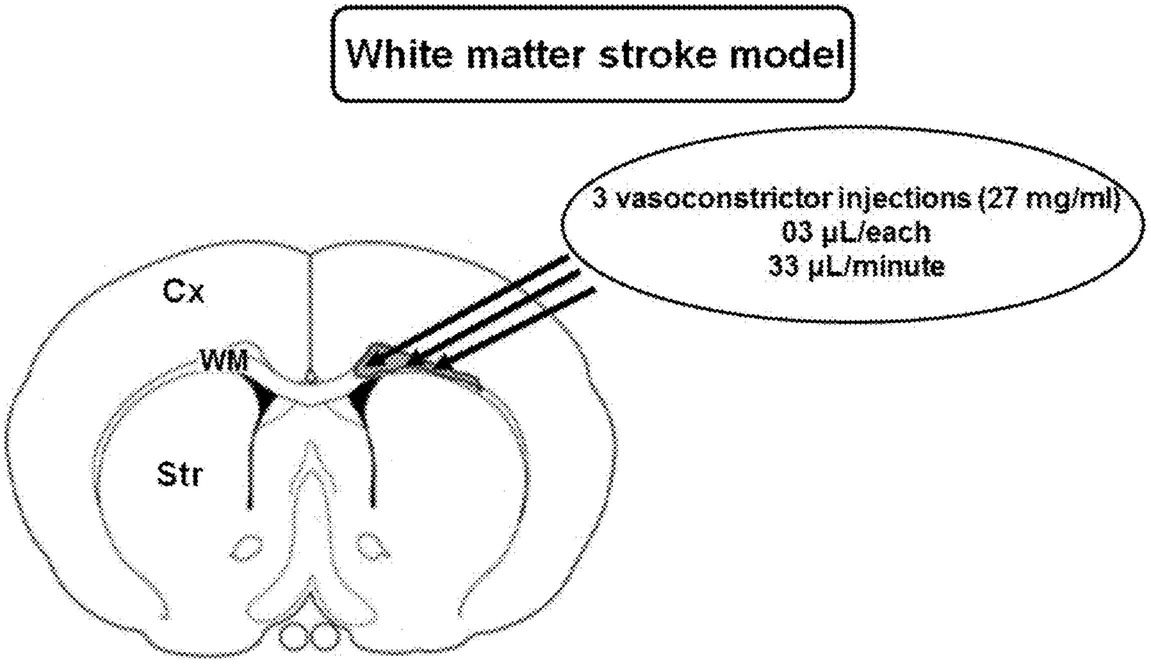
FIG. 2 is a diagram of coronal mouse brain section indicating injection sites of L-NIO. Blue arrows indicated the three injection sites of L-NIO, delivered at an angle of 36° directly into the corpus callosum of each mouse brain to induce a focal ischemic lesion. Abbreviations: Cx=cortex; Str=striatum; WM J=white matter.
Figure 3:
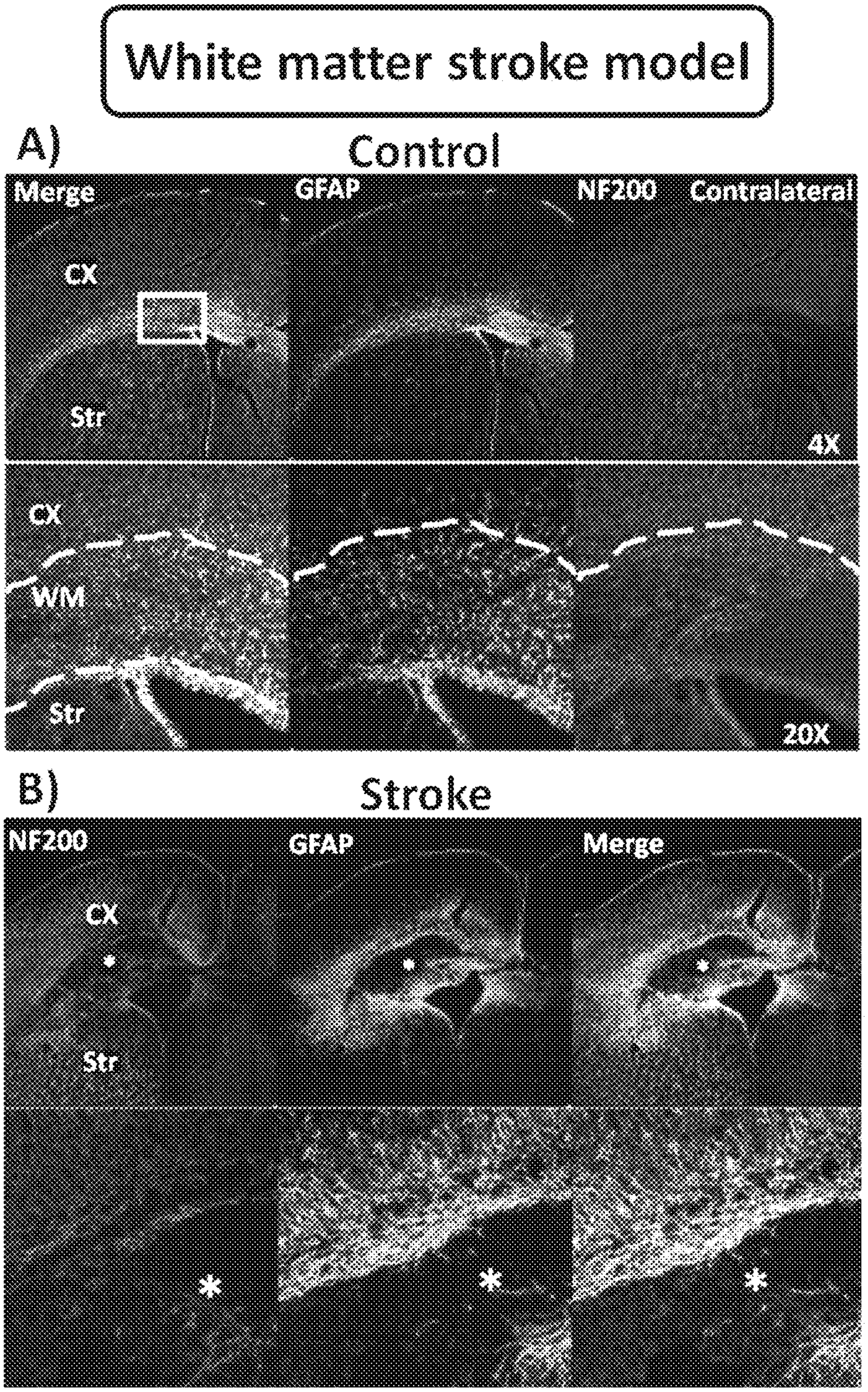
FIG. 3, panels A-B, shows representative fluorescent photomicrographs of astrocyte activation and axonal loss in the stroke-injured mouse brain. Image panels show fluorescent immunostaining of astrocytes (GFAP) and axons (NF200) three weeks after stroke injury in the uninjured contralateral hemisphere (A, control) and stroke-injured hemisphere (B, white matter stroke). In (A), the left column depicts the merged fluorescent image for GFAP and NF200, the middle column depicts GFAP alone, and the right column depicts NF200 alone. In (B), the left column depicts NF200 alone; the middle column depicts GFAP alone, and the right column depicts the merged fluorescent image for GFAP and NF200. For (A) and (B), the rows show increasing levels of magnification for the lesioned area (B) and contralateral side (A). Top rows=40×, middle rows=200×, bottom. White boxes in (A) indicate the regions magnified in lower panels. The white dotted lines in (A) indicate the approximate borders of the corpus callosum. The asterisks in (A) and (B) indicate the lateral ventricle. Abbreviations: Cx=cortex; GFAP=glial fibrillary acid protein; NF200=neurofilament 200; Str=striatum; WM=white matter.
Figure 4:
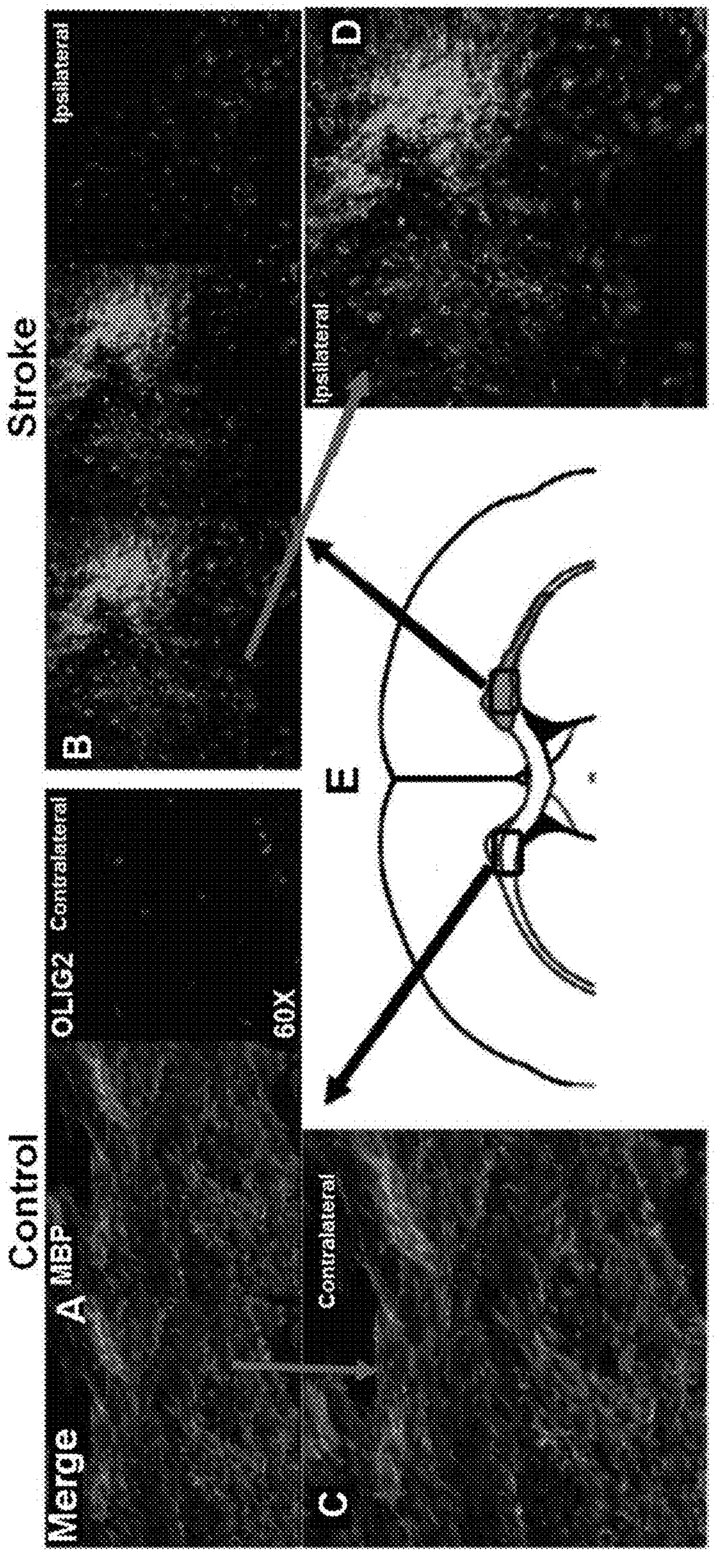
FIG. 4, panels A-F, shows representative fluorescent photomicrographs of myelin loss and oligodendrocyte response in the stroke-injured mouse brain. Relative myelin loss (MBP, green) and oligodendrocyte presence (OLIG2, red) three weeks after stroke injury in the uninjured contralateral corpus callosum (A)-(B), and the injured ipsilateral corpus callosum (C)-(D). For (A) and (B), left panel shows merged image for MBP and OLIG2, middle panel shows MBP alone, and right panel shows OLIG2 alone. Panels (C) and (D) show higher magnification images of the merged images in (A) and (C). (E) Diagram of coronal mouse brain section showing regions depicted in (A)-(D). Magnifications: (A) and (B)=600×; (C) and (D)=1000×. Abbreviations: MBP=myelin basic protein. Panel F shows quantification of myelin basic protein immunoreactivity and oligodendrocyte response within the corpus callosum lesion following stroke injury and iPSC-NPCs or iPSC-GEPs transplantation. Panel E (top) Mean myelin basic protein (MBP) immunoreactivity is shown for each treatment group at 3 weeks post-stroke (or sham surgery). Panel E (bottom) The average number of OLIG2 positive cells is shown for each treatment group at 3 weeks post-stroke (or sham surgery). Error bars denote standard error of the mean.
Figure 5:
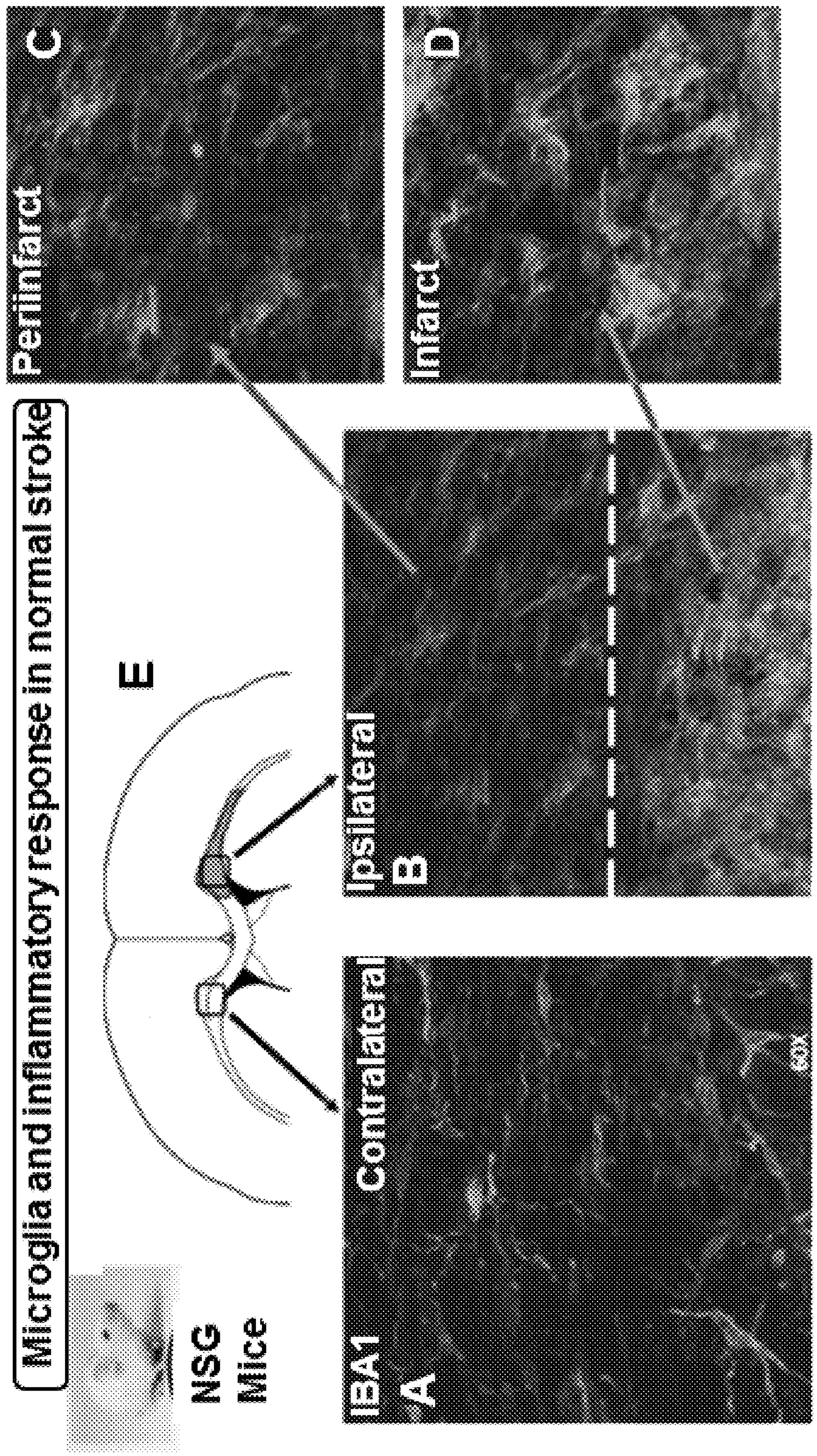
FIG. 5, panels A-E, shows representative fluorescent photomicrographs of activated microglia/immune cells in the stroke-injured mouse brain. (A) Diagram of coronal mouse brain section indicating the regions shown in (B)-(D). (B)-(D) Relative microglial/immune cell activation three weeks after stroke injury as determined by Iba1 labeling (purple) in the uninjured contralateral corpus callosum (B), and the injured ipsilateral corpus callosum (C)-(E). Panels (D) and (E) shown higher magnification images of the regions indicated in (C). Dotted white line in (C) indicates the approximate border between infarct core and peri-infarct tissue. Magnification: (B) and (C)=600×; (D) and (E)=1000×. Abbreviations: Iba1=ionized calcium-binding adapter molecule 1.
Figure 6:
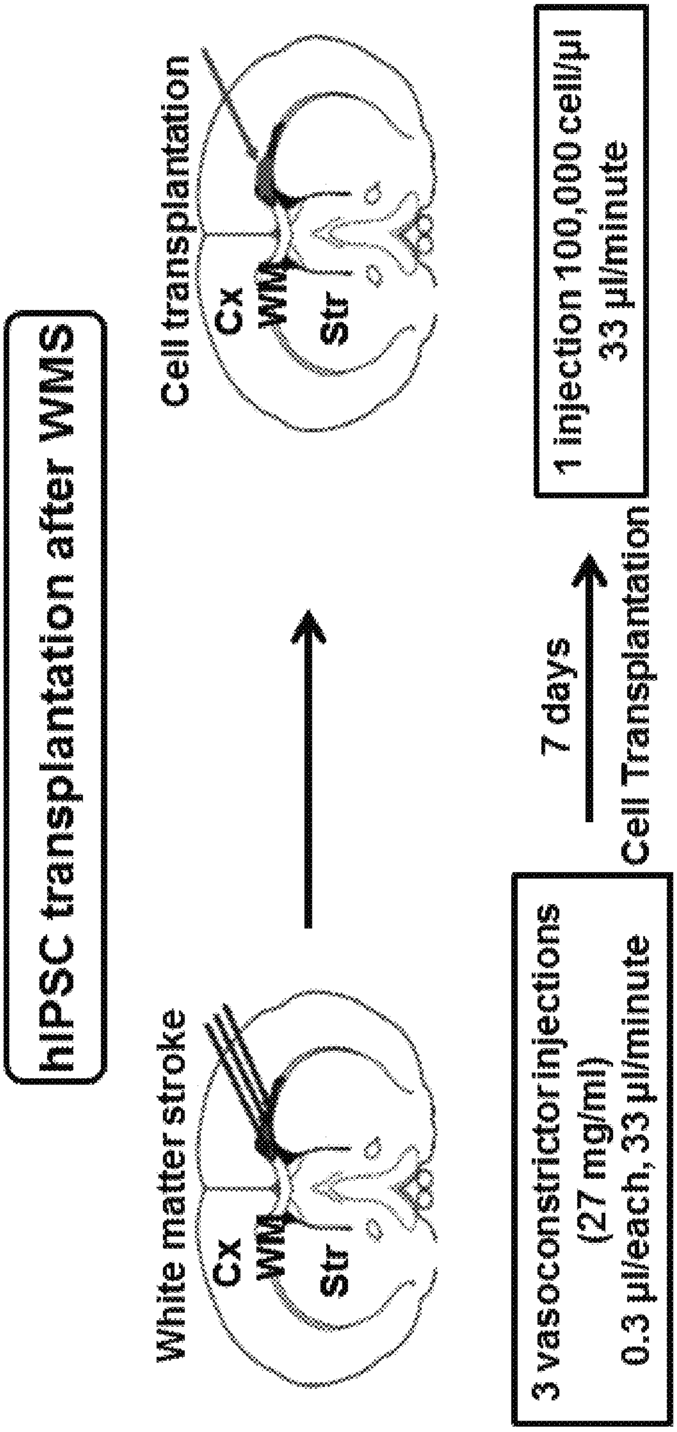
FIG. 6 is a diagram of coronal mouse brain section indicating cell injection site into the uninjured corpus callosum. Arrow indicates approximate cell injection site within the uninjured corpus callosum. Abbreviations; Cx=cortex; Str=striatum; WM=white matter.
Figure 7:
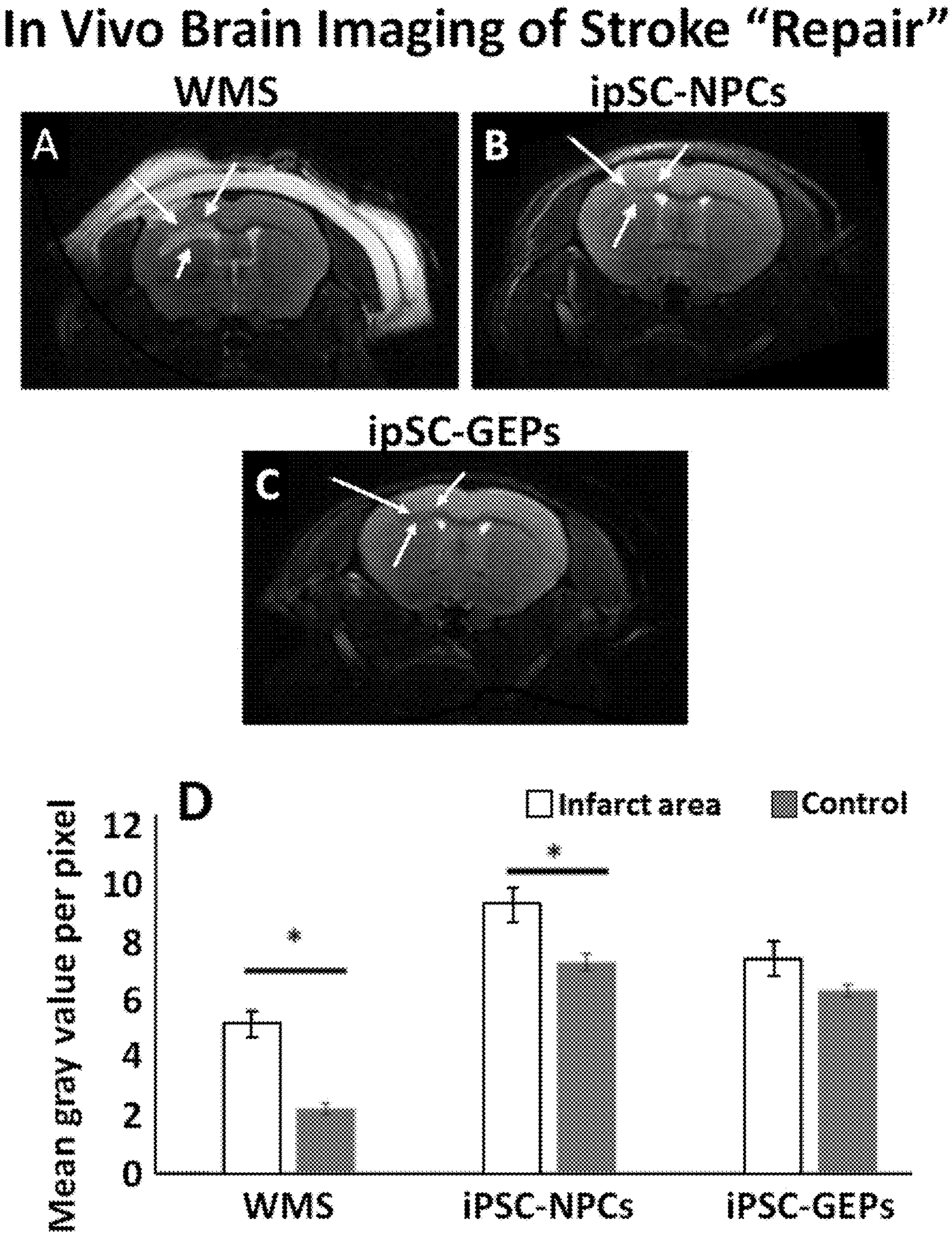
FIG. 7, panels A-D, illustrates mouse subcortical white matter stroke and cell transplantation. (A) Mouse MRI taken 1 month after L-NIO injections. Arrows denote hyperintensity caused by stroke. (B) MRI taken 1 month after L-NIO injections and iPSC-NPCs transplantation. (C) MRI taken 1 month after L-NIO injections and iPSC-GEPs transplantation. Arrows in B and C denote the apparent repair of damaged white matter due to the iPSC transplantation. Panel D shows the mean gray value per pixel: This is the sum of the gray values of all the pixels in the selection divided by the number of pixels. Reported in calibrated units, measured on the contralateral (uninjured) and the ipsilateral (injured) side of the mouse brain in the different treatment groups. Error bars denote standard error of the mean. Asterisk indicate significance relative to the uninjured side of the brain using two-way ANOVA with Tukey's HSD post-hoc analysis ($p<0.05$).
Figure 8:
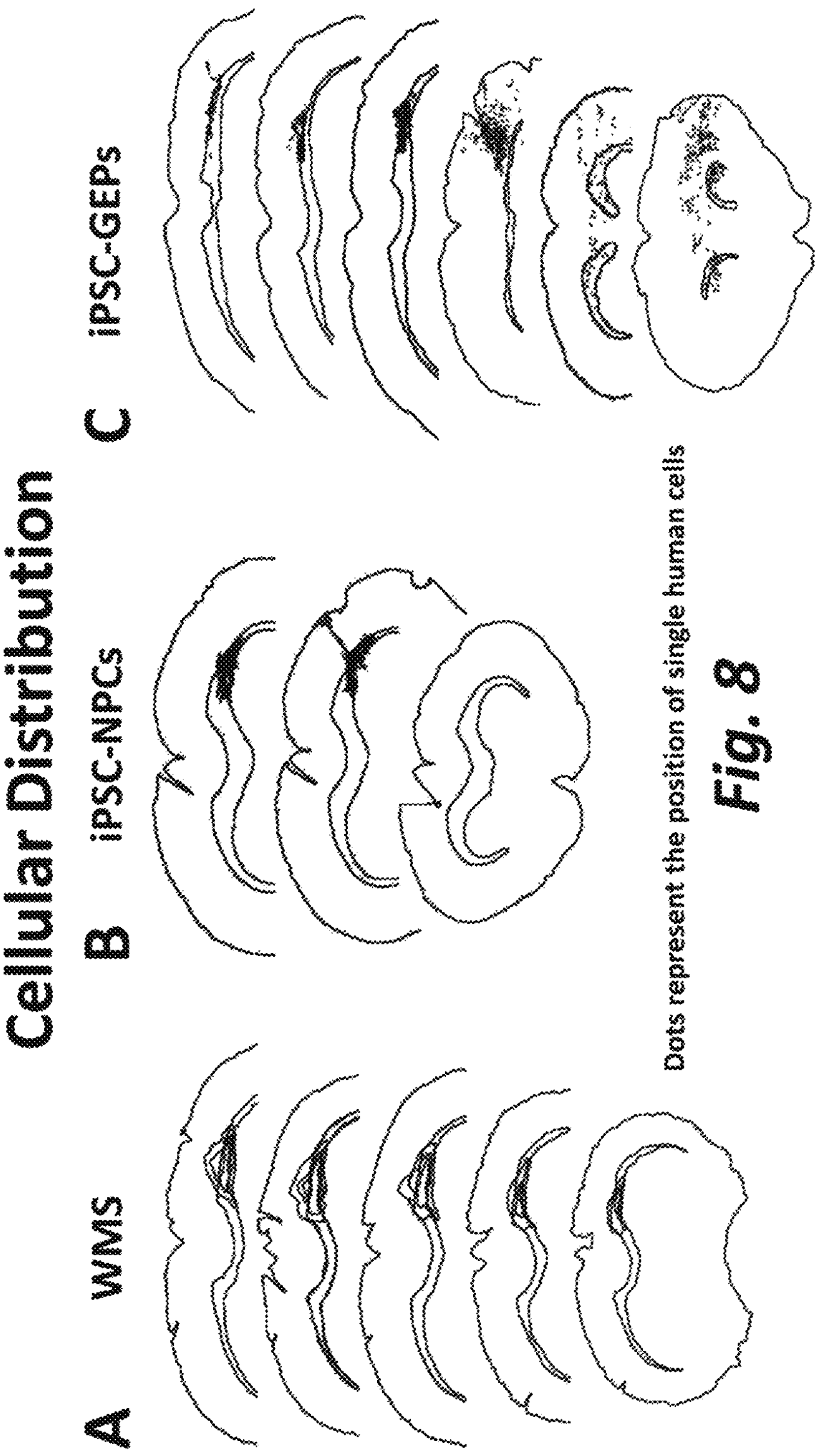
FIG. 8, panels A-C, represents mouse coronal sections indicating the infarct area region, the position IPS-NPCs and the position of iPS-GEPs. Dots represent the position of single human cells. (A) Represent mouse coronal sections indicating the infarct area region. (B) Represent mouse coronal sections indicating the position of iPS-NPCs after 2 months of transplantation. (C) Represent mouse coronal sections indicating the position of iPS-GEPs after 2 months of transplantation. Abbreviations: WMS=white matter stroke; iPSC-NPCs=induced pluripotent stem cells neuronal progenitor cells; iPSC-GEPs=induced pluripotent stem cells glial enriched progenitor cells.
Figure 9:
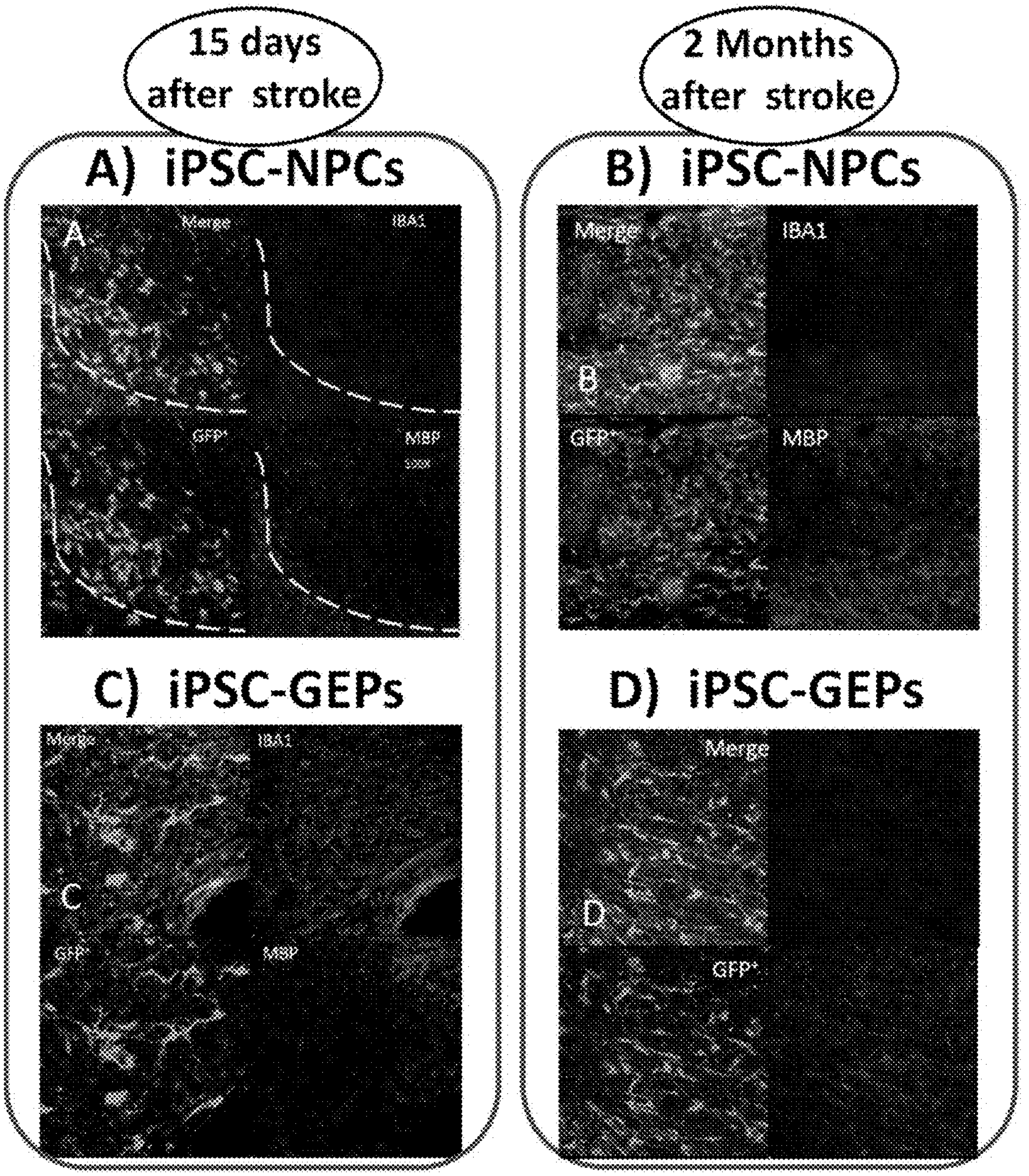
FIG. 9, panels A-D, shows representative fluorescent photomicrographs of iPSC-NPCs or iPSC-GEPs location, activated microglia/immune cells and MBP response in the mouse brain following stroke injury. Image panels show fluorescent immunostaining of GFP+ cells (green), activated microglia/immune cells (IBA-1, blue) and MBP (red) 2 and 8 weeks after stroke injury following iPSC-NPCs or iPSC-GEPs transplantation. In A, panel 1 (left top) depicts the merged fluorescent image for GFP+, MBP and IBA1, panel 2 (right top) depicts IBA-1 alone, panel 3 (left bottom) depicts GFP+ alone, and panel 4 (right bottom) depicts MBP alone after 2 weeks of IPS-NPCs transplantation. In B, panel 1 (left top) depicts the merged fluorescent image for GFP+, MBP and IBA1, panel 2 (right top) depicts IBA-1 alone, panel 3 (left bottom) depicts GFP+ alone, and panel 4 (right bottom) depicts MBP alone after 8 weeks of IPS-NPCs transplantation. In C, panel 1 (left top) depicts the merged fluorescent image for GFP+, MBP and IBA1, panel 2 (right top) depicts IBA-1 alone, panel 3 (left bottom) depicts GFP+ alone, and panel 4 (right bottom) depicts MBP alone after 2 weeks of IPS-GEPs transplantation. In D, panel 1 (left top) depicts the merged fluorescent image for GFP+, MBP and IBA1, panel 2 (right top) depicts IBA-1 alone, panel 3 (left bottom) depicts GFP+ alone, and panel 4 (right bottom) depicts MBP alone after 8 weeks of IPS-GEPs transplantation. Magnification=600×. Abbreviations: MBP=myelin basic protein; IBA-1=ionized calcium-binding adapter molecule; iPSC-GEPs=induced pluripotent stem cells glial enriched progenitor cells.
Figure 10:
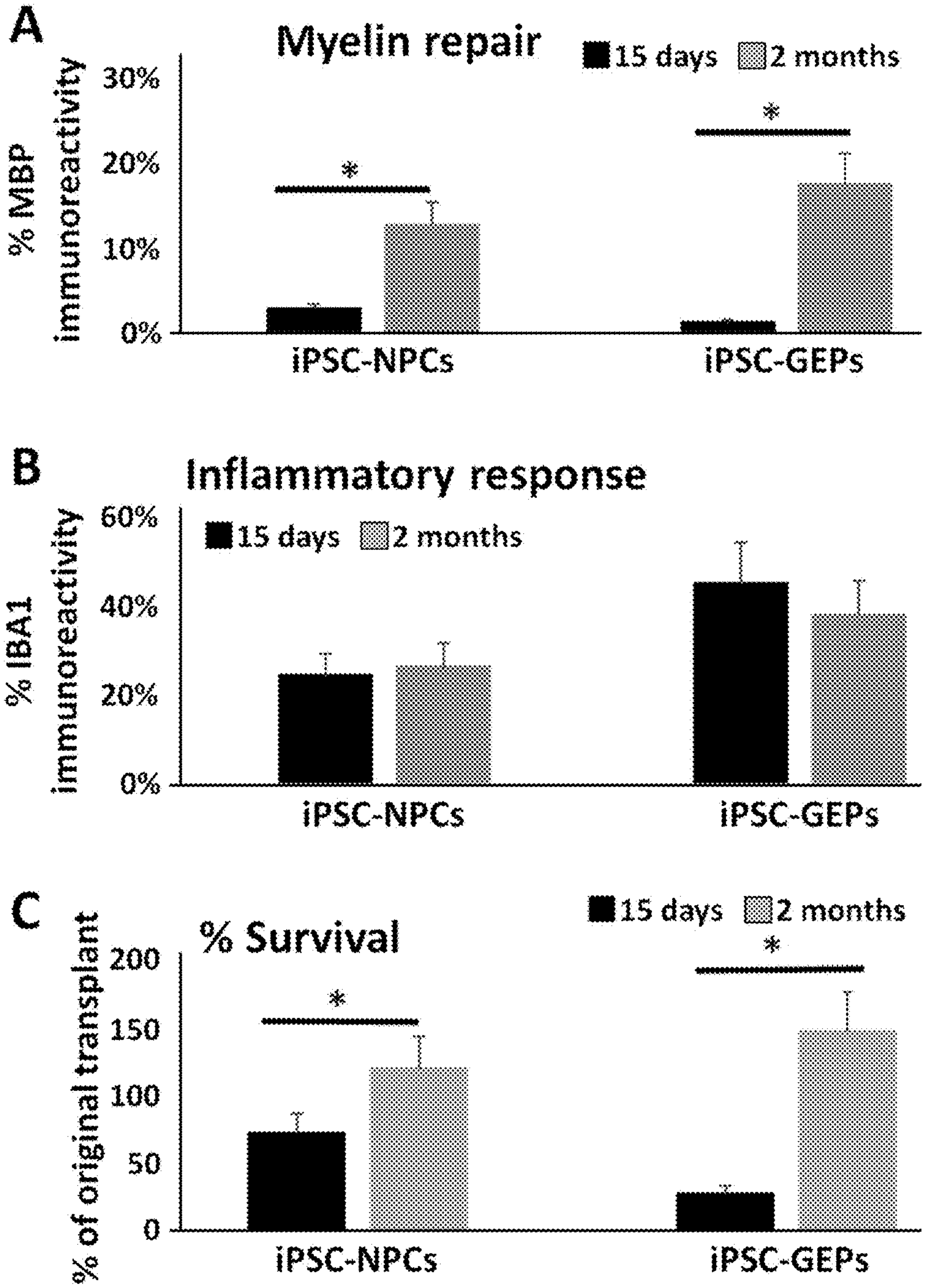
FIG. 10, panels A, B and C, shows quantification of myelin repair, inflammatory response and cell survival in the mouse bran following stroke injury and iPSC-NPCs or iPSC-GEPs transplantation. (A) Myelin repair is shown for each treatment groups at 2 and 8 weeks after cell transplantation. (B) Inflammatory response is shown for each treatment groups at 2 and 8 weeks after cell transplantation. (C) Cell survival is shown for each treatment groups at 2 and 8 weeks after cell transplantation. Abbreviations: MBP=myelin basic protein; IBA-1=ionized calcium-binding adapter molecule; iPSC-GEPs=induced pluripotent stem cells glial enriched progenitor cells.
Figure 11:
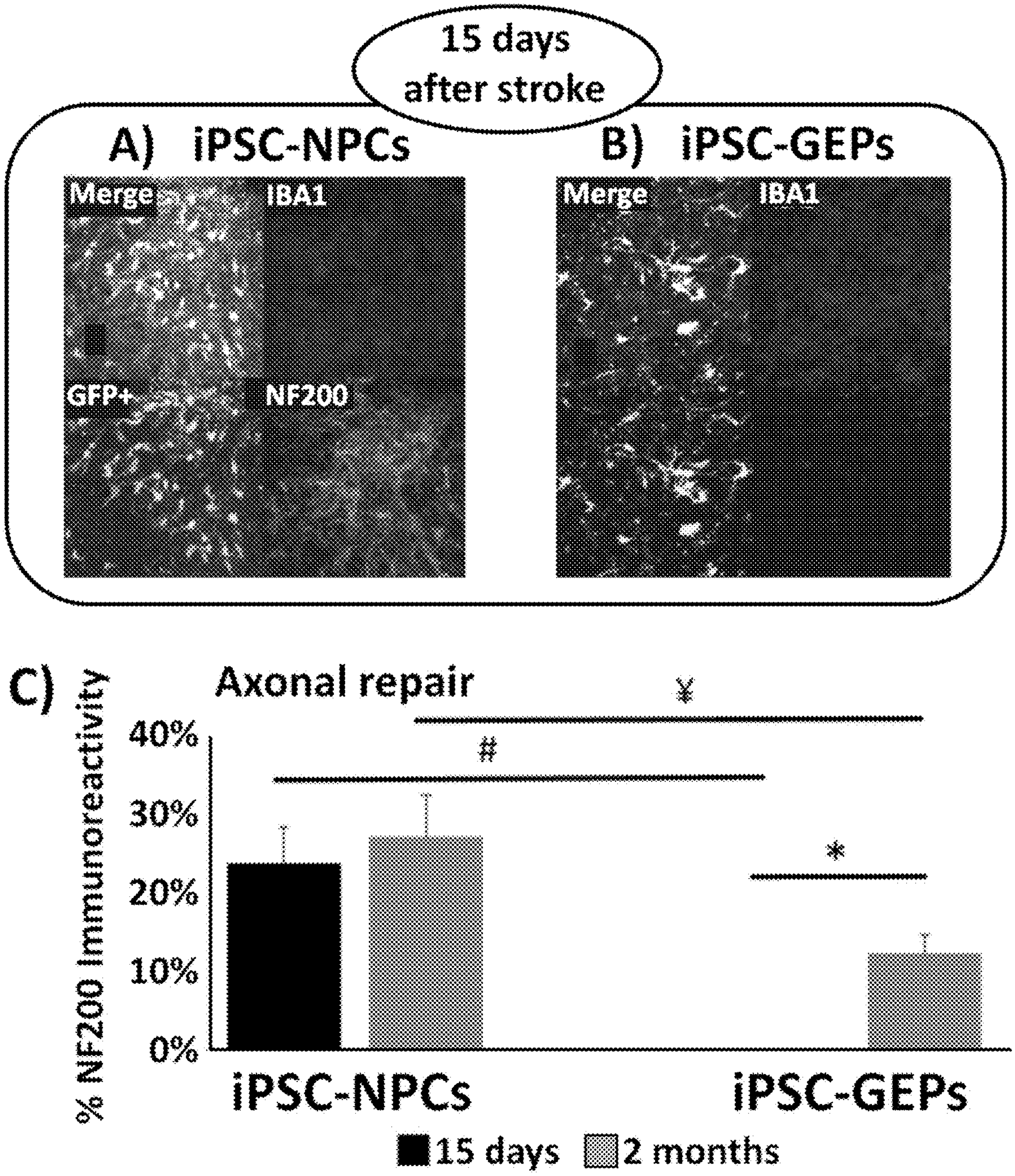
FIG. 11, panels A-C, shows representative fluorescent photomicrographs of iPSC-NPCs or iPSC-GEPs location, activated microglia/immune cells and axonal repair in the mouse brain following stroke injury. Image panels show fluorescent immunostaining of GFP+ cells (green), activated microglia/immune cells (IBA-1, blue) and NF200 (purple) 2 and 8 weeks after stroke injury following iPSC-NPCs or iPSC-GEPs transplantation. In panel A, panel 1 (left top) depicts the merged fluorescent image for GFP+, NF200 and IBA1, panel 2 (right top) depicts IBA-1 alone, panel 3 (left bottom) depicts GFP+ alone, and panel 4 (right bottom) depicts NF200 alone after 2 weeks of IPS-NPCs transplantation. In panel B, panel 1 (left top) depicts the merged fluorescent image for GFP+, NF200 and IBA1, panel 2 (right top) depicts IBA-1 alone, panel 3 (left bottom) depicts GFP+ alone, and panel 4 (right bottom) depicts NF200 alone after 2 weeks of IPS-GEPs transplantation. Panel C shows quantification of axonal repair in the mouse bran following stroke injury and iPSC-NPCs or iPSC-GEPs transplantation for each treatment groups at 2 weeks after cell transplantation. Magnification=600×. Abbreviations: NF200=neurofilament 200; MBP=myelin basic protein; IBA-1=ionized calcium-binding adapter molecule; iPSC-GEPs=induced pluripotent stem cells glial enriched progenitor cells.
Figure 12:
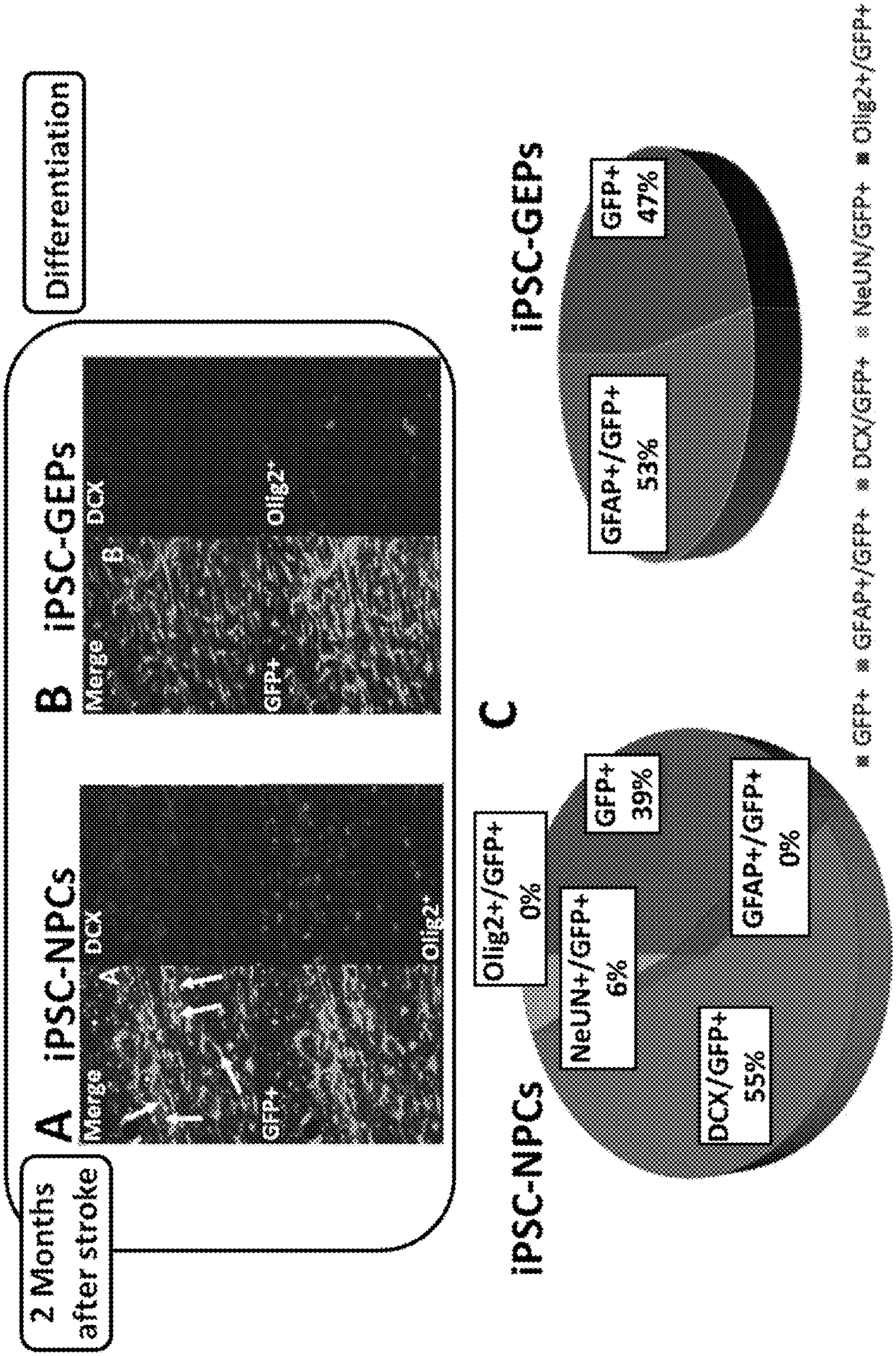
FIG. 12, panels A-C, shows representative fluorescent photomicrographs of iPSC-NPCs or iPSC-GEPs location, and cell differentiation in the mouse brain following stroke injury. Image panels show fluorescent immunostaining of GFP+ cells (green), inmature neurons (DCx, blue) and oligodendrocytes (OLIG2, red) 8 weeks after stroke injury following iPSC-NPCs or iPSC-GEPs transplantation. In panel A, panel 1 (left top) depicts the merged fluorescent image for GFP+, DCx and OLIG2, panel 2 (right top) depicts OLIG2 alone, panel 3 (left bottom) depicts GFP+ alone, and panel 4 (right bottom) depicts DCx alone after 8 weeks of IPS-NPCs transplantation. In panel B, panel 1 (left top) depicts the merged fluorescent image for GFP+, DCx and OLIG2, panel 2 (right top) depicts DCx alone, panel 3 (left bottom) depicts GFP+ alone, and panel 4 (right bottom) depicts OLIG2 alone after 8 weeks of IPS-GEPs transplantation. Panel C shows quantification of cell differentiation in the mouse bran following stroke injury and iPSC-NPCs or iPSC-GEPs transplantation for each treatment groups at 8 weeks after cell transplantation. Magnification=600×. Abbreviations: DCx=Doublecortin; iPSC-GEPs=induced pluripotent stem cells glial enriched progenitor cells.
Figure 13:
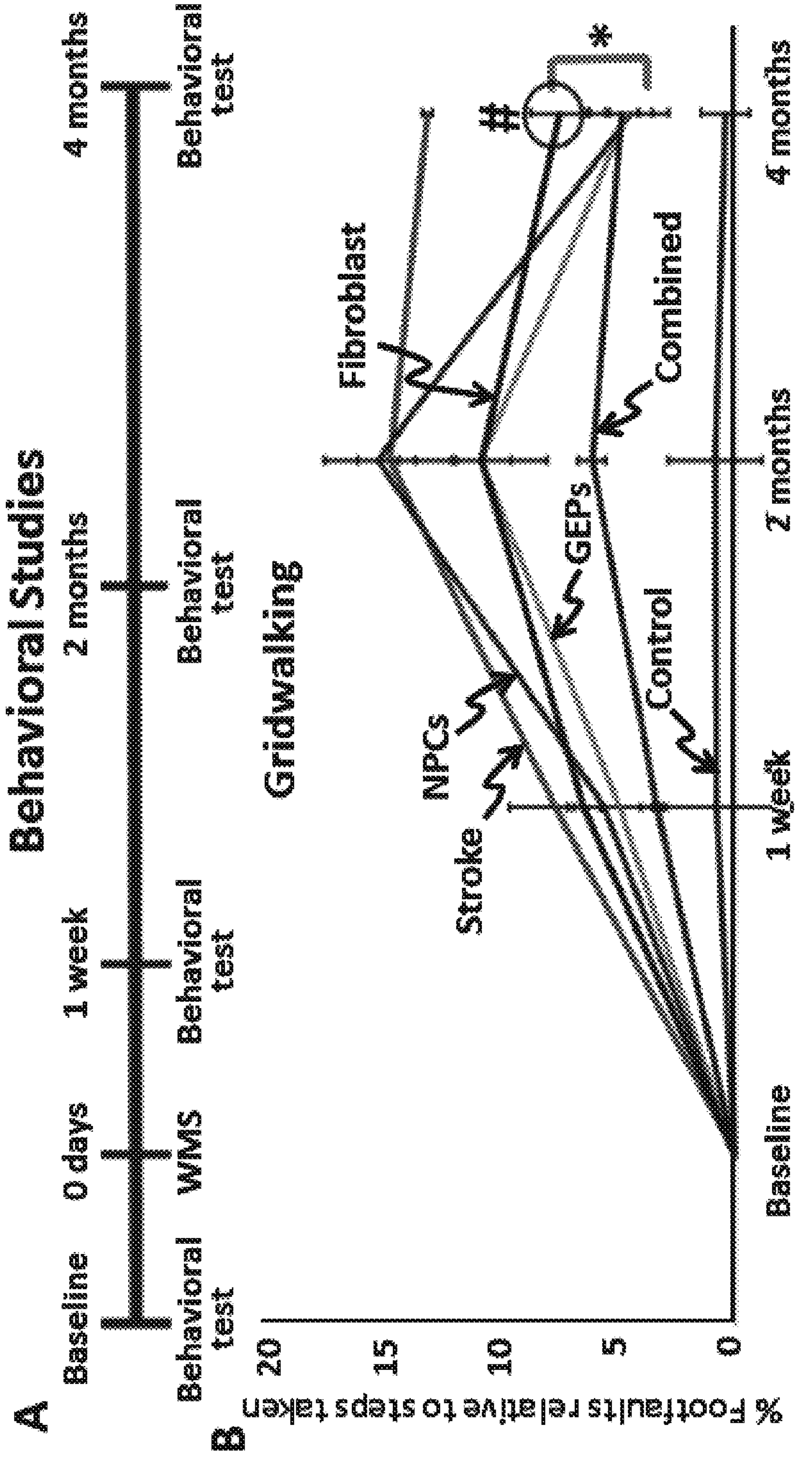
FIG. 13 panel A, shows the experimental timeline of Study 2 testing the effects of iPSC-NPCs and iPSC-GEPS on functional recovery and white matter sparing in a mouse model of white matter stroke. Key time points in the experimental design are shown, including cell transplantation 7 days post-stroke and monthly behavior testing. Panel B shows iPSC-NPCs or iPSC-GEPs transplantation into the lesion site improves performance of stroke-injured mice in the gridwalking test. Mean performance in the gridwalking test (shown as % foot faults) is shown for each treatment group as a function of time (post-stroke). One week post-stroke corresponds to the day prior to cell transplantation. Asterisk and hashtag indicate significance relative to the stroke group using two-way ANOVA with Tukey's HSD post-hoc analysis ($p<0.05$). At 4 months post-stroke, all stroke-injured groups with cell transplanted (iPSC-NPCs, iPSC-GEPs, iPSC-fibroblast and combined treatment) were significantly different from stroke, injured animals, indicating sustained de motor recovery. At the same time point, only the stroke+iPSC-fibroblast was significantly different from the other treatments groups, indicating less motor recovery after the transplantation. Treatment group labels: Control=uninjured, non-transplanted; stroke=stroke alone; stroke+iPSC-NPCs=stroke injury+100,000 iPSC-NPCs cells transplanted; stroke+iPSC-GEPs=stroke injury+100,000 iPSC-GEPs; stroke+iPSC-fibroblast=stroke injury+100,000 iPSC-fibroblast; stroke+combined treatment=stroke injury+50,000 iPSC-NPCs and 50,000 iPSC-GEPs.
Figure 14:
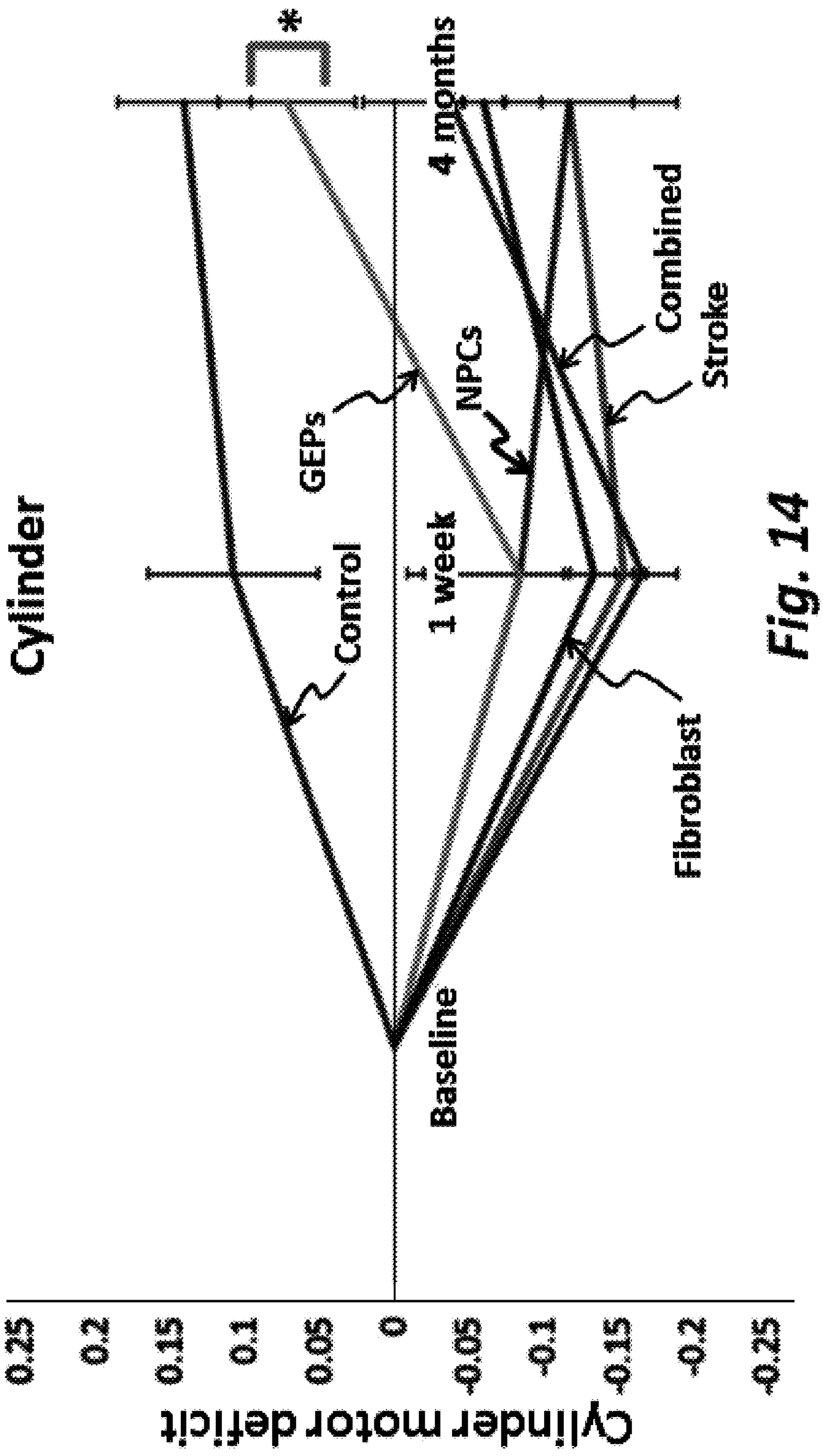
FIG. 14 shows iPSC-NPCs or iPSC-GEPs transplantation into the lesion site improves performance of stroke-injured mice in the cylinder test. Mean performance in the cylinder test (shown as motor deficit relative to pre-injury baseline) is shown for each treatment group as a function of time (post-stroke). One week post-stroke corresponds to the day prior to AST-OPC1 transplantation. Asterisk indicates significance relative to the the stroke alone group using two-way ANOVA with Tukey's HSD post-hoc analysis ($p<0.05$). One week post-stroke corresponds to the day prior to cell transplantation. Asterisk and hashtag indicate significance relative to the stroke group using two-way ANOVA with Tukey's HSD post-hoc analysis ($p<0.05$). At 4 months post-stroke, only the groups stroke+iPSC-GEPs was significantly difference from stroke alone group, indicating the best motor recovery between the different treatments. Treatment group labels: Control=uninjured, non-transplanted; stroke=stroke alone; stroke+iPSC-NPCs=stroke injury+100,000 iPSC-NPCs cells transplanted; stroke+iPSC-GEPs=stroke injury+100,000 iPSC-GEPs; stroke+iPSC-fibroblast=stroke injury+100,000 iPSC-fibroblast; stroke+combined treatment=stroke injury+50,000 iPSC-NPCs and 50,000 iPSC-GEPs.

A previously established mouse model of subcortical white matter stroke (Sozmen et al. (2009) *J. Neurosci Meth.* 180(2): 261; Hinman et al. (2013) *Stroke* 44(1): 182) that mimics the large white matter lesions seen in moderate to advanced human white matter ischemia or vascular dementia was used. Briefly, to induce focal ischemic lesions, N5-(1-iminoethyl)-L-ornithine, dihydrochloride (L-Nio, Calbiochem), was injected at three stereotactic coordinates directly into the corpus callosum of each mouse brain, as illustrated in FIG. 2.

Production of iPS-GEPS cDNAs for OCT4, SOX2, C-MYC, NANOG, KLF4, and GFP were cloned into the retroviral pMX vector and separately transfected into Phoenix Ampho Cells (Orbigen) by using Fugene (Roche). Viral supernatants were harvested 3 days later, combined, and used to infect human neonatal dermal fibroblasts (NHDF1; Lonza) in DMEM with 10% FBS, nonessential amino acids, L-glutamine, and penicillin-streptomycin. A second round of infection was performed at day 3, and the transfection efficiency of each virus as extrapolated from that of GFP in the viral mix was 15-20%, suggesting that nearly 100% of cells received at least one virus.

Four days later, cells were passaged onto irradiated murine embryonic fibroblasts (MEFs). Human induced PSCs (hiPSCs) were cultured as described previously (Patterson et al., 2012) in accordance with UCLA Embryonic Stem Cell Research Oversight committee. Feeder-free PSCs were maintained with mTeSRI (Stem Cell Technologies) and passaged mechanically using StemPro EZPassage Tool (Invitrogen). Neural rosette derivation, NPC purification, and further differentiation to neurons and glia were performed as described (Patterson et al., 2012). Briefly, rosettes were generated by growing PSCs for at least 7 days in Dulbecco's modified Eagle's medium (DMEM)/F12 with $N_2$ and B27 supplements (Invitrogen), 20 ng/ml basic fibroblast growth factor (FGF) (R&D Systems), 1 μM retinoic acid (RA) (Sigma), and 1 pM Sonic Hedgehog Agonist (Calbiochem). Once rosettes were picked, they were then cultured in NPC medium containing DMEM/F12, N2 and B27, 20 ng/ml basic FGF, and 500 ng/ml epidermal growth factor (EGF) (GIBCO). DFX (Sigma) (100 to 200 μM) were added at the NPC stage for 4 to 6 days, and their concentrations were adjusted for each cell line individually. NPCs were treated with or without 100 μM DFX for 3-5 days, and then returned to standard conditions until trypsinized for injection.

iPS-GEPs Transplantation in NSG Mice

Cells were stereotaxically transplanted 7 days after stroke. The temperature of the mice were monitored and maintained at 36.5-37.5° C. using a rectal probe and heating pad. A Hamilton syringe was filled with iPS-GEPs secured onto the stereotaxic arm and connected to a pressure pump. A second incision was made at AP +0.14, ML +3, DV −1.32. Two 0.45 pi injections of iPs-GEPs were given (100,000 cells/microL) at an angle of 36°. The needle was left in situ for 2 minutes after the first injection, and for 4 minutes after the second injection.

Brain Tissue Processing for Immunofluorescence, and MRI. Immunofluorescence

After the post-surgery survival period (15 days and 2 months), each mouse was given an overdose of isoflurane and perfused transcardially with 0.1 M phosphate buffered saline followed by 4% paraformaldehyde. The brains were removed, postfixed overnight in 4% paraformaldehyde and cryoprotected for 2 days in 30% sucrose. Subsequently brains were removed and frozen. Brain tissue was sectioned into 40 pm sections 200 pm apart using a cryostat (Leica CM 0530).

Immunostaining for microglial/macrophage marker IBA-1, the neuronal marker NF200, the astrocyte marker GFAP, the pan-oligodendrocyte marker Olig2, the mature oligodendrocyte maker MBP and the immature neuronal marker DCx was done by blocking in 5% normal donkey serum for 1 hour at room temperature, incubation in primary antibody overnight at 4° C., incubation in secondary antibody for 1 hour at room temperature, mounting sections onto subbed slides and air drying. Mounted sections were then dehydrated, in ascending concentrations of alcohol and xylene, and cover slipped with DPX.

Primary antibodies were: Rabbit anti-lba-1 (1:500, Wako Chemicals), rabbit anti-NF200 (1:500, Sigma), rat anti-myelin basic protein (MBP, T.500, Millipore), rabbit anti-Olig2 (1:500, Millipore), rat anti-GFAP (1:500, Millipore), goat anti-doublecortin (1:500, Santa Cruz Biotechnologies). All secondary antibodies were donkey F(ab')2 fragments conjugated to Cy2(cyan) or Cy3(yellow) (Jackson Immunoresearch) dyes and were used at a dilution of 1:1000.

Confocal Images

High-resolution confocal images in Z-stacks were acquired (Nikon C2 confocal system). Area measurements of the infarct core, IBA-1, GFAP, DCX, Olig2 and GFP positive cells were stereologically quantified using the optical fractionator probe and neuroanatomical quantification software (Stereoinvestigator, MBF Bioscience). White matter axonal projections stained with NF200 and MBP were quantified with intensity profiles (ImageJ, NIH).

MRI

Mice were anesthetized and placed in a Bruker 7T small animal MRI (Bruker Biospin, Switzerland). MRI imaging was performed on days 0, 7 and 6 months after stroke. Respiratory rate was monitored throughout the procedure and body temperature was maintained at 37±0.5° C. A T2-weighted image set was acquired: rapid acquisition relaxation enhancement factor 8, repetition time 5300 ms, echo time 15.00 ms with an in-plane resolution of 0.0156_0.0156_0.50 mm with 13 contiguous slices.

Tractography, diffusion tensor data (DTI) were acquired at 0, 7 and 6 months after treatment with a spin echo single shot echo planar imaging (EPI) pulse sequence using the following parameters: TR/TE: 5000/35 ms; a signal average of 10, a 30 noncolinear diffusion gradient scheme with diffusion weighting of b=1000 s/mm2 and b=0 s/mm2, and field of view 3.5×3.5 cm. The data was acquired using 30 directions with a single shot EPI sequence on a 96×96 matrix, and zero-filled k-space to construct a 128×128 image matrix. The images were obtained with medInria, a multi-platform medical image processing and visualization software. DTI tractography data was performed in the lesion zone using n=6 animals per group. Zoomed lesion site 3D views of DTI tractography images are represented using ParaView 4.1.0 software.

EXAMPLES

The following examples are offered to illustrate, but not to limit the claimed invention.

Example 1

Derivation and Characterization of iPS-GEP

The iPS-GEPs were extensively characterized in Xie et al. (2014) Stem Cell Reports 3: 743-757). They were shown to continue to express all the typical markers of human NPCs, namely SOX2, PAX6, SOX1, NESTIN etc., but also showed a distinct pattern of markers of neural development (Dlx, Fox, Ngn families of transcription factors).

When subjected to continued terminal differentiation by growth factor withdrawal, iPS-GEPs showed a dramatically higher propensity to produce cells of the astrocyte lineage as measured by GFAP and S100B staining. Despite the fact that iPS-GEPs only differ from standard NPCs by 3-5 days of DFX treatment, iPS-GEPs are permanently more astrocytic in their differentiation, both in vitro and in vivo after transplantation. The gene expression pattern of DFX-treated iPS-GEPs differs significantly from iPS-NPCs, and includes the differential expression of several growth factors that may play a role in neural repair (Table 1).

TABLE 1

Differentially expressed growth factors in iPS-GEP as compared to iPS-NPCs. iPS cells were exposed to deferoxamine for 2-3 days as described to induce iPS-GEPs or kept in standard NPC culture medium as described in EXAMPLE 1 and Materials and Methods. After 5 days, total RNA was isolated from cell types and used to probe whole genome microarrays. Genes corresponding to secreted growth factors were studied that had a fold expression of at least 1.54 fold higher in iPS-GEPs compared to iPS-NPCs. GDF15 (Growth Differentiation Factor 15) has the highest expression level in iPS-GEPs.

| Growth Factor | Full Name | Fold Increase vs. ISPS-NPCs |
|---|---|---|
| KITLG | Kit ligand/stem cell factor | 1.71 |
| GDNF | Glial cell-derived neurotrophic factor | 1.68 |
| GDF15 | Growth differentiation factor 15 | 4.52 |
| FGF11 | Fibroblast growth factor 11 | 1.75 |
| GDF3 | Growth differentiation factor 3 | 2.01 |
| GPI | Glucose-6-phosphate isomerase/neuroleukin | 1.66 |
| TGFA | Transforming growth factor alpha | 1.83 |
| VEGFA | Vascular endothelial growth factor alpha | 3.47 |

Example 2

Figure 1:
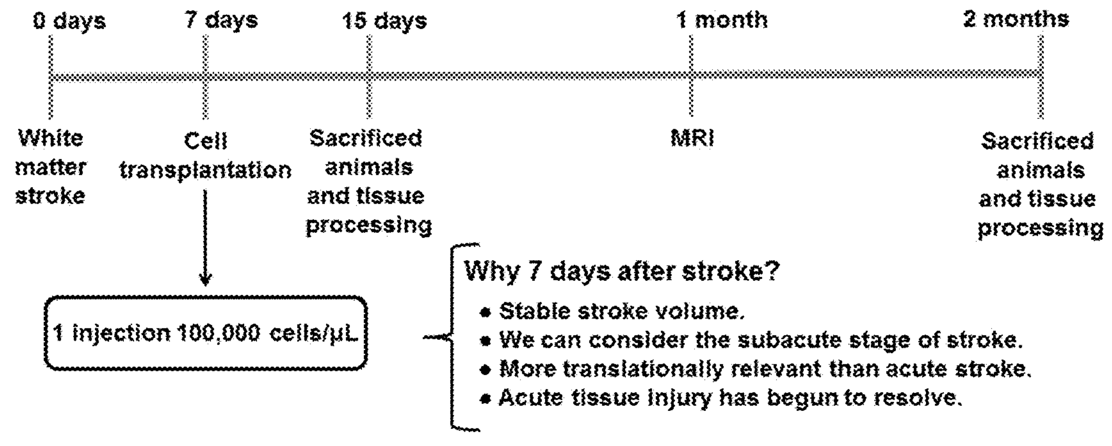
FIG. 1 shows an experimental timeline of Study 1 testing iPSC-NPCs or iPSC-GEPs transplantation in a mouse model of white matter stroke. Key time points in the experimental design are shown, including iPSC-NPCs or iPSC-GEPs transplantation seven days post-stroke and tissue processing, fifteen days post-cell transplant. iPSC-NPCs or iPSC-GEPs=100,000 cells/mouse as a single 1 μL injection. Abbreviations: L-NIO=N5-(1-iminoethyl)-L-ornithine, dihydrochloride; iPSC-NPCs=induced pluripotent stem cells neuronal progenitor cells; iPSC-GEPs=induced pluripotent stem cells glial-enriched progenitor cells.

Study 1—iPS-GEP Transplantation in a NSG Murine Model of White Matter Stroke To allow for full study of the iPS-GEP xenograft transplant, a previously established mouse model of subcortical white matter stroke (Sozmen et al. (2009) *J. Neurosci. Meth.* 180(2): 261; Hinman et al. (2013) *Stroke* 44(1): 182) that mimics the large white matter lesions seen in moderate to advanced human white matter ischemia or vascular dementia was adapted to the immunodeficient NSG mouse (Shultz et al. (2007) *Nat. Rev. Immunol.* 7(20):118; jaxmice.jax.org/nod-scid-gamma). Briefly, to induce focal ischemic lesions, N5-(1-iminoethyl)-L-ornithine, dihydrochloride (L-Nio, Calbiochem), was injected at three stereotactic coordinates directly into the corpus callosum of each mouse brain, as illustrated in FIG. 2. The experimental timeline is illustrated in FIG. 1. The study goals and parameters are described in detail in Table 2. Brain tissue was processed 15 days post stroke induction (i.e. two-weeks post iPSC-GEP or sham injection) and fluorescent immunostaining performed to determine the extent of myelination, axonal loss, astrocyte activation, microglial/macrophage responses and oligodendrocyte responses. Representative results are depicted in FIGS. 1-14.

TABLE 2

Study goals and parameters. Goals: Establish experience in transplantation and determine early survival and migration characteristics of iPS-GEPs in NSG white matter stroke; to understand the effects of the stroke environment on survival and migration.

| Group | Group Description |
|---|---|
| 1 | Stroke |
| 2 | Stroke + iPS-GEPs in peri-infarct white matter |
| 3 | Stroke + iPS-NPCs peri-infarct white matter |
| 4 | Control + iPS-GEPs + iPS-NPCs in peri-infarct white matter |

Sample size: 5 mice per group. Cell transplantation: 7 days after stroke, 100,000 cells/mouse in a single 1 pL injection delivered inside the infarct or immediately adjacent to infarct (peri- infarct) Survival: 2 weeks and 2 months post cell injection

Example 3

Study 2—Efficacy Study of iPS-GEPS for Behavioral Recovery

NSG mouse model of WMS as described in Example 2 was used to assess the effect of iPSC-GEP transplantation on behavioral recovery and whether iPSC-GEP transplantation improves white matter preservation based on MRI and ex vivo histochemical staining. The experimental timeline is illustrated in FIG. 1. The behavioral tests (cylinder test and grid walking) are described in detail in infra. Representative results are depicted in the Figures.

TABLE 3

Goals: Determine if change iPS-GEPs transplantation at 7 days after white matter stroke promotes neurological recovery based on behavior testing; determine whether change this to iPS-GEP transplantation improves white matter preservation based on MRI and ex vivo histochemical staining.

| Group | Description |
|---|---|
| 1 | Control (sham surgery) |
| 2 | Stroke alone |
| 3 | Stroke + iPS-fibroblast |
| 4 | Stroke + iPS-GEPs |
| 5 | Stroke + iPS-neuronal precursor cells (NPCs) |
| 6 | Stroke + iPS-GEPs + iPS-NPCs, |

Sample Size: 12 mice per group Animals: 72 mice total.
Cell transplantation: 7 days after stroke, 100,000 cells/mouse Behavior:

To measure proximal and distal motor control of the impaired forelimb, as well as hind limb function in gait. These test natural movements in the mouse.

Testing time points: pre-stroke (baseline), 7 days after stroke (before cell transplantation), 2 and 4 months.

MRI: Pre-stroke, one month after stroke.

Histology: Upon completion of behavior testing, brains are processed for histological evaluations of infarct size, endogenous brain repair and inflammation, and transplanted cell survival/phenotype.

Cylinder test. Exploratory behavior in mice provides a possibility to investigate the neural basis of spatial and motor behavior, which can be used as an assay of brain function. The cylinder test provides a way to evaluate a rodent's spontaneous forelimb use and has been used in a number of motor system injury models of stroke. To evaluate forelimb deficits, the animal is placed in a transparent Plexiglas cylinder and observed. Mice actively explore vertical surfaces by rearing up on their hind limbs and exploring the surface with their forelimbs and vibrissae. When assessing behavior in the cylinder, the number of independent wall placements observed for the right forelimb, left forelimb and both forelimbs simultaneously are recorded. Animals with unilateral brain damage will display an asymmetry in forelimb use during vertical exploration.

The cylinder task has been found to be objective, easy to use and score, sensitive to chronic deficits that others fail to detect and have high inter-rater reliability.

Grid walking test. The grid walking task, often referred to as the foot fault task, is a relatively simple way to assess motor impairments of limb functioning (most commonly hind limbs, but forelimbs have been evaluated as well) and placing deficits during locomotion in rodents. This task has been found to objectively demonstrate motor coordination deficits and rehabilitation effects after stroke. An animal is placed on an elevated, leveled grid with openings. Animals without brain damage will typically place their paws precisely on the wire frame-to hold themselves while moving along the grid. Each time a paw slips through an open grid, a "foot fault" is recorded. The number of both contra- and ipsilateral faults for each limb is compared to the total number of steps taken and then scored using a foot fault index. Intact animals will generally demonstrate few to no foot faults, and when faults occur, they do so symmetrically. Ischemic animals typically make significantly more contralateral foot faults than intact animals. The foot fault test has been shown to be a sensitive indicator for detecting impairments of sensorimotor function after ischemia in rodents.

Example 4

Patient Derived Glial Enriched Progenitors Repair Functional Deficits Due to White Matter Stroke and Vascular Dementia in Rodents Subcortical white matter stroke (WMS) accounts for up to 30% of all stroke events. WMS damages primary astrocytes, axons, oligodendrocytes, and myelin. We hypothesized that a therapeutic intervention targeting astrocytes would be ideally suited for brain repair after WMS. We characterize the cellular properties and in vivo tissue repair activity of glial enriched progenitor cells differentiated from human induced pluripotent stem cells, termed hiPSC-derived Glial Enriched Progenitors (hiPSCs-GEPs). hiPSC-GEPs are derived from hiPSC-Neural Progenitor cells (hiPSC-NPC) via an experimental manipulation of hypoxia inducible factor (HIF) activity by brief treatment with a prolyl hydroxylase inhibitor, deferoxamine. This treatment permanently biases these cells to further differentiate towards an astrocyte fate. hiPSC-GEPs transplanted into the brain in the subacute period after WMS in mice migrated widely, matured into astrocytes with a pro-repair phenotype, induced endogenous oligodendrocyte precursor proliferation and re-myelination, and promoted axonal sprouting. hiPSC-GEPs enhanced motor and cognitive recovery compared to other hiPSC-differentiated cell types. This approach establishes an hiPSC-derived product with easy scale-up capabilities that might be effective for treating WMS.

Results

Generation of a Model of White Matter Stroke

Figure 15:
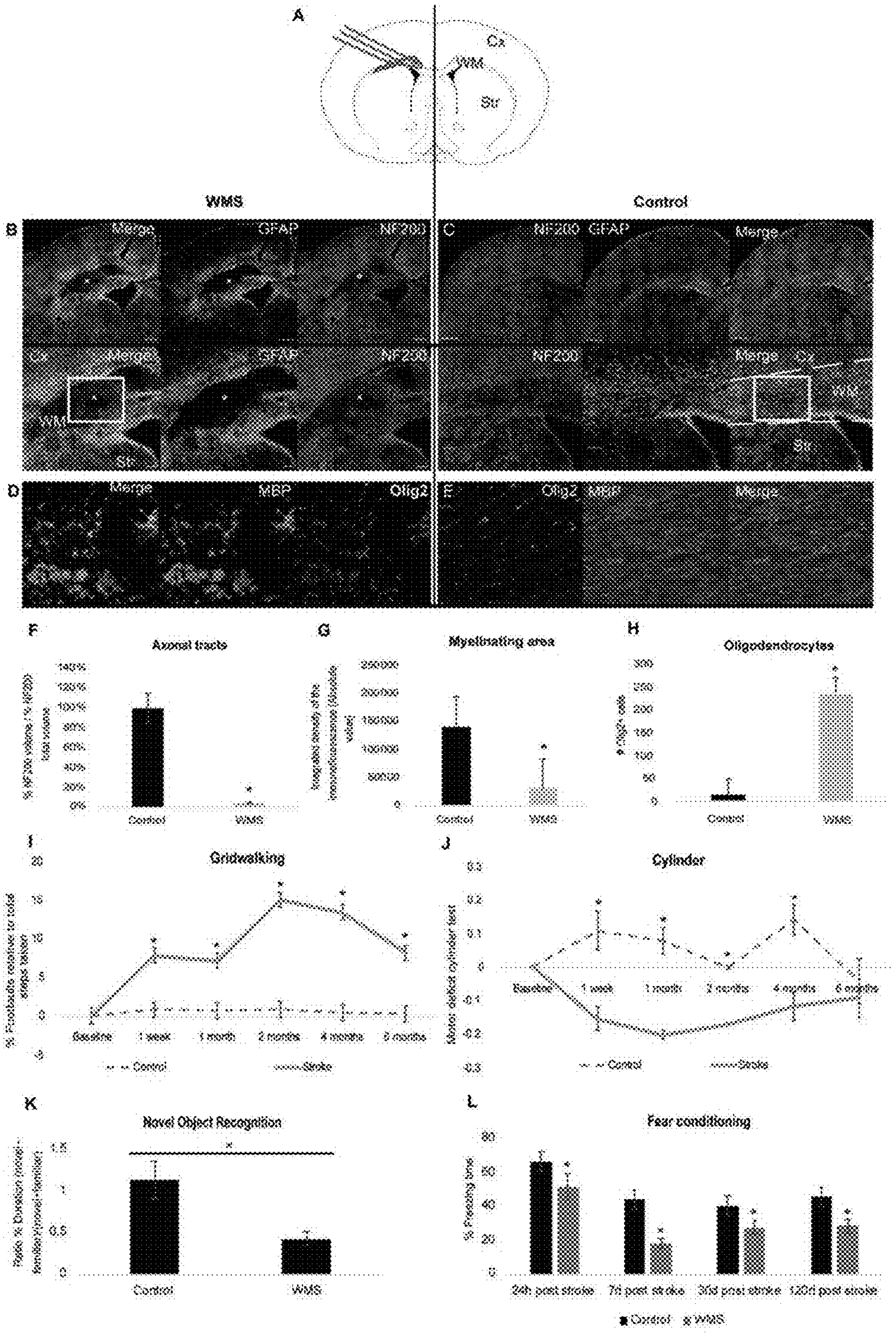
FIG. 15, panels A-L, shows that mouse subcortical white matter stroke produces a progressive deficit out to 4 months due to a localized axonal and myelin loss on the damage area. Panel A) Diagram of coronal mouse brain section indicating injection sites of L-NIO directly into the corpus callosum to induce a focal ischemic lesion. Image shows representative fluorescent photomicrographs of astrocyte activation (GFAP) and axonal loss (NF200) in the uninjured contralateral hemisphere (panel B, control) and stroke-injured hemisphere (panel C, white matter stroke). Panels D, E) Relative myelin loss (MBP, green) and oligodendrocyte presence (OLIG2, red), 15 days after stroke injury in the uninjured contralateral corpus callosum and the injured ipsilateral corpus callosum. Immunoreactivity quantification (panel F) axonal projections (NF200), (panel G) Myelin basic protein (MBP), (panel H) Average number of OLIG2 positive cells. In panels F, G and H n=6 mice per group; N=4. Significance was determined by Student's t test. (panel I) Grid walking test. Panel J) Cylinder test. Panel K) NOR. Panel L) Fear Conditioning. In panels I, J, K and L n=12 mice per group; N=2 *$P<0.05$ by one-way ANOVA followed by Tukey's HSD post hoc analysis values are means±SEM. WMS versus control.

A WMS model in the mouse (7) was modified to produce larger subcortical WM infarcts below the motor cortex to resemble the size and extent of those seen in the areas most commonly affected in vascular dementia in humans (19). This specific WMS predominantly damages astrocytes, oligodendrocytes and does not damage neurons 1-day post-stroke (FIG. 23). 15 days after focal microinjection of a vasoconstrictor (L-NIO) (FIG. 15, panel A), a stroke formed in the center of the injection site with loss of axonal connections (heavy chain neurofilament proteins, NF200) (FIG. 15, panels B, C) and surrounded by reactive astrocytes (GFAP) in the pen-infarct area (FIG. 15, panels B,C). There was also=[complete depletion of myelinating cells (myelin basic protein-MBP) in the infarct core and a localized increase in a marker for oligodendrocyte lineage cells (Olig2) (FIG. 15, panels D, E, F, *loss of axons $P<0.05$, *loss of oligodendrocytes $P<0.05$). This observation is in line with studies that have indicated that WMS OPCS divide and migrate towards the stroke area, but they do not differentiate into mature oligodendrocytes (7,20,21). Similar to what is seen in humans, this WMS model produced damage to axons, myelin, and astrocytes throughout a broad region of subcortical WM (19).

WMS produces deficits in motor and memory tasks. With no difference in pre-stroke baseline, one week after stroke, the WMS group showed a significant motor deficit indicated by an increase in contralateral forelimb foot faults in the grid-walking task compared with baseline (FIG. 15, panel I, *$P<0.05$). This motor deficit progressed in severity to 2 months post stroke and remained constant at 4 months post-stroke (FIG. 15, panel I, *$P<0.05$). In the cylinder-rearing test, mice had a progressive increase in forelimb motor function to 1-month post-stroke that remained constant until 4 months poststroke (FIG. 15, panel J). The Novel Object Recognition task measures the memory for an object after a time delay. (16). This task indicated a significant deficit for object preference and location tasks at 4 months post-stroke (FIG. 15, panel K, *$P<0.05$). Fear conditioning is a test for delayed recall of an environmental context (13). This test showed a significant decline in performance starting 24 h after WMS until 4 months post-WMS (FIG. 15, panel L, * $P<0.05$). Thus, this WMS model produced progressive, long lasting motor control and cognitive deficits that resembled the cognitive, gait and motor deficits seen in human vascular dementia (22).

Probing the Nature of hiPSC-Glial Enriched Progenitor Cells

Figure 16:
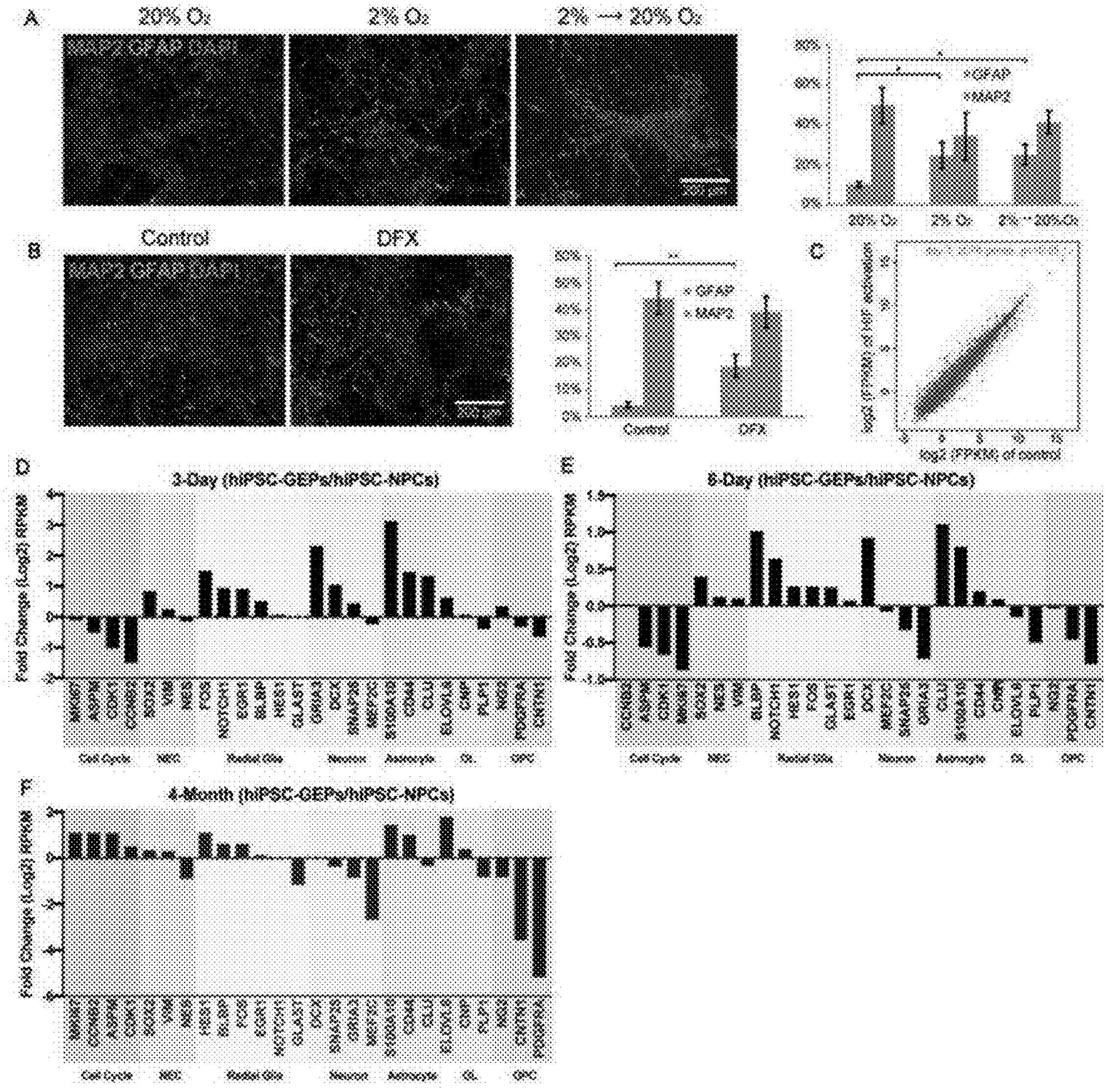
FIG. 16, panels A-F, shows that activation of HIF by low oxygen or small molecules at NPC stage promotes generation of astrocyte upon differentiation. Panel A) Directed differentiation of NPCs toward neurons and glia by growth factor withdrawal (GFWD). Right, culturing and differentiating NPCs in atmospheric oxygen tension (20% $O_2$), prolonged physiological oxygen tension (2% $O_2$), or a temporal exposure to physiological oxygen tension (2% $O_2$) in NPC generates both neurons and glia, 'which are assayed by immunostaining for MAP2 (neurons) or GFAP (astrocytes). Left, immunostaining demonstrates the strong effect of prolonged and temporal physiological oxygen on promoting astrogliogenesis. Panel B) Left, DFX NPC stage leads to an increase in astrocytes. Right, immunostaining shows (GFAP) percentage upon differentiation. (n=3 independent experiments with hESC or hiPSC-derived NPCs; mean±SEM; * $p<0.05$, ** $p<0.01$; Student's t test; scale bars, 200 pm). Panel C) Scatter plot marking in red the differentially expressed genes from RNA-seq data between control and three HIF activation conditions. HIF activation group is pooled from RNA-sequencing data using all three treatments: 2% O2, DFX, and DMOG. ($p<0.05$, likelihood ratio test). Panels D-F show relative fold change (hiPSC-GEP versus hiPSC-NPC) of cell type specific genes at various time points in log scale by RNA-seq (RPKM). In vitro cultured hiPSC-GEPs were treated with 2% Oxygen, DFX or DMOG for 3 days (panel D), or 3-day treatment with 2% Oxygen, DFX or DMOG followed by treatment-withdrawal for another 3 days (panel E). Relative fold change was calculated based on average gene expression of all three treatments versus control. Panel F shows in vivo transplanted GEPs versus control NPC obtained from WMS animals 4 months after transplantation.

Differentiation of hiPSCs to NPCs in 20% oxygen produces progenitors that further differentiate to produce roughly 3 times the number of neurons as astrocytes (17). When the same hiPSC-NPCs are differentiated in 2% oxygen for 3 weeks, similar amounts of neurons and astrocytes are produced (FIG. 16, panel A) (18). This glial shift in differentiation profile holds up when progenitors were treated with deferoxamine (DFX), an iron-chelating agent that blocks degradation of HIF by the PHD pathway (FIG. 16, panel B), or with Dimethyloxalylglycine, N-(Methoxyoxoacetyl)-glycine methyl ester (DMOG), another compound able to stabilize HIF protein even in atmospheric oxygen (23).

hiPSC-GEPs have now been derived by brief treatment of hiPSC-NPCs cells with DFX by our group and others (18,24). To identify the transcriptional response specific to this approach of HIF activation, we treated cells with low oxygen, DFX, or DMOG. We hypothesized that this approach would minimize the contribution of off-target effects induced by each of the three manipulations and allow us to focus on changes solely caused by regulation of HIF activity. After three days of these treatments, RNA was collected and processed for RNA-seq. Across the three distinct HIF-activating treatments, 2076 differentially expressed genes were identified (FIG. 16, panel C). These results were consistent with HIF activation suppressing oxidative phosphorylation and mitochondrial respiration.

Shortly after HIF activation, the transcriptional profile of hiPSC-GEPs at day 3 showed down-regulated cell cycle genes G2/Mitotic-Specific Cyclin-B2, Cyclin Dependent Kinase 1 (CCNB2 and CDK1), activated Notch signaling (Notch1), and up-regulated pro-glia genes, brain lipid binding protein (BLBP) (FIG. 16, panel D), compared with control hiPSC-NPC. Those mRNA profiles indicate that hiPSC-GEPs are compatible with a late-stage radial glial cell (RG), whereas the control NPCs are more closely related to dividing neuroepithelial cells (NECs) and early-stage RG (FIG. 24).

The transcriptional analysis also suggested that an astrocyte fate is induced in a portion of the progenitors upon HIF activation. Several transcription factors that activate astrogliogenesis were induced upon HIF activation, such as Nuclear Factor I X (NFIX) (25) and SRY-Box Transcription Factor 9 (SOX9) (26) (FIG. 25). In addition, CD44 was highly induced in all three HIF-activation conditions (FIG. 16, panel D). Others have shown that CD44 expression identifies astrocyte-restricted precursor cells (27,28). Moreover, a pro-repair astrocyte marker gene, 5100 Calcium Binding Protein A10 (S100A10), was upregulated (FIG. 16, panel D), and remained upregulated in hiPSC-GEPs 4-months after stroke. (FIG. 16, panel F). These data are consistent with the observation that HIF-activated neural progenitors are more astrogliogenic and suggest that HIF-activation can promote cell fate transition toward a late-stage pro-glia radial glia fate or astrocyte-restricted progenitor (29).

To uncover transcriptional changes that persist after HIF induction has stopped, we profiled cells after the pulse-chase treatment with DFX (3-day treatment, 3-day chase in absence of HIF activating stimulus). Pro-glia Notch signaling (Notch1, and Hes Family BHLH Transcription Factor 1—Hes1), and a late stage RG marker (BLBP) remained upregulated at day 6, consistent with an NEC to RG transition (FIG. 16, panel E, FIG. 25). Also, consistent with this fate change, astrocyte specific genes (S100A10, clusterin—CLU) were induced, but not genes associated with neuron, oligodendrocyte, or oligodendrocyte progenitor cell (OPC) (FIG. 16, panel E).

Figure 17:
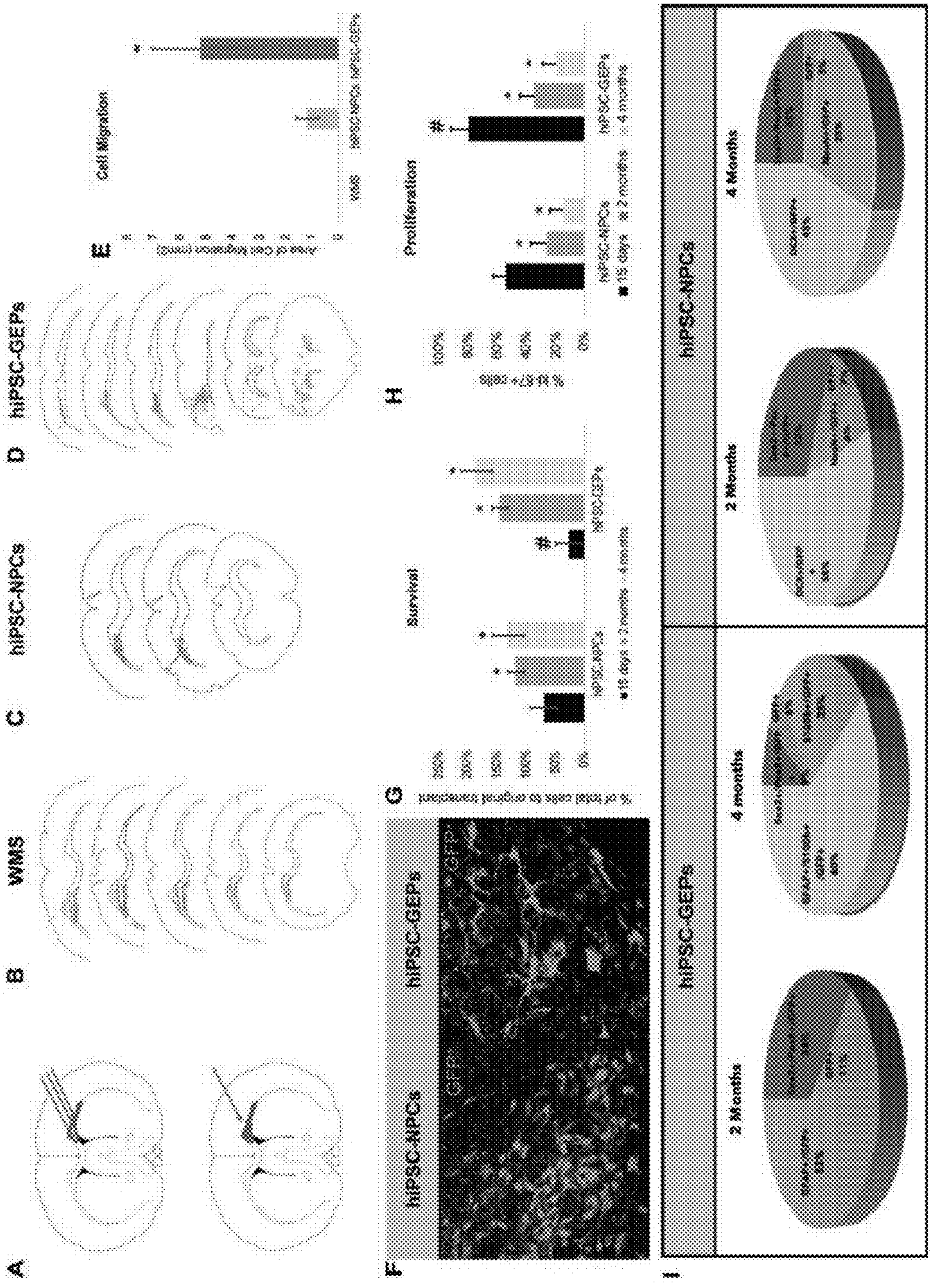
FIG. 17 shows that hiPSC-derived neural progenitors transplanted after subcortical white matter stroke produce myelin and axonal repair. Panel A) Diagram of coronal mouse brain section indicating injection sites of L-NIO directly into the corpus callosum to induce a focal ischemic lesion (top) and diagram of coronal mouse brain section indicating cell injection site into the uninjured corpus callosum. Panel B) Representative mouse coronal sections indicating the infarct area region. Panels C, D) Dots represent the position of single human cells. Panels C,D) Representative mouse coronal sections indicating the position of hiPSC-NPCs or hiPSC-GEPs after 2 months posttransplant. Panel E) Area of cell migration quatification 2 months post-transplant. *Area of hiPSC-NPCs cell migration vs area of hiPSC-GEPs cell migration. Image panel F shows fluorescent immunostaining of GFP+ cells (green). Panel1 G show quantification of cell survival (number of GFP+ cells), 15 days, 2 and 4 months after stroke injury following hiPSC-NPCs or hiPSC-GEPs transplantation. *15 days vs 2 and 4 months after transplant. #15 days hiPSC-NPCs vs hiPSC-GEPs. Panel H shows quantification of cell proliferation (number of ki-67+ cells), 15 days, 2 and 4 months after stroke injury following hiPSC-NPCs or hiPSC-GEPs transplantation. *15 days vs 2 and 4 months after transplant. #15 days hiPSC-NPCs vs hiPSC-GEPs. Panel I shows hiPSC-NPCs and hiPSC-GEPs phenotype quantification. E, G and H, n=6 mice per group; N=4; $P<0.05$ by one-way ANOVA followed by Tukey's HSD post hoc analysis, values are means±SEM.

To determine whether this shift in fate is permanent in hiPSC-GEPs after DFX treatment, we performed the same transcriptome analysis 4 months later. At 4 months, astrocyte specific genes remained highly expressed in hiPSC-GEPs with 2.7-fold more S100A10 and 2-fold more CD44 than hiPSC-NPCs, whereas neuron- and OPC-related genes were suppressed (FIG. 16, panel F). These results show that hiPSC-GEPs retained a long-term glial differentiation bias even after a brief treatment in vitro with DFX.

hiPSC-NPCs and -GEPs Transplantation Into White Matter Stroke.

hiPSC-GEPs and hiPSC-NPCs were assessed for effect in tissue repair after WMS. Cells were transplanted seven days after stroke induction, corresponding to a subacute period in human stroke (up to approximately 3 months after stroke) (30), which would be a clinically relevant time point for a transplant therapy (FIG. 17, panel A). Cohorts of mice (n=6 for each group) were sacrificed at early and late time points (15 days, 2 months and 4 months post-transplant) to assay hiPSC-GEP and hiPSC-NPC migration, survival, proliferation and differentiation in the stroke WM. The response of hiPSC-GEPs was compared to hiPSC-NPCs for two reasons: hiPSC-NPCs are the parent cell type from which hiPSC-GEPs are derived, and hiPSC-NPCs are commonly used in pre-clinical transplant studies in cortical stroke (31, 32). Two months after transplant, hiPSC-NPCs migrated only a short distance in the anterior/posterior plane and did not leave the injury site. In contrast hiPSC-GEPs migrated widely to contralateral WM, striatum and cortex (FIG. 17, panels B, C, D, E).

hiPSC-NPCs had a significantly better survival in the early time period (15 days) than hipSC-GEPs (70% vs. 25%, FIG. 17, panels F, G *, # $P<0.05$). There was a significant proliferative response of the transplanted human cells in the brain for both cell types (FIG. 17, panels F, G *, # $P<0.05$). However, hiPSC-GEPs displayed a higher proliferation rate after 2 months of transplantation compared to hiPSC-NPCs (80% vs. 40%-50% of hiPSC-NPCs vs 80% hiPSC-GEPs are Ki-67+) (FIG. 17, panels F, G, H). Although proliferation was observed in both groups, there was no tumor, teratoma, or cyst detected in any animal and no immunoreactivity for pluripotent markers. There was a peak of proliferation between 15 days and 2 months in both hiPSC-NPC and hiPSC-GEP transplantation: a 48% hiPSC-NPCs (27.04% Ki-67+) and 120% hiPSC-GEPs increase in the number of GFP+ cells (35% Ki-$67^{+}$) 2 months post-transplant compared with 15 days (FIG. 17, panels F, G, H). However, the proliferation was substantially decreased between 2 and 4 months after transplant: there was a 27% hiPSC-NPC (15% Ki-$67^{+}$) and 47% hiPSC-GEP increase in the number of GFP+ cells (20% Ki-67+) 4 months post-transplant compared with the 2-month time point (FIG. 17, panels F, G, H). There were no differences in microglial/immune cell activation after white matter stroke following hiPSC-NPCs or hiPSC-GEPs transplant (FIG. 26).

To more definitively determine the differentiation profile of hiPSC-derived progenitors in the long term, we characterized the phenotype of hiPSC-GEPs and hiPSC-NPCs at 2 and 4 months after transplant in WMS. At 2 months post-transplant, hiPSC-GEPs expressed human GFAP (53%) but not makers of immature or mature neurons or OPCs. However, hiPSC-NPCs expressed a marker of immature neurons (DCX) (55%) (FIG. 17, panel I), and a small number expressed NeuN (6%), a marker of mature neurons. hiPSC-NPCs did not express human GFAP even at 4 months after transplant. After 4 months, 45% of hiPSC-NPCs expressed the immature neuronal marker DCX and 25% of the hiPSC-NPCs expressed NeuN (FIG. 17, panel I). However, with hiPSC-GEPS, 4 months after transplant 65% expressed the astrocyte marker S100P and 40% [of the hiPSC-GEPs expressed the pan-astrocyte marker human GFAP (FIG. 17, panel I). 0% of the transplanted hiPSC-GEPS expressed NeuN, DCX, Olig2, CC1, GSTn or MBP. In contrast, 0% of the transplanted hiPSC-NPCs expressed GFAP, S100b, Olig2, CC1, GSTn or MBP. These observations are consistent with RNA-seq data at 4 months showing that treating hiPSC-NPCs via DFX to transiently induce HIF in culture produces a long-lasting bias after many months towards an astrocyte fate in vitro (FIG. 24) and in vivo (FIG. 17, panel I). Thus, the hiPSC-GEPs are indeed "glial enriched progenitors" in that they produce hGFAP+/S100p+ cells but few neurons or oligodendrocyte-lineage cells.

Astrocytes are intimately associated with and regulate the cerebral vasculature (33). To determine if transplanted human immature astrocytes in WMS recapitulate this vascular relationship, the distance between the hiPSC-GEPs that expressed immature (hGFAP) and/or mature (S100P) astrocyte markers and the closest blood vessel was measured 4 months post-transplant (FIG. 27). 85% of the hiPSC-GEPs were within 0-50 pm from vessels. hiPSC-NPCs localized more distantly from vessels, with 55% of hiPSC-NPCs found 50-100 pm away and expressing neuronal markers (DCX and NeuN) (FIG. 27). These data indicate that transition of the parent hiPSC-NPC into hiPSC-GEPs prior to transplant creates progenitors that are astrocyte-like and associate with vessels in a similar fashion to endogenous brain astrocytes.

Brain Imaging and Neuronal Connections in iPS Transplantation in White Matter Stroke We next analyzed anatomical measures of tissue repair in this stroke after cell transplantation. A hallmark of human WMS and vascular dementia is hyperintensity on T2-weighted or fluid-attenuated inversion recovery (FLAIR) MRI (4,19) with altered metrics of water diffusion (fractional anisotropy-FA, mean diffusivity-MD and axial diffusivity-AD). We measured WM injury and repair using these same human MRI metrics in our mouse model. WMS produced a large region of hyperintensity on T2-weighted imaging in the subcortical WM at one month (FIG. 28, panel A). hiPSC-GEP transplantation produced a normalization of the stroke WM signal (FIG. 28, panel C). hiPSC-NPC transplantation produced a signal in WM with elements of hyperintensity that was intermediate between stroke and hiPSC-GEPs transplant (FIG. 28, panel B). WM structure was further quantified with DTI. WMS caused a 66% and 50% decrease on AD and FA measurements respectively, which are indicators of demyelination and axonal degeneration (34) (FIG. 28, panels D,E). These changes were sustained over 4 months after stroke. In contrast to the effect of WMS decreasing FA and AD, hiPSC-GEP transplantation caused a roughly 50% increase 4 months after transplant on AD and FA measurements compared with WMS (FIG. 28, panels D,E). hiPSC-NPC transplantation caused a 50%-65% increase in AD measurements compared with WMS 1 and 4 months after transplant respectively, as well as a 50% increase on FA 4 months post-transplant (FIG. 28, panels D, E). These results show a significant improvement in WM thickness (width, breadth, depth) (FIG. 28, panels D, E, F, *, #P<0.05, * WMS vs hiPSC-NPCS or hiPSC-GEPs, #1-month vs 4-months after transplant). Stroke induces the formation of new connections in cortical and subcortical areas, which has been causally associated with motor recovery in ipsilesional cortex (35,36). To determine the effect of hiPSC-NPC or -GEP transplantation on axonal sprouting after WMS, we densitometrically measured axonal connections (35) after hiPSC-NPC or -GEP delivery in prominent axonal systems of the motor cortex: ipsilateral connections to adjacent cortical areas, to contralateral motor cortex, and to ipsilateral and contralateral WM (FIG. 18, panels A, B). 4 months after the stroke, the axonal tracer BDA was microinjected into the forelimb motor cortex (that is not directly damaged) located above the stroke site. Axonal connections were compared across WMS, WMS+hiPSC-NPCs and WMS+hiPSC-GEPs. Connections were quantified using linear fluorescent measurements which correlate with direct axonal counts (FIG. 18, panels A, B) (35). WMS caused a loss of motor system connections from cortex near the stroke site and through the stroke-injured WM. At 4 months after transplant into WM, hiPSC-GEP transplant showedˆ! greater motor cortex axonal connection density between forelimb motor cortex and ipsilateral and contralateral cortical areas (FIG. 418, panels, B). In contrast to the increased density of projections to the contralateral cortex with hiPSC-GEPs, hiPSC-NPCs transplantation established greater axonal density in the injured WM (FIG. 18, panels A, B) but not overlying cortex. These data suggest that hiPSC-GEPs fosters axonal projections between cortical target zones after WMS, possibly through collateral sprouting within cortex, whereas hiPSC-NPCs increase local axonal projections in the injured WM without termination in cortex.

Figure 18:
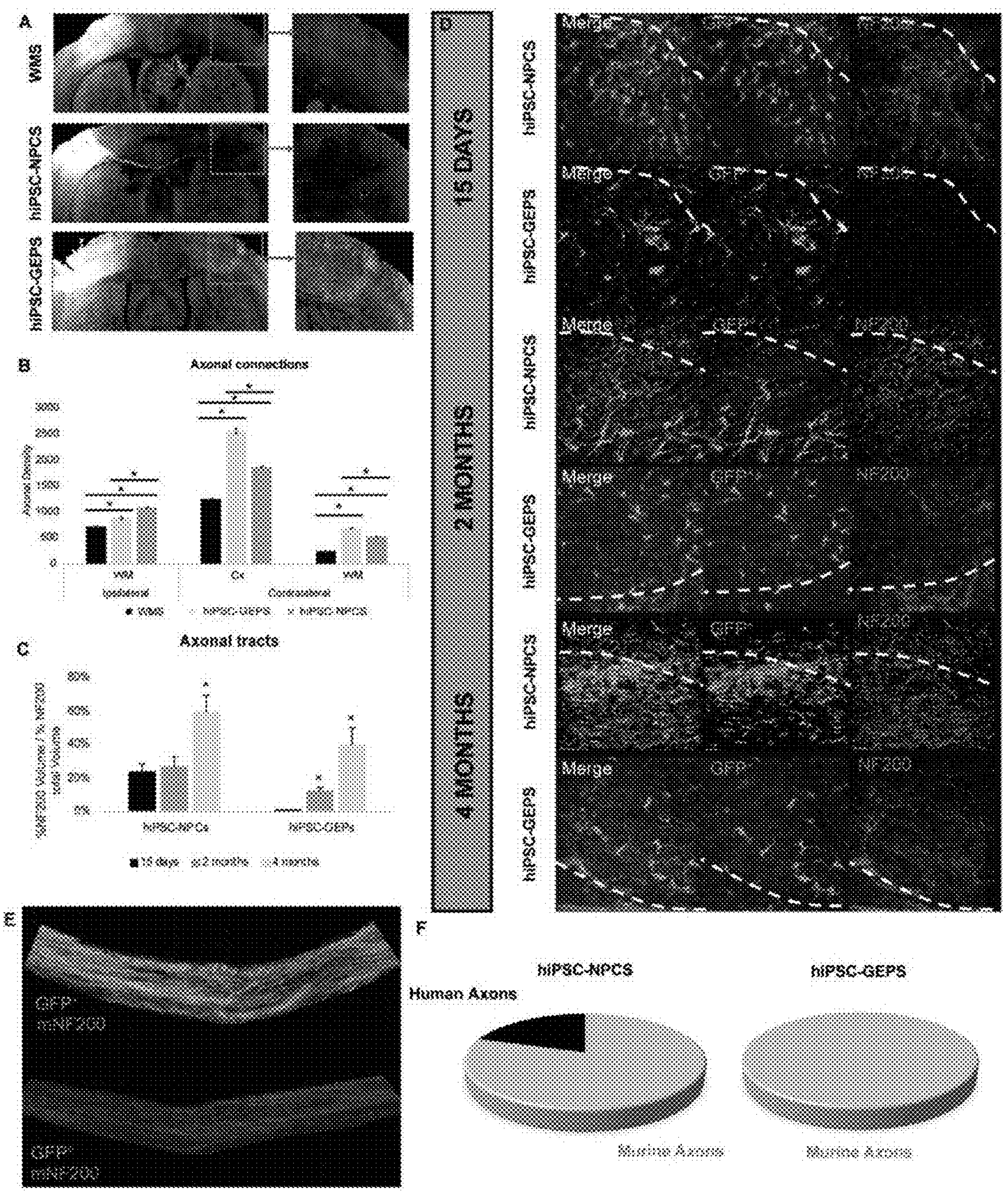
FIG. 18, panels A-F, shows that hiPSC-derived progenitor transplantation reduced infarct size, increased fiber tract and axonal projections density after subcortical white matter damage. Panel A) Image panels show fluorescent immunostaining of $GFP^+$ cells (green) and axonal repair (NF200-red) 15 days, 2 and 4 months after stroke injury following hiPSC-NPCs or hiPSC-GEPs transplant. Panel B) Quantification of axonal growth. *$P<0.05$ by two-way ANOVA followed by Tukey's HSD post hoc analysis, 2- and 4-months hiPSC-NPCs or hiPSC-GEPs transplant vs 15 days hiPSC-NPCs or hiPSC-GEPs transplant comparison; n=6 mice per group; N=4. Panel C) Images of biotinylated dextran amine (BDA)-labeled connections from motor cortex ipsilateral. Panel D) Quantification of axonal projections. * $P<0.05$ by two-way ANOVA followed by Tukey's HSD post hoc analysis, WMS versus hiPSC-NPCs or hiPSC-GEPs transplant comparison; n=6 mice per group; N=2. Panel E) Image panels show fluorescent immunostaining of GFP+ human axonal projections (green) and endogenous axonal projections (reed) 4 months after stroke injury following hiPSC-NPCs or hiPSC-GEPs transplant. Panel F) Quantification of Endogenous axonal projections (NF200 immunoreactivity) vs Transplant projections (GFP+ axonal projections). Panels B, D and F values are means±SEM.

Both hiPSC-GEPs and hiPSC-NPCs had an effect on axonal growth and produced an increase in axonal density (NF200). However, there was a greater effect of hiPSC-NPCs on markers of axonal density (FIG. 18, panels C, D). This increase was present within and adjacent to the infarct. As we observed on the endogenous tissue response analysis, there was a greater staining and extent of $NF200^+$ axons in stroke-injured WM after hiPSC-NPC compared to hiPSC-GEP transplantation on the early 15 day and 2-month time points (20-25%, FIG. 18, panel D). However, there was a significantly higher NF200 immunopositivity in the ipsilateral side after hiPSC-NPC transplant after WMS at 4 months (39% hiPSC-GEPs vs 61% hiPSC-NPCs, * P<0.05). This increase in NF200+ axons was due in part to neuronal differentiation of the hiPSC-NPCs themselves and local extension of human axons in the mouse WM (FIG. 18, panels E, F): human neurofilament-positive axons were compared to mouse neurofilament-positive axons in the WM adjacent to the infarct. This region had 20% human NF200+ vs 80% mouse NF200+(FIG. 18, panels E, F). After hiPSC-GEP transplant, all NF200+ fibers found in the injury site had a murine origin (FIG. 18, panels E, F), indicating that the transplanted glial-differentiated cells were not capable of neuronal differentiation. This observation is also consistent with the down-regulated neuronal marker MEF2C and proneuron transcription factor DLX1 in 4-month hiPSC-GEP RNA-seq data.

In contrast, to the local neuronal differentiation within WM of hiPSC-NPCs, there was a greater effect of hiPSC-GEPs on markers of myelination (FIG. 19, panels A, B). The myelin around the infarct site showed greater integrity and staining for MBP after hiPSC-GEP transplantation (20%) at 2 months (FIG. 19, panel B). We also analyzed MBP at a time period of behavioral improvement (4 months after transplant, next section), and showed a higher immunopositivity in the ipsilateral side after transplantation of hiPSC-GEPs following WMS (59% hiPSC-GEPs vs 33% hiPSC-NPCs) (FIG. 19, panel B). To explore lineage differentiation in the oligodendrocyte series, we quantified the number of immature (Olig2) and mature endogenous oligodendrocytes (CC1 and GSTn) at 4 months after stroke (FIG. 19, panels C, D). After hiPSC-NPCs transplant there was a mild increase in the number of mature oligodendrocytes in the ipsilateral WM: $CC1^+$ and $GSTn^+$ cells were 4.3 and 6 times higher compared with the WMS-alone group respectively (FIG. 19, panels C, D). However, after hiPSC-GEP transplant, the increase in the number of $CC1^+$ and $GSTn^+$ mature oligodendrocytes in the ipsilateral side were highly significant: 22 times and 14 times higher compared to WMS respectively (FIG. 19, panels C, D, * P<0.05).

In summary, transplanted hiPSC-NPCs after WMS induced an increase in OPCs and immature neurons in the ipsilateral WM. However, transplantation of hiPSC-GEPs induced fewer immature cells |(OPCs and neurons) but induced a 71% greater increase in the cells with markers of mature oligodendrocytes compared to hiPSC-NPCs. This effect, particularly from hiPSC-GEP transplantation, on induction of cells expressing mature oligodendrocyte markers could explain the greater myelination of the injury site shown in MRI (FIG. 28) and MBP staining (FIG. 19, panels C, D) at one- and two-month time points.

To directly visualize myelin integrity separate cohorts of WMS, WMS+hiPSC-NPCs and WMS+hiPSC-GEPs mice were processed for electron microscopy (n=5 each), the number of myelinated and unmyelinated fibers and g ratio were measured in the corpus callosum medial to the stroke site at 16 weeks after stroke. The g ratio is the ratio of the inner axonal diameter to the total outer diameter, a sensitive indicator of remyelination. There were no differences between the different experimental groups in the g ratio (FIG. 19, panels E, F). However, hiPSC-GEPs transplantation after WMS promotes remyelination of axons adjacent to the infarct, seen as an increase in the total percentage of myelinated axons (59% myelinated axons) adjacent to the stroke site compare to the WMS and WMS+hiPSC-NPCs groups (28% and 43% respectively) (FIG. 19, panel G, *P<0.05). These results indicate that hiPSC-GEPs transplant post-WMS enhances not only OPC differentiation but increases remyelination in the brain after subcortical white matter stroke.

Thus, we have demonstrated that although both hiPSC-NPC and hiPSC-GEP transplants led to an increase in neurofilament-positive axons in white matter and cortex, this was through two differ=mechanisms. hiPSC-GEP transplants promoted greater endogenous axonal growth in local and distant cortical areas and oligodendrogenesis that also led to increased myelinogenesis. hiPSC-NPCs differentiated into human neurons and extended local axons in white matter.

The Differentiation State of hiPSC-Derived Neural Progenitors Determines Functional Outcome After Stroke To determine if hiPSC-NPC or -GEP transplants promote functional recovery after WMS, we tested mice on forelimb motor tasks with this WMS model after transplantation of hiPSC-GEPs, hiPSC-NPCs and hiPSC-fibroblasts (non-neural line) using motor control measures established for baseline stroke (FIG. 20, panels A-B). Transplantation of all hiPSC-derived cell types improved motor performance after stroke to variable degrees. The most substantial improvement was observed with hiPSC-GEP transplantation, which improved motor control in both gridwalking and cylinder tasks 4 months post-transplant (FIG. 20, panels A-B), and was the only hiPSC-derived cell type to improve motor control after stroke in the cylinder task (FIG. 20, panel A). hiPSC-NPCs significantly improved motor control only in the gridwalking task (* P<0.05). In contrast, there was no behavioral improvement due to the hiPSC-Fibroblast transplant in either of the forelimb motor tasks. There was no difference between testing at 2 to 4 months post hiPSC-Fibroblast transplant on the gridwalking task, whereas with the hiPSC-NPCs and hiPSC-GEPs there was a statistically significant improvement over time. (FIG. 20, panel B, * P<0.05).

These findings suggest that functional recovery after hiPSC-NPCs or hiPSC-GEPs treatment is causally associated with the cell type transplanted. To test this idea directly, we employed a system to ablate the transplanted cells. We administered diphtheria toxin (DT) 4 months post-stroke to ablate all grafted hiPSC-NPCs and hiPSC-GEPs. DT binds to the heparin binding epidermal growth factor precursor, which is present on human cells but not rodent cells and has been used to selectively ablate human cell transplants in the brain in rodent models (31). In these studies, DT produced complete loss of the hiPSC-derived NPCs and GEPs after transplantation (FIG. 20, panels C, D and FIG. 29). DT-mediated hiPSC-NPC ablation abolished the partial beneficial effects on motor recovery (FIG. 20, panels C, D). However, in mice with DT-mediated hiPSC-GEP ablation, the beneficial recovery effects persisted: DT treated mice that recovered with hiPSC-GEP transplantation did not deteriorate when hiPSC-GEPs were ablated. These data suggest that transplanted hiPSC-GEPs induce a local repair response and recovery of motor control. Once this repair response is in place, hiPSC-GEPs do not need to be present in the brain to maintain the recovered motor control. In contrast, hiPSC-NPCs are actively mediating the mild recovered motor control, perhaps through their local connections, and ablation of these cells causes a reduction the recovered motor control after stroke.

With the greater effect of hiPSC-GEPs on motor recovery after WMS, we determined if hiPSC-GEP transplantation resolves the cognitive decline observed after WMS damage by testing mice in two cognitive-memory tasks, novel object recognition and fear conditioning (FIG. 20, panels E, F). Whereas the WMS group continued to exhibit poor performance compared with the non-stroke group of mice, the WMS group transplanted with hiPSC-GEPs showed statistically significant cognitive improvement 4 months post-stroke in both memory tests (FIG. 20, panels E, F, *, # P<0.05).

Mechanisms of White Matter Repair

In order to determine the key cell-specific mechanisms of repair during WMS, we compared the gene expression profile of the in vitro cultured hiPSC-GEPs 3, 6 and 120 days after DFX treatment. We overlaid differentially expressed genes (DEGs) between hiPSC-GEPs and the parent line hiPSC-NPCs, with genes induced in pro-inflammatory astrocytes and pro-repair astrocytes (37), respectively (FIG. 21, panels A-C). Overall transcriptome profiling suggested that hiPSC-GEP-induced genes are significantly enriched for "pro-repair" astrocyte specific genes i=11 stages, with the p-value <0.01 for 3-day and 4-month, and p<0.03 for 6-day (hypergeometric test) (FIG. 21, panels A-C). In contrast, the overlap between genes induced in hiPSC-GEPs and "pro-inflammatory" astrocytes show no overlap in all time points (FIG. 21, panels A-C). The trend is further illustrated by a heatmap of representative genes for pan-reactive astrocyte, "pro-inflammatory", and "pro-repair" astrocytes, showing that hiPSC-GEP-derived astrocytes are representatives of a "pro-repair" specific astrocytes (FIG. 21, panel G). Among the most upregulated genes, Galectin-3 (LGALS3), Sphingosine kinase 1 (SPHK1) (p<0.01) (FIG. 21, panels D-F), and transcription factor EGR2 (FIG. 25), are promyelination genes that could explain the increased myelination in the hiPSC-GEP group. Galectin-3 has a critical role in driving oligodendrocyte differentiation (38) and myelination (39). SPHK1 plays a crucial role in the stimulation of oligodendrocyte progenitors (40). EGR2 has been reported to transcriptionally up-regulate Myelin Protein Zero (MPZ), which is the most abundant protein component mature myelin (41). Moreover, mutations in EGR2 gene have been reported in a variety of severe demyelinating neuropathies, including autosomal recessive congenital hypomyelinating neuropathy, autosomal dominant child-onset Dejerine-Sottas neuropathy, and autosomal dominant adult-onset Charcot-Marie-Tooth disease (42).

Other induced genes, such as S100A10 and GDF15, have neuroprotective functions. S100A10 is a key molecule in increasing total neuron dendritic length and spine density (43). GDF15 promotes survival of lesioned dopaminergic neurons following cortical lesion (44) and improves axonal and sensory recovery after peripheral nerve injury (45).

On the other hand, the most downregulated gene in the 3 different time points of, early, mid and late glial enriched development is Transglutaminase 2 (TG2), with a more than 8-fold reduction in hiPSC-GEPs than hiPSC-NPCs (FIG. 21, panels D-F). Overexpression of TG2 in neurons supports survival and protects against oxygen and glucose deprivation-induced cell death and results in a reduction in infarct volume subsequent to stroke (46). However, the effect of TG2 in astrocytes is completely the opposite. Deletion of TG2 in astrocytes increases their survival after ischemia, and reduced stroke volumes (47). The significant ($p=3.2\times10^{-6}$) downregulation of TG2 in hiPSC-GEPs, a cell type that is astrocytic by gene expression and in vivo phenotype, may promote astrocyte survival after transplantation. This transcriptional analysis has determined that we have not only produced a general hiPSC-astrocyte-like cell, we have specifically produced a "pro repair" type cell that has a beneficial effect on all cell types in the stroke lesion, including myelinating oligodendrocytes, neurons, and astrocytes.

The in vitro transcriptional analysis has allowed us to create a panel of the most relevant growth factors that may be involved during white matter repair. Among the most upregulated growth factors are: FGF2, CXCL1, GDF15 and VEGF. All of these growth factors promote oligodendrocyte proliferation, neuronal survival or axonal recovery after injury (FIG. 22, panel A) (45,48-50). The most abundantly expressed and downregulated growth factor in the hiPSC-GEP transcriptome is CTGF, which negatively regulates myelination (FIG. 22, panel A) (51).

To understand mechanistic links between these differentially expressed growth factors and the two aspects of tissue repair after white matter stroke, OPC differentiation and axonal sprouting, we developed axonal growth and OPC differentiation assays.

In mouse primary cortical neurons, Growth and Differentiation Factor 15 (GDF15), C-X-C Motif Chemokine Ligand 1 (CXCL1) and Vascular Endothelial Growth Factor (VEGF) produced an increase in axonal outgrowth, with the doses of 10 ng/mL, 50 ng/mL and 100 ng/mL respectively (FIG. 22, panels B, C). Simultaneously, in mouse isolated OPCs FGF2, GDF15, CXCL1 and VEGF enhanced oligodendrocytes proliferation and differentiation (FIG. 22, panel D). In contrast, the addition of CTGF (long/mL) in either mouse primary cortical neuron or mouse isolated OPC cultures inhibited not only axonal growth but oligodendrocyte proliferation and differentiation (FIG. 22, panels B-D).

To determine the importance of cell-to-cell interaction in axonal growth and oligodendrocyte differentiation after WMS, first, we co-cultured mouse OPCs with either hiPSC-NPCs or hiPSC-GEPs. Whereas the presence of hiPSC-NPCS increased the expression of PDGFRa in the co-culture system, indicating enhanced oligodendrocyte proliferation (FIG. 22, panel E), the presence of hiPSC-GEPs not only enhanced oligodendrocyte proliferation but increase oligodendrocyte differentiation as observed by the high expression of myelinated oligodendrocyte markers (GPR17 and MBP) (FIG. 22, panel E). Lastly, we co-cultured mouse primary neurons with either hiPSC-NPCs or hiPSC-GEPs. The presence of hiPSC-NPCs in the co-culture system induced axonal growth, but the presence of hiPSC-GEPs cells in the coculture system produced an axonal growth 4 times larger than any of the other conditions tested. This condition had the greatest effect in promoting axonal growth among all the conditions tested (FIG. 22, panels B, C).

In conclusion, we were able to narrow down a list of potential key genes and growth factors involve in the mechanisms of repair after WMS due to hiPSC-GEPs transplant.

Discussion

This study demonstrates a unique glial repair stem cell therapy for a common, progressive and as yet untreatable form of stroke and dementia in a rodent model.

By treating hiPSC-NPCs with a short exposure to HIF activation, the cells become permanently biased to differentiate predominantly into pro-repair astrocytes. This process allows rapid, efficient, and clinically viable production of hiPSC-GEPs. Many other protocols for the glial differentiation of iPS cells involve long and labor-intensive processes that are inefficient and not well suited for the number of cells needed for a clinical therapy (24).

Stroke triggers limited neural repair by inducing new connections to form in motor areas (axonal sprouting), triggering immature neurons to migrate to areas of damage (neurogenesis), inducing angiogenesis, and promoting division and partial differentiation of oligodendrocyte progenitor cells (OPCs). This has been studied moist in cortical stroke models (35,36) Compared to cortical stroke, WMS is not associated with a substantial repair process. OPCs respond to WMS with proliferation but not substantial differentiation into mature oligodendrocytes (20,52). Adjacent WM is partially damaged in WMS, and the initial lesion expands over time.

A lack of differentiation of OPCs in this tissue adjacent to stroke renders affected axons susceptible to progressive degeneration (7,20). Lesion expansion is reflected in the progressive neurological deficits of vascular dementia: motor and cognitive dysfunction. In the present WMS model, a similar progression in motor and cognitive deficits is seen. These data suggest that an exogenous cellular therapy to promote WM repair in humans, and through modeling in mice, may bypass inherent limitations of OPC differentiation, and lead to WM repair in this disease.

Previous studies of CNS cellular therapies have utilized mesenchymal stromal cells, fetal neural progenitors and ES/iPS-derived neural progenitors, which show limited repair capacity (31,55). This study reports differences in survival rates, differentiation, effects on myelin and axonal connections between IPSC and other stem cell therapies after WMS.

In terms of tissue repair, hiPSC-GEPs migrated widely in the brain and promoted OPC differentiation and WM repair by measures of mature oligodendrocytes, myelin staining and MRI. hiPSC-GEP transplantation also promotes the formation of connections between brain areas. WMS occurs in the brain region that connects the two brain hemispheres, damaging axons in the subcortical WM and corpus callosum. hiPSC-GEP transplantation after WMS induced new connections to from across this damage, establishing links between sensorimotor cortical areas. In contrast, hiPSC-NPCs remained localized to the transplant site, differentiated into neurons within the WM where such neurons do not normally exist, and formed local axons. hiPSC-GEPs promoted greater motor recovery than hiPSC-NPCs and enhanced cognitive recovery after WMS. This Recovery occurred in measures of gait, forelimb motor use and memory. An important comparison in these studies was across several hiPSC-derived cell lines, such as the parent hiPSC-NPCs, as well as a comparator line of hiPSC-fibroblasts. This comparison controlled for secreted and cell-contact effects that might arise from simply placing a progenitor cell into damaged brain, vs. a specific effect of, in this case, transplanting an immature astrocyte line. This greater effect of an hiPSC-GEP transplant on behavioral improvement suggests specific mechanisms of action unique to this cell type: astrocyte differentiation and vascular association, local induction of oligodendrocyte responses and myelin repair, and axonal sprouting. Further, ablating hiPSC-GEPs did not reduce this enhanced recovery, suggesting that these cells induced local or endogenous responses and secreted growth factors rather than directly participating in tissue repair. This is unlike hiPSC-NPCS, in which cell ablation reduced the recovery effect.

Astrocytes during CNS development, in culture systems and in non-stroke CNS lesions promote OPC proliferation and differentiation (13-15). Transplantation of exogenous glial progenitors or immature astrocytes has promoted tissue repair and re-myelination in spinal cord injury models, genetic WM diseases and multiple sclerosis and radiation models (16). Here, we observed similar results with distinct methods. These results implicate a potential strategy for promoting myelinogenesis and axonal sprouting, through hiPSC-derived progenitors capable of generating astroglia. Having the means to extensively regenerate and re-myelinate projections after WMS provides an important tool for both future clinical developments and for elucidating our understanding of the mechanisms that underlie regeneration. Further studies to characterize the unique molecular systems that are active in this cell type in vivo, and could affect fate decisions after transplantation, remain to be addressed and will shed light on the mechanism by which hiPSC-GEPs repair the damaged brain after stroke.

This set of studies has several limitations. The two possible mechanisms of action of transplanted hiPSC-GEPs are in axonal sprouting and remyelination. At present, these two biological processes are not directly assessed with gain and loss of function, and then functional outcome measures, which will be an area of future study. To further translate this approach, future studies will need to examine the effect of hiPSC-GEP transplantation in aged animals, distinct time points and sites of injection (such as near the stroke vs into distant sites) and different doses.

Collectively, these studies were carried out on immunocompromised mice (NSGs). The use of immunocompromised mice, although a desirable for successful engraftment of human cells, may alter the endogenous response to white matter stroke. Future studies will pursue the use of engineered hiPSC-GEP lines that can avoid rejection and be used as an allogenic cell-based therapy for white matter stroke.

Methods

Study Design.

The main goal of this study is to reveal the different cellular and molecular mechanisms that stimulate neurological rescue involved in white matter repair due to an astrocytic therapy after white matter stroke/vascular dementia. To develop this goal, a stroke model in the mouse was developed that resembles human vascular dementia. A candidate stem cell line, hiPSC-GEPs, was then characterized for its in vitro molecular and cellular characteristics as a glial cell replacement therapy, with astrocyte predominance, in white matter stroke. This line was then tested in transplantation into the mouse white matter stroke model, at a subacute time period after stroke (7 days) with tissue and behavioral outcome measures of hiPSC-GEP transplantation. The tissue outcome measures were designed to test the effect of hiPSC-GEP transplantation on OPC proliferation and differentiation, myelin structure, axonal connections and then behavioral recovery. Mice were randomly allocated to treatment condition using a randomized block experimental design (restricted randomization) and all results were analyzed with the investigator blinded to treatment condition. The required number of animals per group was determined by a power analysis as demonstrated by similar experiments (7,20,21, 32,35,52): 6 animals in the tissue/MRI studies and 12 animals in the behavioral studies are allocated per group to achieve statistical thresholds to detect a statistically significant result in ANOVA with a=0.05 and power >0.8 in each independent experiment performed. We have performed 6 independent in vivo experiments (N=6) and 3 independent cell culture experiments (N=5), n=3-6 replicates each.

Mice.

All experiments were performed in accordance with National Institutes of Health animal protection guidelines and were approved by the University of California, Los Angeles Chancellor's Animal Research Committee. 2-3-month-old male Nod SCID gamma (NSG) (Jackson Laboratories) mice were used in this study.

White-Matter Stroke

WMS in the mouse was modified from (7, 20, 21,52). Briefly, a craniotomy was performed overlying the injection sites of the cortex while the mice were anesthetized with 2% isoflurane in 2:1 N2O:O2, and securely mounted onto a stereotaxic apparatus. Core body temperature of the mice was maintained at 36.5-37.5° C. A Hamilton syringe was filled with L-NIO (27 microg/microL in sterile physiological saline; Calbiochem), secured onto the stereotaxic arm and connected to a pressure pump. To avoid damage to motor cortex, the syringe containing the L-NIO was inserted through the cortex of the frontal lobe into the underlying WM at an angle of 36 degrees. Three injections (each of 0,3 microL L-NIO solution) were made in the following coordinates: AP+0.14, ML+2.33, DV −1.3; AP+0.14, ML+3, DV −1.32; and AP+0.14, ML+3.66, DV −1.4. Injections were made at a rate of 3 microL/minute, targeting subcortical WM. Localized vasoconstriction leads to focal ischemia in the subcortical WM (7,20,21,52).

iPS Transplant.

Surgical procedures were as in the stroke production. Cells were stereotaxically transplanted 7 days after stroke. A Hamilton syringe was filled with iPS-GEPs, iPS-NPCs or iPS-Fibroblast secured onto the stereotaxic arm and connected to a pressure pump. Two 0.45 pl injections of iPS-GEPs, iPS-NPCs or iPS-Fibroblast were given (100,000 cells/microL) at an angle of 36° in the following coordinates: AP +0.14, ML +2.66, DV −1.32 and AP +0.14, ML +3, DV −1.32.

Immunohistochemistry.

Animals were perfused transcardially with 0.1M phosphate buffered saline followed by 4% paraformaldehyde. The brains were removed, postfixed overnight in 4% paraformaldehyde and cryoprotected for 2 days in 30% sucrose and frozen Brain tissue was sectioned into parallel series of 40 pm sections 200 pm apart (Leica CM 0530).

Immunostaining for hGFAP, mGFAP, IBA-1, NF200, GFAP, Olig2, MBP and hDCx, mDCX, S100P, GLUT-1, NeuN, CC1 and GSTn to sections was done by blocking in 5% normal donkey serum for 1 hour at room temperature, incubating in primary antibody overnight at 4 degrees Celsius, and in secondary antibody for 1 hour at room temperature. All antibodies are listed in Table 4.

TABLE 4

Antibodies used in immunohistochemical staining (IHC).

| Antibody | Host | Vender | Concentration |
|---|---|---|---|
| GFAP | rat | Invitrogen | 1:500 |
| hGFAP | rabbit | Abcam | 1:500 |
| MBP | rat | Abcam | 1:500 |
| hMBP | rabbit | Abcam | 1:500 |
| NF200 | rabbit | Sigma | 1:500 |
| Iba1 | rabbit | Wako | 1:500 |
| Olig2 | rabbit | Millipore | 1:500 |
| DCX | goat | Santa Cruz | 1:500 |
| hDCX | rabbit | Hagen Inc | 1:500 |
| CC1 | mouse | Abcam | 1:500 |

TABLE 4-continued

Antibodies used in immunohistochemical staining (IHC).

| Antibody | Host | Vender | Concentration |
|---|---|---|---|
| GSTpi | goat | Abcam | 1:500 |
| S100B | rabbit | Swat | 1:500 |
| S100B | mouse | Sigma | 1:1000 |
| NeuN | mouse | Millipore | 1:500 |
| NeuN | rabbit | Abcam | 1:1000 |
| Pax6 | rabbit | Biolegend | 1:300 |
| Sox2 | goat | Santa Cruz | 1:200 |
| Ki67 | rabbit | Abcam | 1:500 |
| Tuj1 | rabbit | Abcam | 1:1000 |
| MAP2 | chicken | Abcam | 1:200 |
| NeuN | chicken | Synaptic Systems | 1:500 |
| mTau | mouse | Sigma | 1:1000 |

In Vitro.

Immunofluorescent staining was performed as described (18). Briefly, cells grown on coverslips were fixed at indicated time points with 4% (w/v) paraformaldehyde (Electron Microscopy Sciences) in PBS. Antibodies include the following: chicken anti-GFAP (Abcam), mouse anti-MAP2 (Abcam), mouse anti-NESTIN (Neuromics). More than six views were randomly selected for each coverslip, and images were taken at 10× magnification with the same exposure time across all samples. Quantification was performed (ImageJ) with the same threshold for each channel for all samples. The percentage of neurons or astrocytes was calculated with a positive staining area from each marker and normalized based on cell number (DAPI staining). P-value was calculated with Student's t test.

In Vitro Primary Cortical Neurons and Co-Culture.

All conditions of primary mouse neuron studies were fixed using 8% paraformaldehyde Electron Microscopy Sciences) in PBS. Antibodies used include the following chicken anti-NeuN (Synaptic Systems), rabbit anti-beta III tubulin (Abcam), mouse anti-tau 1 (Sigma), and DAPI (ThermoFisher).

More than 300 images per well were taken at 20× magnification with the same parameters for scanning across all wells. NIS— Elements JOBS acquisition and analysis designer software performed 3D analysis of cell number and length of dendritic outgrowth with the same threshold for each channel for all wells.

Confocal Images.

High-resolution confocal images in Z-stacks were acquired (Nikon C2). Area measurements of the infarct core, IBA-1, GFAP, S100P, NeuN and DCX positive cells were stereologically quantified using the optical fractionator probe and neuroanatomical quantification software (Stereo-investigator, MBF Bioscience). WM axonal projections stained with NF200 and MBP were quantified with intensity profiles (ImageJ, NIH). For endogenous oligodendrocyte differentiation studies (Olig2, CC1 and GSTn positive cells) large scale image of the entire WM was acquired using a 20× objective with confocal microscopy (Nikon C2). The parameters for scanning were kept constant across treatment conditions and 3D analysis of cell number and spatial relationships was performed (Imaris, Bitplane, Version 8.1.1).

GFP fluorescence quantification was used to map the iPS-transplanted cells, 4 months post-transplant in a series of six sections 200 pm apart (DMLB microscope, Leica Microsystems). iPS cells were digitally quantified using neuroanatomical quantification software (StereoInvestigator, MBF Bioscience).

For the vascular interaction studies large scale images of the entire section were acquired using a 20× objective with confocal microscopy (Nikon C2). The distance between single iPS cells to the closet blood vessel (GLUT-1) vessel was measured (Imaris, Bitplane, Version 8.1.1).

Cell Culture hESCs and hiPSCs were cultured as described previously (17,18) in accordance with UCLA Embryonic Stem Cell Research Oversight committee. Briefly, feeder-free hiPSC lines were maintained with mTeSR1 (Stem Cell Technologies) and passaged mechanically. Neural rosette derivation, NPC purification, and differentiation into neurons and glia were performed as described (17,18). Rosettes were generated by growing PSCs for at least 7 days in Dulbecco's modified Eagle's medium (DMEM)/F12 with $N_2$ and B27 supplements (Invitrogen), 20 ng/ml basic fibroblast growth factor (FGF) (R&D Systems), 1 mM retinoic acid (RA) (Sigma), and 1 mM Sonic Hedgehog Agonist (Calbiochem). hiPSC-NPCs were expanded in NPC medium containing DMEM/F12, N2 and B27, 20 ng/ml basic FGF, and 50 ng/ml EGF (GIBCO) once the rosettes were picked. DFX (Sigma) (100 to 200 mM) and DMOG (Sigma) (250 mM) were added at the NPC stage for 3 to 5 days. Upon differentiation, EGF and FGF were withdrawn from NPC medium for 2 to 6 weeks. Physiological oxygen tension growth was established in 2% O2, 5% CO2, and 92% N2. Atmospheric oxygen tension growth was established in 20% O2, 5% CO2, and 75% N2. The generation of fibroblasts from PSCs was performed as described (17, 18). Briefly, PSCs were converted into embryoid bodies (EBs) by collagenase dissociation and culture in non-adherent dishes in PSC medium lacking FGF. After 5 days, the EBs were plated in Fibroblast medium (DMEM+10% Fetal Calf Serum). After 7 days in Fibroblast medium, fibroblast clones grew out from the adherent EBs and clones were manually dissociated and plated into new pates in Fibroblast medium.

Gene Expression Analysis

RNA extraction, reverse transcription and real-time quantitative PCR were performed as described (18). Briefly, total RNA was isolated using a RNeasy Mini Kit following protocol described by the manufacturer (QIAGEN). Reverse transcription and real-time PCR were performed using the Superscript III first-strand cDNA synthesis kit (Invitrogen) and the SYBR green real-time PCR kit (Roche), respectively. Transcripts expression were determined in triplicate reactions and normalized to housekeeping gene such as beta-actin. Primer sequences are available upon request.

RNA Sequencing

Total RNA was isolated using a RNeasy Mini Kit (QIAGEN). Library preparation was performed using TruSeq Standard RNA LT Kit (Illumina) following the standard total RNA sample preparation protocol. The sequencing reactions were run on HiSeq 2000 as single-end 100 bp.

RNA Sequencing Analysis

Tophat was used to align reads to the hg19 genome assembly using the default settings in Galaxy (http://galaxy.hoffman2.idre.ucla.edu). Multimappers, unmapped reads, and low-quality alignments were excluded from analysis. Counts obtained using featureCounts with Gencode annotations were analyzed with the R package edgeR, which uses a negative binomial generalized log-linear model. In order to identify genes that were consistently up- or down-regulated across all hypoxia-inducing treatments, the hypoxia-inducing conditions 2% O2, DFX and DMOG were treated as replicates. This way, genes modulated by only one treatment are penalized by potential variation across the three hypoxia-inducing conditions. An unadjusted p-value threshold of 0.05 was imposed for the likelihood ratio test to select differentially expressed genes. The gene ontology categories were generated with DAVID bioinformatics resources using functional annotation clustering with default settings. RNA sequencing data has been deposited to a publicly available database: https://www.ncbi.nlm.nih-.gov/geo/query/acc.cgi2acc5GSE61842).

Axonal Sprouting.

Mice received WMS and WMS+iPS treatment procedures as above (n=6 per group). 4 months after iPS-transplant or stroke alone, mice received a microinjection of the axonal tracer BDA (0.3 pl) in forelimb motor cortex rostral to the stroke site. Mice survived 1 week after tracer injection and tissue was processed for densitometric analysis of axonal label in coronal tissue sections using fluorescence measurement methods (35). Axonal sprouting was quantified by digitally marking each BDA positive process in the cortex with a digitizing microscope system (Leica Microsystems, Ludl Electronic Products) and analysis program (Stereoinvestigator, MBF Biosciences).

MIR

Mice were anesthetized and placed in a Bruker 7T small animal MRI (Bruker Biospin). MRI imaging was performed on days 0, 7 and 6 months after stroke. Respiratory rate was monitored throughout the procedure and body temperature was maintained at 37±0.5° C. T2-weighted images were acquired (rapid acquisition relaxation enhancement factor 8, repetition time 5300 ms, echo time 15.00 ms with an in-plane resolution of 0.0156_0.0156_0.50 mm with 13 contiguous slices).

Tractography, diffusion tensor data (DTI) analysis images were acquired at 0, 7 and 6 months after treatment with a spin echo single shot echo planar imaging (EPI) pulse sequence(TR/TE: 5000/35 ms; a signal average of 10, a 30 noncolinear diffusion gradient scheme with diffusion weighting of b=1000 s/mm2 and b=0 s/mm2, and field of view 3.5×3.5 cm_. The data was acquired using 30 directions with a single shot EPI sequence on a 96×96 matrix, and zero-filled k-space to construct a 128×128 image matrix. Images were obtained with Medlnria, a multi-platform medical image processing and visualization software. DTI tractography data was performed in the lesion zone using n=6 animals per group and images (ParaView 4.1.0, Kitware, Inc.).

Electron Microscopy

A separate cohort of animals was used for electron microscopy, following the same stroke and hiPSC-derived injection protocol as outlined above (n=5 per group). Tissue was perfused using 2% PFA/2.5% glutaraldehyde in 0.1 m phosphate buffer, dissected and immersed in the same fixative, then cut sagittally on a brain block in 1 mm sections, and a rectangle ~1 mm×2 mm was cut from the brain slice surrounding the stroke area. This was sent to the University of Colorado Denver Anschutz Electron Microscopy Center for further processing. Briefly, the tissue was rinsed in 100 mM cacodylate buffer and then immersed in 1% osmium tetroxide and 1.5% potassium ferrocyanide for 15 min. Next, the tissue was rinsed five times in cacodylate buffer, immersed in 1% osmium for 1 h, and then rinsed again five times for 2 min each in cacodylate buffer and two times briefly in water. The tissue was transferred to graded acetone (50%, 70%, 90%, and 100%) containing 2% uranyl acetate for 15 min each. Finally, the tissue was transferred through acetone/resin mixtures at room temperature and then embedded in EMbed-812 and cured for 48 h at 60° C. in an oven.

Imaging regions were determined using semithick sections (1 micron) stained with toluidine blue. Ultrathin sections (65 nm) were then cut on a Reichert Ultracut S from a small trapezoid positioned over the area of interest and were picked up on Formvar-coated slot grids (EMS). Sections were imaged on a Technai G2 transmission electron microscope (FEI) with a digital camera (AMT), and 100 $pm^2$ images were obtained at 11,000*. Two fields per animal were analyzed using National Institutes of Health ImageJ software. To calculate g ratios, inner and outer borders of myelin were drawn for each axon totally captured within the image field, and the ratio of inner (axon) to outer (myelin) border was calculated. Separately, total numbers of myelinated and unmyelinated axons were counted per field. Metrics were averaged within each animal, and these animal averages were used for statistical analyses.

Behavioral Assessment

Mice (12 per group) were tested once on the grid-walking and cylinder tasks 1 week before surgery to establish baseline performance. Animals were always tested during the first three hours of their dark cycle. Tests were done at week 1, 4, 8 and 16, after stroke. Treatments were administered as for the axonal sprouting studies: Control, WMS-only, WMS+iPSC-GEPs, WMS+iPSC-NPCs and WMS+iPSC-Fibroblast. Behaviors were scored by observers who were masked to the treatment group of the animals. During Fear conditioning testing mice were exposed to a context for 3 minutes, shocked 3 times with a 0.75 mAmp during 2 second and shock with an ITI for 1 minute for training. They remained in the context for another 3 minutes. A WMS was performed after contextual training. 24 hours post-WMS, mice returned to the context for 4 minutes to assess their memory of the training event. They will be returned for an additional 4 minutes test 7 days, 30 days and 120 days post-stroke. NOR was perform after 4 months post-stroke. An open field arena (TSE Systems) was used for testing. During the testing, the time to explore the objects was recorded and analyzed by Videomot2 (TSE Systems). In brief, for novel objectpreference task, mice were allowed to habituate twice in the arena with two identical objects for 5 minutes. Then the mice were placed in the arena for 3 minutes with one novel object and one familiar object. The data was presented as exploration ratio or ratio of time spent exploring the novel object versus both objects. Assessment on the grid-walking, cylinder, NOR and fear conditioning tasks were performed as previously described (13,16).

Cell Ablation.

Cell ablation experiments were performed as described previously (31,54). Briefly, sixteen weeks after WMS, DT solution (50 pg/kg, Sigma) or vehicle was administered to mice by intraperitoneal injection, daily for two days. Mice were reassessed for behavioral tests within one week of DT or vehicle administration and sacrificed for histological analysis. The DT dosing regimen as used in the present study did not lead to any functional deficits or structural changes after WMS in control mice treated only with DT consistent with previous reports in control mice in other models of neurological disorders treated with DT.

Mouse Primary Cortical Neuron Extraction.

Primary mouse neurons were extracted from P2 to P4 NSG mice pups using the mouse and rat Adult Brain Dissociation kit (MACS Miltenyi Biotec). Mouse neurons extracted were grown at the density of 100,00 cells per well in a 24 well flat bottom microplate (Greiner Bio-One) coated with Matrigel (Corning). Neurons were cultured in NbActiv4 media (BrainBits) supplemented with penicillin-streptomycin (ThermoFisher), media changed once the day after extraction.

Mouse Primary Cortical Neuron Growth Factor Treatment.

For growth factor treatment studies primary mouse neurons were plated at the density of 100,000 cells/1.9 cm$^A$2 and cultured in NbActiv4 media for three days. Following this, growth factors were added to fresh culture media. Growth factor treatments included FGF2 (5 ng/mL-Sigma), CTGF (10 ng/mL-Sigma), GDF15 (10 ng/mL-Sigma), VEGF (10 ng/mL-Sigma), CXCL1 (50 ng/mL-Sigma). Low, medium and high concentrations for each of the growth factors are specified as follows: 5 ng/mL FGF2; 10 ng/mL CTGF; 10 ng/mL GDF15; 10 ng/mL VEGF; 50 ng/mL CXCL1. All growth factors were diluted as specified from manufacturer. After addition of all growth factor treatments, mouse neurons were incubated for 3 days. Cells were fixed with 8% paraformaldehyde for 20 mins and left in 1×PBS at 4° C.

Primary Mouse Neuron Co-Cultures.

Primary mouse neurons were plated at the density of 100,000 cells/1.9 cm$^A$2, for coculture studies hiPSC-NPCs and hiPSC-GEPs were seeded with the mouse neurons. hiPSC-NPCs were plated with the mouse neurons at the concentration of 10,000 cells/1.9 cm$^A$2 and 50,000 cells/1.9 cm$^A$2. The same procedure was completed with the hiPSC-GEPs. After incubation overnight, NbActiv4 media was changed to fresh media the following day. After 6 days in culture, coculture plates were fixed with 8% paraformaldehyde for 20 mins and left in 1×PBS at 4×.

Purification of Mouse Oligodendrocyte Progenitor Cells (OPCs)

OPCs were purified from postnatal NSG mice brains by immunopanning as described previously (55). Brains were harvested by dissection from P7 NSG mice and dissociated enzymatically with papain. Post dissociation, cells were rinsed and passed sequentially over a series of petri dishes coated with the following antibodies: Thy 1.2 antibody (Serotec) to remove astrocytes, O1 antibody (Millipore) to remove oligodendrocytes and O4 antibody (Millipore) to select for OPC's. The purified OPCs were harvested off the O4 plate with trypsin and then plated on Matrigel coated 6 well tissue culture plates. The serum-free growth culture media contained DMEM (Invitrogen) supplemented with glutamine (200 mM; Invitrogen), Penicillin streptomycin (Gibco/Life Technologies), Sodium pyruvate (100 mM; Invitrogen), Insulin stock (0.5 mg/mL; Sigma-Aldrich), N-Acetyl-L-cysteine stock (5 mg/mL; Sigma-Aldrich), Trace Elements B (1000*; Cellgro), d-Biotin stock (50 pg/mL; Sigma-Aldrich), BSA (10 mg/mL; Sigma-Aldrich), Transferrin (10 mg/mL; Sigma-Aldrich), Putrescine (1.6 mg/mL; Sigma-Aldrich), progesterone (6 ug/mL; Sigma-Aldrich), sodium selenite (4 ug/mL; Sigma-Aldrich), Forskolin stock (4.2 mg/mL; Sigma-Aldrich), CNTF stock (10 pg/mL; Peprotech).

Purified Mouse OPC Growth Factor Treatment

For growth factor treatment studies, purified mouse OPCs collected by immunopanning were plated at the density of 200,000 cells/9.6 cm$^A$2 and cultured in serum-free growth culture media for 1 day. Following this, growth factors were added to fresh serum-free growth culture media. Growth factor treatments included FGF2 (Sigma), CTGF (Sigma), GDF15 (Sigma), VEGF (Sigma) CXCL1 (Sigma). A medium concentration for each of the growth factors are specified as follows: 5 ng/mL FGF2; 10 ng/mL CTGF; 10 ng/mL GDF15; 10 ng/mL VEGF; 50 ng/mL CXCL1. All growth factors were diluted as specified from manufacturer. After addition of all growth factor treatments, mouse OPCs were incubated for 6 days. Cells were harvested of plate with trypsin, centrifuged at 1000 RPM for 5 mins and resuspended in serum-free growth media to be counted.

Purified Mouse OPC Co-Cultures

Purified mouse OPCs collected by immunopanning were plated at the density of 100,000 cells/9.6 cm$^A$2, for co-culture studies hiPSC-NPCs and hiPSC-GEPs were seeded with the purified mouse OPCs. hiPSC-NPCs were plated with the mouse OPCs at the concentration of 100,000 cells/9.6 cm$^A$2. The same procedure was completed with the hiPSC-GEPs. After incubation overnight, serum-free growth culture media was changed to fresh media the following day. After 6 days in culture, co-culture cells were harvested with trypsin, centrifuged at 1000 RPM for 5 mins, and resuspended in serum-free growth culture media to be counted.

Quantitative Real-Time PCR.

Samples of messenger ribonucleic acid (mRNA) for quantitative real-time polymerase chain reaction (q-RT-PCR) were obtained as previously described (56). Briefly, total RNA was extracted using the Zymo Research Quick-RNA Microprep Kit. The high-capacity complementary deoxyribonucleic acid (cDNA) reverse transcription kit (Applied Biosystems, Foster City, CA, USA) was used to perform reverse transcription following the manufacturer's instructions. Reactions were carried out for 10 min at 25° C., 2 h at 37° C. and heated to 85° C. for 5 s to end the reaction.

Real-time PCR was carried out on a Roche LightCycler 480 Instrument II. A LightCycler 480 SYBR Green I Master Mix (LifeScience, Roche) was used, and the following settings were programmed: 1 cycle of 30 s at 95° C., 40 cycles of 10 s at 95° C., 30 s at 60 C, and 30 s at 72° C., 1 cycle of 5 s at 95 C, 1 min at 65 C, and continuous at 97° C., and 1 cycle of 30 s at 40° C. Cycle thresholds (Ct) for the different genes were selected immediately above the baseline and within the linear range on the log scale. Each reaction (10 pL) was made using 5 nM of each primer, 1 pL cDNA aliquot, 5 pL of SYBR® Green PCR Master Mix and 3.4 pL of $H_2O_2$ molecular grade water.

Increases in fluorescence of SYBR® Green during the amplification process were analyzed with Sequence Detector software (Roche). Fold changes for the different comparisons were expressed as (2−ACt), where ACt=Cttarget−CtGAPDH) (57). Ct values correspond to the cycle number at which the fluorescence signal crossed the designated threshold. Experiments were performed in accordance with the Minimum Information for Publication of Quantitative Real-time PCR Experiments (MIQE) guidelines (58).

Statistical Analysis

Mice were randomly allocated to treatment condition using a randomized block experimental design (restricted randomization) and all results were analyzed with the investigator blinded to treatment condition. The required number of animals per group was determined by a power analysis as demonstrated by similar experiments (7,20,21,32,35,52): 6 animals in the tissue/MRI studies and 12 animals in the behavioral studies are allocated per group to achieve statistical thresholds to detect a statistically significant result in ANOVA with a=0.05 and power >0.8. All data are expressed as mean±SEM. For cell quantification, axonal degeneration, WM measurements and behavioral testing, differences between stroke and treatment groups were analyzed using one-way or two-way Analysis of Variance (ANOVA) with level of significance set at p<0.05, with Tukey's HSD post-hoc analysis (Excel and GraphPad Prism).

REFERENCES

1. E. Matsusue, S. Sugihara, S. Fujii, E. Ohama, T. Kinoshita, T. Ogawa, White matter changes in elderly people: MR-pathologic correlations. *Magn. Reson. Med. Sci.* 5, 99-104 (2006).

2. A. A. Gouw, W. M. van der Flier, L. Pantoni, Inzitari D, Erkinjuntti T, Wahlund L O, Waldemar G, Schmidt R, Fazekas F, Scheltens P, Barkhof F; LADIS study group. On the etiology of incident brain lacunes: longitudinal observations from the LADIS study. *Stroke* 39, 3083-5 (2008).
3. C. ladecola, The pathobiology of vascular dementia. *Neuron* 80, 844-66 (2013).
4. R. Schmidt, S. Seiler, M. Loitfelder, Longitudinal change of small-vessel disease-related brain abnormalities. *J. Cereb. Blood Flow Metab.* 36, 26-39 (2016)
5. G. T. Whitman, Y. Tang, A. Lin, R. W. Baloh, A prospective study of cerebral white matter abnormalities in older people with gait dysfunction. *Neurology* 57, 990-994 (2001)
6. A. Soumare, A. Elbaz, Y. Zhu, P. Maillard, F. Crivello, B. Tavernier, C. Dufouil, B. Mazoyer, C. Tzourio, White matter lesions volume and motor performances in the elderly. *Ann Neurol.* 65, 706-15 (2009)
7. E. G. Sozmen, A. Kolekar, L. A. Havton, S. T. Carmichael, A white matter stroke model in the mouse: axonal damage, progenitor responses and MRI correlates. *J. Neurosci. Methods* 180, 261-72 (2009)
8. H. C. Chui, Subcortical ischemic vascular dementia. *Neurol. Clin.* 25, 717-40 (2007)
9. Y. Lee, B. M. Morrison, Y. Li, S. Lengacher, M. H. Farah, P. N. Hoffman, Y. Liu, A. Tsingalia, L. Jin, P. W. Zhang, L. Pellerin, P. J. Magistretti, J. D. Rothstein, Oligodendroglia metabolically support axons and contribute to neurodegeneration. *Nature* 487, 443-8 (2012)
10. S. Pan, J. R. Chan, Regulation and dysregulation of axon infrastructure by myelinating glia. *J. Cell Biol.* 216, 3903-3916 (2017)
11. R. G. Almeida, D. A. Lyons, On Myelinated Axon Plasticity and Neuronal Circuit Formation and Function. *J. Neurosci.* 37, 10023-10034 (2017)
12. F. Mei, K. Lehmann-Horn, Y. A. Shen, K. A. Rankin, K. J. Stebbins, D. S. Lorrain, K. A. Pekarek, S. Sagan, L. Xiao, C. Teuscher, H. C. von Budingen, J. Wess, J. J. Lawrence, A. J. Green, S. P. Fancy, S. S. Zamvil, J. R. Chan, Accelerated remyelination during inflammatory demyelination prevents axonal loss and improves functional recovery. *Elife* 5 (2007)
13. D. Clemente, M. C. Ortega, C. Melero-Jerez, F. de Castro, The effect of glia-glia interactions on oligodendrocyte precursor cell biology during development and in demyelinating diseases. Front. Cell *Neurosci.* 7, 268 (2013)
14. C. S. Moore, R. Milner, A. Nishiyama, R. F. Frausto, D. R. Serwanski, R. R. Pagarigan, J. L. Whitton, R. H. Miller, S. J. Crocker, Astrocytic tissue inhibitor of metalloproteinase-1 (TIMP-1) promotes oligodendrocyte differentiation and enhances CNS myelination. *J. Neurosci.* 31, 6247-54 (2011)
15. P. Jiang, C. Chen, X. B. Liu, D. E. Pleasure, Y. Liu, W. Deng, Human iPSC-Derived Immature Astroglia Promote Oligodendrogenesis by Increasing TIMP-1 Secretion. *Cell Rep.* 15, 1303-15 (2016)
16. J. Piao, T. Major, G. Auyeung, E. Policarpio, J. Menon, L. Droms, L. Droms, P. Gutin, K. Uryu, J. Tchieu, D. Soulet, V. Tabar, Human embryonic stem cell-derived oligodendrocyte progenitors remyelinate the brain and rescue behavioral deficits following radiation. *Cell Stem Cell* 16, 198-210 (2015)
17. M. Patterson, D. N. Chan, I. Ha, D. Case, Y. Cui, B. Van Handel, H. K. Mikkola, W. E. Lowry, Defining the nature of human pluripotent stem cell progeny. *Cell Res.* 22, 178-193 (2011)
18. Y. Xie, J. Zhang, Y. Lin, X. Gaeta, X. Meng, D. R. Wisidagama, J. Cinkornpumin, C. M. Koehler, C. S. Malone, M. A. Teitell, W. E. Lowry, Defining the role of oxygen tension in human neural progenitor fate. *Stem Cell Reports* 3, 743-57 (2014)
19. C. DeCarli, E. Fletcher, V. Ramey, D. Harvey, W. J. Jagust, Anatomical mapping of white matter hyperintensities (WMH): exploring the relationships between periventricular WMH, deep WMH, and total WMH burden. *Stroke* 36, 50-55 (2005)
20. E. G. Sozmen, S. Rosenzweig, I. L. Llorente, D. J. DiTullio, M. Machnicki, H. V. Vinters, L. A. Havton, R. J. Giger, J. D. Hinman, S. T. Carmichael, Nogo receptor blockade overcomes remyelination failure after white matter stroke and stimulates functional recovery in aged mice. *Proc. Natl. Acad. Sci. U S. A.* 113, E8453-E8462 (2016)
21. E. G. Sozmen, D. J. DiTullio, S. Rosenzweig, J. D. Hinma, S. P Bridges, M. A. Marin, R. Kawaguchi, G. Coppola, S. T. Carmichael S T, White Matter Stroke Induces a Unique Oligo-Astrocyte Niche That Inhibits Recovery. *J Neurosci.* 39, 9343-9359 (2019)
22. G. C. Roman, T. Erkinjuntti, A. Wallin, L. Pantoni, H. C. *Chui*, Subcortical ischaemic vascular dementia. *Lancet Neurol.* 1, 426-36 (2002)
23. M. Batie, J. Frost, M. Frost, J. W. Wilson, P. Schofield, S. Rocha, Hypoxia induces rapid changes to histone methylation and reprograms chromatin. *Science* 363, 12221226 (2019)
24. X. Li, Y. Tao, R. Bradley, Z. Du, Y. Tao, L. Kong, Y. Dong, J. Jones, Y. Yan, C. R. K. Harder, L. M. Friedman, M. Bilal, B Hoffmann, S. C. Zhangm, Fast Generation of Functional Subtype Astrocytes from Human Pluripotent Stem Cells. Stem Cell Reports 11, 998-1008 (2018)
25. K. M. Wilczynska, S. K. Singh, B. Adams, L. Bryan, R. R. Rao, K. Valerie, S. Wright, I. Griswold-Prenner, T. Kordula, Nuclear Factor I Isoforms Regulate Gene Expression During the Differentiation of Human Neural Progenitors to Astrocytes. *Stem Cells* 27, 1173-1181 (2009)
26. P. Kang, H. K. Lee, S. M. Glasgow, M. Finley, T. Donti, Z. B. Gaber, B. H. Graham, A. E. Foster, B. G. Novitch, R. M. Gronostajski, B. Deneen, Sox9 and NFIA Coordinate a Transcriptional Regulatory Cascade during the Initiation of Gliogenesis. *Neuron* 74, 79-94 (2012)
27. Y. Liu, Y. Wu, J. C. Lee, H. Xue, L. H. Pevny, Z. Kaprielian, M. S. Rao, CD44 expression identifies astrocyte-restricted precursor cells. *Dev. Bio.l* 276, 31-46 (2004)
28. A. Shaltouki, J. Peng, Q. Liu, M. S. Rao, X. Zeng, Efficient Generation of Astrocytes from Human Pluripotent Stem Cells in Defined Conditions. *Stem Cells* 31, 941-952 (2013)
29. N. Tiwari, A. Pataskar, S. Peron, S. Thakurela, S. K. Sahu, M. Figueres-Onate, N. Marichal, L. Lopez-Mascaraque, V. K. Tiwari, B. Berninger B, Stage-Specific Transcription Factors Drive Astrogliogenesis by Remodeling Gene Regulatory Landscapes. *Cell Stem Cell* 23, 557-571.e8 (2018)
30. B. H. Dobkin, S. T. Carmichael, The Specific Requirements of Neural Repair Trials for Stroke. Neurorehabil. *Neural Repair* 30, 470-478 (2016)

31. Y. Wang, Z. Zhao, S. V. Rege, M. Wang, G. Si, Y. Zhou, S. Wang, J. H. Griffin, S. A. Goldman, B. V. Zlokovic, 3K3A-activated protein C stimulates postischemic neuronal repair by human neural stem cells in mice. *Nat. Med.* 22, 1050-5 (2016)
32. P. Moshayedi, L. R. Nih, I. L. Llorente, A. R. Berg, J. Cinkornpumin, W. E. Lowry, T. Segura, S. T. Carmichael, Systematic optimization of an engineered hydrogel allows for selective control of human neural stem cell survival and differentiation after transplantation in the stroke brain. *Biomaterials* 105, 145-55 (2016)
33. B. S. Khakh, M. V. Sofroniew, Diversity of astrocyte functions and phenotypes in neural circuits. *Nat. Neurosci.* 18, 942-52 (2015)
34. L. Otero-Ortega, F. Laso-Garea, M. D. Gomez-de Frutos, B. Rodriguez-Frutos, J. Pascual-Guerra, B. Fuentes, E. DAez-Tejedor, M. Gutierrez-Fernandez, White Matter Repair After Extracellular Vesicles Administration in an Experimental Animal Model of Subcortical Stroke. *Sci. Rep.* 7, 44433 (2017)
35. S. Li, E. H. Nie, Y. Yin, L. I. Benowitz, S. Tung, H. V. Vinters, F. R. Bahjat, M. P. Stenzel-Poore, R. Kawaguchi, G. Coppola, S. T. Carmicnhael, GDF10 is a signal for axonal sprouting and functional recovery after stroke. *Nat. Neurosci.* 18, 1737-45 (2015)
36. M. Abematsu, K. Tsujimura, M. Yamano, M. Saito, K. Kohno, J.
Kohyama, M. Namihira, S. Komiya, K. Nakashima, Neurons derived from transplanted neural stem cells restore disrupted neuronal circuitry in a mouse model of spinal cord injury. *J. Clin. Invest,* 120, 3255-3266 (2010)
37. J. L. Zamanian, L. Xu, L. C. Foo, N. Nouri, L. Zhou, R. G. Giffard, B. A. Barres, Genomic analysis of reactive astrogliosis. *J Neurosci.* 32, 6391-6410 (2012)
38. L. A. Pasquini, V. Millet, H. C. Hoyos, J. P. Giannoni, D. O. Croci, M. Marder, F. T. Liu, G. A. Rabinovich, J. M. Pasquini, Galectin-3 drives oligodendrocyte differentiation to control myelin integrity and function. *Cell Death Differ.* 18, 1746-1756 (2011)
39. H. C. Hoyos, M. Rinaldi, S. P. Mendez-Huergo, M. Marder, G. A. Rabinovich, J. M. Pasquini, L. A. Pasquini, Galectin-3 controls the response of microglial cells to limit cuprizone-induced demyelination. *Neurobiol. Dis.* 62, 441-455 (2014)
40. H. S. Saini, R. P. Coelho, S. K. Goparaju, et al. Novel role of sphingosine kinase 1(SPHK1) as a mediator of neurotrophin-3(NTF3) action in oligodendrocyte progenitors. *J. Neurochem.* 95, 1298-1310 (2005)
41. S. E. LeBlane, S. W. Jang, R. M. Ward, L. Wrabetz, J. Svaren J, Direct regulation of myelin protein zero expression by the Egr2 transactivator. *J Biol. Chem.* 281, 5453-5460 (2006)
42. K. Shiga, Y. Noto, I. Mizuta, A. Hashiguchi, H. Takashima, M. Nakagawa, A novel EGR2 mutation within a family with a mild demyelinating form of Charcot-Marie-Tooth disease. *J. Peripher. Nerv. Syst.* 17, 206-209 (2012)
43. S. W. Park, H. Nhu le, H. Y. Cho, M. K. Seo, C. H. Lee, N. N. Ly, C. M. Choi, B. J. Lee, G. M. Kim, W. Seol, J. G. Lee, Y. H. Kim, p11 mediates the BDNF-protective effects in dendritic outgrowth and spine formation in B27-deprived primary hippocampal cells. *J Affect Disord.* 196, 1-10 (2016)
44. J. Strelau, A. Schober, A. Sullivan, L. Schilling, K. Unsicker, Growth/differentiation factor-15 (GDF-15), a novel member of the TGF-beta superfamily, promotes survival of lesioned mesencephalic dopaminergic neurons in vitro and in vivo and is induced in neurons following cortical lesioning. *J. Neural Transm. Suppl.* 65, 197-203 (2003)
45. L. Mensching, A. K. Borger, X. Wang, P. Charalambous, K. Unsicker, K. Haastert-Talini, Local substitution of GDF-15 improves axonal and sensory recovery after peripheral nerve injury. *Cell Tissue Res.* 350: 225-238 (2012)
46. A. J. Filiano, J. Tucholski, P. J. Dolan, G. Colak, G. V. Johnson, Transglutaminase 2 protects against ischemic stroke. *Neurobiology of Disease.* 39, 334-343 (2010)
47. G. Colak, G. V. Johnson, Complete transglutaminase 2 ablation results in reduced stroke volumes and astrocytes that exhibit increased survival in response to ischemia. *Neurobiology of Disease.* 45, 1042-1050 (2012)
48. E. E. Frost, J. A. Nielsen, T. Q. Le, R. C. Armstrong, PDGF and FGF2 regulate oligodendrocyte progenitor responses to demyelination. *J Neurobiol.* 54, 457-472 (2003)
49. KM. Omani, S. E. Lutz, L. Santambrogio, S. A. Lira, C. S. Raine, Neuroprotection and remyelination after autoimmune demyelination in mice that inducibly overexpress CXCL1. *Am J Pathol.* 174, 164-176 (2009)
50. K. Hayakawa, L. D. Pham, A. T. Som, B. J. Lee, S. Guo, E. H. Lo, K. Arai, Vascular endothelial growth factor regulates the migration of oligodendrocyte precursor cells. *J Neurosci.* 31, 10666-10670 (2011)
51. E. Ercan, J. M. Han, A. Di Nardo, K. Winden, H. Min-Joo, L. Hoyo, A. Saffari, A. Leask, D. H. Geschwind, M. Sahin. Neuronal CTGF/CCN2 negatively regulates myelination in a mouse model of tuberous sclerosis complex. *J Exp Med.* 214, 681697 (2017)
52. S. Rosenzweig, S. T. Carmichael, Age-dependent exacerbation of white matter stroke outcomes: a role for oxidative damage and inflammatory mediators. *Stroke* 44, 2579-86 (2013)
53. J. A. Steinbeck, L. Studer, Moving stem cells to the clinic: potential and limitations for brain repair. *Neuron* 86, 187-206 (2015)
54. M. Saito, T. Iwawaki, C. Taya, H. Yonekawa, M. Noda, Y. Inui, E. Mekada, Y Kimata, A. Tsuru, K. Kohno, K. Diphtheria toxin receptor-mediated conditional and targeted cell ablation in transgenic mice. *Nat. Biotechnol.* 19, 746-750 (2001)
55. J. C. Dugas, B. Emery, Purification of oligodendrocyte precursor cells from rat cortices by immunopanning. *Cold Spring Harb Protoc.* 8, 745-758 (2013)
56. B. Anuncibay-Soto, D. Perez-Rodriguez, I. L. Llorente, M. M. Regueiro-Purrinos, J. M. Gonzalo-Orden, A. Fernandez-Lopez, Global cerebral ischemia modifies the vascular adhesion molecules, inflammation and apoptosis after 48 hours of reperfusion in age-dependent way. *Age* 36, 9703 (2014)
57. K. J. Livak, T. D. Schmittgen, Analysis of relative gene expression data using realtime quantitative PCR and the 2-AACt method. *Methods* 25, 402-408 (2001)
58. S. A. Bustin, V. Benes, J. A. Garson, J. Hellemans, J. Huggett, M. Kubista, S. Mueller, T. Nolan, M. W. Pfaffl, G. L. Shipley, J. Vandesompele, C. T. Wittwer, The MIQE guidelines: Minimum information for publication of quantitative real-time PCR experiments. *Clinical Chemistry* 4:55 (2009).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of improving recovery of a human after a cerebral ischemic injury, said method comprising cerebrally administering a therapeutically effective amount of differentiated cells to said human, wherein the differentiated cells are derived from human induced pluripotent stem cells (hiPSCs) or human embryonic stem cells (hESCs) that have been differentiated and cultured in NPC medium containing DFX for 3-5 days to produce cells whose differentiation potential is restricted to astrocytes; wherein the differentiated cells are syngeneic, allogenic, or are derived from the human; and wherein said differentiated cells are directly injected into or at about 0.05 mm to about 3 mm from the infarct core in the brain of said human during the subacute time period after a white matter stroke.

2. The method of claim 1, wherein: the cerebral ischemic injury is subcortical white matter stroke.

3. The method of claim 1, wherein said differentiated cells are administered using a depot delivery system.

4. The method of claim 3, wherein the depot delivery system comprises a hydrogel.

5. The method of claim 1, wherein said differentiated cells are derived from universal donor cells.

6. The method of claim 1, wherein said differentiated cells are derived from cells obtained from a human that is not the human being treated to provide cells that are allogenic to the human being treated.

7. The method of claim 6, wherein said method comprises administering one or more immunosuppressants to said human.

8. The method of claim 7, wherein said one or more immunosuppressants comprise an immunosuppressant selected from the group consisting of anti-thymocyte globulin (ATG), cyclosporine, tacrolimus, cyclophosphamide, and prednisone.

9. The method of claim 1, wherein said method comprises a method for improving motor or cognitive function of a human after a cerebral ischemic injury.

10. A method of slowing myelin loss, and/or promoting myelin repair, and/or promoting remyelination in a human having a demyelinating pathology that effects the central nervous system, said method comprising cerebrally administering a therapeutically effective amount of differentiated cells to said human, wherein the differentiated cells are derived from human induced pluripotent stem cells (hiPSCs) or human embryonic stem cells (hESCs) that have been differentiated and cultured in NPC medium containing DFX for 3-5 days to produce cells whose differentiation potential is restricted to astrocytes; wherein the differentiated cells are syngeneic, allogenic, or are derived from the human; and wherein said differentiated cells are directly injected into the brain of said human.

11. The method of claim 10, wherein said pathology is selected from the group consisting of multiple sclerosis, an inflammatory demyelinating disease, a leukodystrophic disorder, a CNS neuropathy, central pontine myelinolysis, a myelopathy, a leukoencephalopathy, and a leukodystrophy.

12. The method of claim 1, wherein the cerebral ischemic injury is vascular dementia.

13. The method of claim 1, wherein the cells express glial fibrillary acidic protein (GFAP), Growth Differentiation Factor 15 (GDF15), and vascular endothelial growth factor alpha (VEGFA).

* * * * *